(12) United States Patent
Wang et al.

(10) Patent No.: US 10,539,523 B2
(45) Date of Patent: Jan. 21, 2020

(54) SYSTEM AND METHOD FOR MONITORING CARDIOMYOCYTE BEATING, VIABILITY, MORPHOLOGY, AND ELECTROPHYSIOLOGICAL PROPERTIES

(71) Applicant: ACEA Biosciences, Inc., San Diego, CA (US)

(72) Inventors: Xiaobo Wang, San Diego, CA (US); Wei Ouyang, San Diego, CA (US); Nan Li, San Diego, CA (US); Tianxing Wang, Hangzhou (CN); Xiaoyu Zhang, San Diego, CA (US); Xiao Xu, San Diego, CA (US); Yama A. Abassi, San Diego, CA (US)

(73) Assignee: ACEA Biosciences, Inc., San Diego, CA (US)

( * ) Notice: Subject to any disclaimer, the term of this patent is extended or adjusted under 35 U.S.C. 154(b) by 0 days.

(21) Appl. No.: 14/092,927

(22) Filed: Nov. 28, 2013

(65) Prior Publication Data
US 2014/0203818 A1  Jul. 24, 2014

Related U.S. Application Data

(63) Continuation-in-part of application No. 12/774,709, filed on May 5, 2010, which is a continuation-in-part
(Continued)

(51) Int. Cl.
*G01N 27/02* (2006.01)
(52) U.S. Cl.
CPC .................................. *G01N 27/02* (2013.01)

(58) Field of Classification Search
CPC ........................... G01N 27/02; G01N 33/4836
(Continued)

(56) References Cited

U.S. PATENT DOCUMENTS 2,656,508 A   10/1953 Coulter
3,259,842 A    7/1966 Coulter et al.
(Continued)

FOREIGN PATENT DOCUMENTS

EP    1138758    10/2001
EP    1195432     4/2002
(Continued)

OTHER PUBLICATIONS

Oka, Hiroaki, et al. "A new planar multielectrode array for extracellular recording: application to hippocampal acute slice." Journal of neuroscience methods 93.1 (1999): 61-67.*
(Continued)

*Primary Examiner* — Robert J Eom
(74) *Attorney, Agent, or Firm* — Wagenknecht IP Law Group PC

(57) ABSTRACT

Devices, systems and methods for monitoring excitable cells, such as cardiomyocytes, on microelectrode arrays that couple the electro-stimulation of excitable cells to induce or regulate cardiomyocyte beating and the simultaneous measurement of impedance and extracellular recording to assess changes in cardiomyocyte beating, viability, morphology or electrophysical properties in response to a plurality of treatments.

5 Claims, 32 Drawing Sheets

Related U.S. Application Data of application No. 12/435,569, filed on May 5, 2009, now Pat. No. 9,709,548, said application No. 12/774,709 is a continuation-in-part of application No. 11/235,938, filed on Sep. 27, 2005, now Pat. No. 7,732,127, which is a continuation-in-part of application No. 11/197,994, filed on Aug. 4, 2005, now Pat. No. 7,468,255, which is a continuation-in-part of application No. 11/055,639, filed on Feb. 9, 2005, now Pat. No. 7,560,269, which is a continuation-in-part of application No. 10/987,732, filed on Nov. 12, 2004, now Pat. No. 7,192,752, said application No. 11/235,938 is a continuation-in-part of application No. 11/198,831, filed on Aug. 4, 2005, now Pat. No. 8,263,375, said application No. 10/987,732 is a continuation-in-part of application No. 10/705,615, filed on Nov. 10, 2003, now Pat. No. 7,459,303, which is a continuation-in-part of application No. 10/705,447, filed on Nov. 10, 2003, now Pat. No. 7,470,533, application No. 14/092,927, filed on Nov. 28, 2013, which is a continuation-in-part of application No. 13/109,809, filed on May 17, 2011, now Pat. No. 9,612,234, which is a continuation-in-part of application No. 12/435,569, filed on May 5, 2009, now Pat. No. 9,709,548.

(60) Provisional application No. 61/191,684, filed on Sep. 11, 2008, provisional application No. 61/126,533, filed on May 5, 2008, provisional application No. 61/323,782, filed on Apr. 13, 2010, provisional application No. 61/310,557, filed on Mar. 4, 2010, provisional application No. 61/175,566, filed on May 5, 2009, provisional application No. 60/519,567, filed on Nov. 12, 2003, provisional application No. 60/630,131, filed on Nov. 22, 2004, provisional application No. 60/630,071, filed on Nov. 22, 2004, provisional application No. 60/613,872, filed on Sep. 27, 2004, provisional application No. 60/613,749, filed on Sep. 27, 2004, provisional application No. 60/630,809, filed on Nov. 24, 2004, provisional application No. 60/633,019, filed on Dec. 3, 2004, provisional application No. 60/647,159, filed on Jan. 26, 2005, provisional application No. 60/653,904, filed on Feb. 17, 2005, provisional application No. 60/673,678, filed on Apr. 21, 2005, provisional application No. 60/689,422, filed on Jun. 10, 2005, provisional application No. 60/435,400, filed on Dec. 20, 2002, provisional application No. 60/469,572, filed on May 9, 2003, provisional application No. 60/542,927, filed on Feb. 9, 2004, provisional application No. 60/548,713, filed on Feb. 27, 2004, provisional application No. 60/641,601, filed on Sep. 29, 2004, provisional application No. 60/598,608, filed on Aug. 4, 2004, provisional application No. 60/598,609, filed on Aug. 4, 2004, provisional application No. 60/647,189, filed on Jan. 26, 2005, provisional application No. 60/647,075, filed on Jan. 26, 2005, provisional application No. 60/660,829, filed on Mar. 10, 2005, provisional application No. 60/660,898, filed on Mar. 10, 2005, provisional application No. 61/191,684, filed on Sep. 11, 2008, provisional application No. 61/126,533, filed on May 5, 2008, provisional application No. 61/345,867, filed on May 18, 2010.

(58) Field of Classification Search
USPC .......................................................... 422/83
See application file for complete search history.

(56) References Cited

U.S. PATENT DOCUMENTS

| | | |
|---|---|---|
| 3,743,581 A | 7/1973 | Cady et al. |
| 3,890,201 A | 6/1975 | Cady et al. |
| 4,072,578 A | 2/1978 | Cady et al. |
| 4,225,410 A | 9/1980 | Pace |
| 4,686,190 A | 8/1987 | Cramer et al. |
| 4,920,047 A | 4/1990 | Giaever et al. |
| 5,001,048 A | 3/1991 | Taylor et al. |
| 5,134,070 A | 7/1992 | Casnig |
| 5,187,096 A | 2/1993 | Giaever et al. |
| 5,218,312 A | 6/1993 | Moro |
| 5,247,827 A | 9/1993 | Shah |
| 5,278,048 A | 1/1994 | Parce et al. |
| 5,284,753 A | 2/1994 | Goodwin |
| 5,514,555 A | 5/1996 | Springer et al. |
| 5,563,067 A | 10/1996 | Sugihara et al. |
| 5,601,997 A | 2/1997 | Tchao et al. |
| 5,622,872 A | 4/1997 | Ribi |
| 5,626,734 A | 5/1997 | Docoslis et al. |
| 5,643,742 A | 7/1997 | Malin et al. |
| 5,725,563 A | 3/1998 | Klotz |
| 5,766,934 A | 6/1998 | Guiseppi-Elie |
| 5,800,467 A | 9/1998 | Park et al. |
| 5,801,055 A | 9/1998 | Henderson |
| 5,810,725 A | 9/1998 | Sugihara et al. |
| 5,824,494 A | 10/1998 | Feldberg |
| 5,851,489 A | 12/1998 | Wolf et al. |
| 5,981,268 A | 11/1999 | Kovacs et al. |
| 6,033,628 A | 3/2000 | Kaltenbach |
| 6,051,422 A | 4/2000 | Kovacs et al. |
| 6,132,683 A | 10/2000 | Sugihara et al. |
| 6,169,394 B1 | 1/2001 | Frazier et al. |
| 6,232,062 B1 | 5/2001 | Keyyem et al. |
| 6,235,520 B1 | 5/2001 | Malin et al. |
| 6,280,586 B1 * | 8/2001 | Wolf et al. ............ 257/253 |
| 6,288,527 B1 | 9/2001 | Sugihara et al. |
| 6,368,795 B1 | 4/2002 | Hefti |
| 6,368,851 B1 | 4/2002 | Baumann et al. |
| 6,376,233 B1 | 4/2002 | Wolf et al. |
| 6,377,057 B1 | 4/2002 | Borkholder |
| 6,440,662 B1 | 8/2002 | Gerwen et al. |
| 6,448,030 B1 | 9/2002 | Rust et al. |
| 6,448,794 B1 | 9/2002 | Cheng et al. |
| 6,461,808 B1 | 10/2002 | Bodner et al. |
| 6,472,144 B2 | 10/2002 | Malin et al. |
| 6,485,905 B2 | 11/2002 | Hefti |
| 6,492,175 B1 | 12/2002 | Muller et al. |
| RE37,977 E | 2/2003 | Sugihara et al. |
| 6,535,822 B2 | 3/2003 | Mansky et al. |
| 6,566,079 B2 | 5/2003 | Hefti |
| 6,573,063 B2 | 6/2003 | Hochman |
| 6,596,499 B2 | 7/2003 | Jalink |
| 6,626,902 B1 | 9/2003 | Kucharczyk et al. |
| 6,627,461 B2 | 9/2003 | Chapman et al. |
| 6,630,359 B1 | 10/2003 | Caillat et al. |
| 6,637,257 B2 | 10/2003 | Sparks |
| 6,638,743 B2 | 10/2003 | Baumann et al. |
| RE38,323 E | 11/2003 | Sugihara et al. |
| 6,649,402 B2 | 11/2003 | Van der Weide et al. |
| 6,686,193 B2 | 2/2004 | Maher et al. |
| 6,716,620 B2 | 4/2004 | Bashir et al. |
| 6,723,523 B2 | 4/2004 | Lynes et al. |
| 6,803,229 B2 | 10/2004 | Martin et al. |
| 6,835,552 B2 | 12/2004 | Miles et al. |
| 6,846,639 B2 | 1/2005 | Miles et al. |
| 6,852,525 B1 | 2/2005 | Cantor |
| 6,998,249 B1 | 2/2006 | McKim et al. |
| 7,010,347 B2 | 3/2006 | Schecter |
| 7,192,752 B2 | 3/2007 | Xu et al. |
| 7,208,279 B2 | 4/2007 | Gilchrist et al. |
| 7,294,334 B1 | 11/2007 | Michal et al. |

(56) References Cited

U.S. PATENT DOCUMENTS

| | | | |
|---|---|---|---|
| 7,399,631 B2 | 7/2008 | Giaever et al. | |
| 7,459,303 B2 | 12/2008 | Wang et al. | |
| 7,468,255 B2 | 12/2008 | Xu et al. | |
| 7,470,533 B2 | 12/2008 | Xu et al. | |
| 7,476,827 B1 | 1/2009 | Bhuller et al. | |
| 7,510,699 B2 | 3/2009 | Black et al. | |
| 7,553,448 B2 | 6/2009 | Kumar et al. | |
| 7,560,269 B2 | 7/2009 | Wang et al. | |
| 7,732,127 B2 | 6/2010 | Wang et al. | |
| 7,842,246 B2 | 11/2010 | Wohlstadler et al. | |
| 7,876,108 B2 | 1/2011 | Abassi et al. | |
| 8,026,080 B2 | 9/2011 | Wang et al. | |
| 8,041,515 B2 | 10/2011 | Wang et al. | |
| 8,206,903 B2 | 6/2012 | Abassi et al. | |
| 8,263,375 B2 | 9/2012 | Abassi et al. | |
| 8,344,742 B2 | 1/2013 | Abassi et al. | |
| 8,420,363 B2 | 4/2013 | Wang et al. | |
| 8,916,357 B2 | 12/2014 | Abassi et al. | |
| 8,921,041 B2 | 12/2014 | Wang et al. | |
| 9,399,787 B2 | 7/2016 | Abassi et al. | |
| 9,612,234 B2 * | 4/2017 | Li | G01N 33/5061 |
| 9,625,472 B2 | 4/2017 | Xu et al. | |
| 9,709,548 B2 | 7/2017 | Wang et al. | |
| 10,012,636 B2 | 7/2018 | Wang et al. | |
| 10,067,121 B2 | 9/2018 | Abassi et al. | |
| 2002/0090649 A1 | 7/2002 | Chan et al. | |
| 2003/0032000 A1 | 2/2003 | Liu et al. | |
| 2003/0072549 A1 | 4/2003 | Facer et al. | |
| 2003/0104512 A1 | 6/2003 | Freeman et al. | |
| 2003/0116447 A1 | 6/2003 | Surridge et al. | |
| 2003/0157587 A1 | 8/2003 | Gomez et al. | |
| 2003/0166015 A1 | 9/2003 | Zarowitz et al. | |
| 2003/0211500 A1 | 11/2003 | Woosley | |
| 2004/0091397 A1 | 5/2004 | Picard | |
| 2004/0106095 A1 | 6/2004 | Thomson et al. | |
| 2004/0146849 A1 | 7/2004 | Huang et al. | |
| 2005/0014130 A1 | 1/2005 | Liu et al. | |
| 2005/0153425 A1 | 7/2005 | Xu et al. | |
| 2005/0182447 A1 | 8/2005 | Schecter | |
| 2005/0287065 A1 | 12/2005 | Suddarth et al. | |
| 2006/0057771 A1 | 3/2006 | Kovacs et al. | |
| 2006/0121446 A1 | 6/2006 | Abassi et al. | |
| 2006/0161073 A1 | 7/2006 | Singer et al. | |
| 2006/0216203 A1 | 9/2006 | Fuller et al. | |
| 2006/0240490 A1 | 10/2006 | Lee | |
| 2007/0042347 A1 | 2/2007 | Rosen et al. | |
| 2007/0087333 A1 | 4/2007 | Gruters et al. | |
| 2007/0212423 A1 | 9/2007 | Epstein et al. | |
| 2008/0190783 A1 | 8/2008 | Hyland | |
| 2008/0286750 A1 | 11/2008 | Xu et al. | |
| 2009/0017465 A1 | 1/2009 | Xu et al. | |
| 2009/0142790 A1 | 6/2009 | Fang et al. | |
| 2009/0241698 A1 | 10/2009 | Biksacky | |
| 2010/0029506 A1 | 2/2010 | Wang et al. | |
| 2011/0039294 A1 | 2/2011 | Wang et al. | |
| 2011/0231103 A1 | 9/2011 | Fang | |
| 2011/0300569 A1 | 12/2011 | Li et al. | |
| 2012/0142031 A1 | 6/2012 | Xu et al. | |
| 2012/0322050 A1 | 12/2012 | Abassi et al. | |
| 2013/0123136 A1 | 5/2013 | Abassi et al. | |
| 2015/0125894 A1 | 5/2015 | Laing et al. | |
| 2015/0185206 A1 | 7/2015 | Abassi et al. | |
| 2015/0231634 A1 | 8/2015 | Szita et al. | |
| 2017/0205391 A1 | 7/2017 | Li et al. | |
| 2017/0269062 A1 | 9/2017 | Abassi et al. | |
| 2017/0315131 A1 | 11/2017 | Xu et al. | |
| 2017/0370907 A1 | 12/2017 | Abassi et al. | |
| 2018/0246079 A1 | 8/2018 | Wang et al. | |

FOREIGN PATENT DOCUMENTS

| | | |
|---|---|---|
| EP | 1 040 345 B1 | 3/2006 |
| EP | 2213721 | 8/2010 |
| EP | 2291645 | 9/2015 |
| WO | 1996/01836 | 1/1996 |
| WO | 1999/66329 | 12/1999 |
| WO | 2000/37628 | 6/2000 |
| WO | 2000/70343 | 11/2000 |
| WO | 2000/71669 | 11/2000 |
| WO | 2001/25769 | 4/2001 |
| WO | 2001/038873 | 5/2001 |
| WO | 2001/79529 | 10/2001 |
| WO | 2002/004943 | 1/2002 |
| WO | 2002/042766 | 5/2002 |
| WO | 2003/016887 | 2/2003 |
| WO | 2004/010103 | 1/2004 |
| WO | 2005/005979 | 1/2005 |
| WO | 2005/047482 | 5/2005 |
| WO | 2005/077104 | 8/2005 |
| WO | 2006/017762 | 2/2006 |
| WO | 2009/137440 | 11/2009 |
| WO | 2010/129725 | 11/2010 |
| WO | 2011/146531 | 11/2011 |
| WO | 2012/043820 A1 | 4/2012 |
| WO | 2012043820 A1 | 4/2012 |
| WO | 2014/085727 A1 | 6/2014 |
| WO | 2014085727 A1 | 6/2014 |
| WO | 2017/068421 A1 | 4/2017 |
| WO | 2017/087945 A1 | 5/2017 |

OTHER PUBLICATIONS

Yang, Mo, et al. "A novel microfluidic impedance assay for monitoring endothelin-induced cardiomyocyte hypertrophy." Biosensors and Bioelectronics22.8 (2007): 1688-1693.*
Ehret, R., et al. "On-line control of cellular adhesion with impedance measurements using interdigitated electrode structures." Medical and Biological Engineering and Computing 36.3 (1998): 365-370.*
HP 4284A Precision LCR Meter Operation Manual, Aug. 1998, Hewlett Packard, 6th Edition, p. 1-460.*
Baumen et al. "Microelectronic sensor system for microphysical application on living cells." Sensors and Actuators, 1999, 77-89.
Berens et al. "The role of extracelluar matrix in human astrocytoma migration and proliferation studied in a microliter scale assay." Clin. Exp. Metastasis, 1994, 12(6):405-415.
Bieberich et al. "Neuronal differentiation and synapse formation of PC12 and embryonic stem cells on interdigitated microelectrode arrays: Contact structures for neuron-to-electrode signal transmission (NEST)." Biosensors and Bioelectronics, 2004, 19:923-931.
Burnett et al. "Fluorescent imaginng of electrically stimulated cells." Journal of Biomolecular Screening, 2003, 8(6):660-667.
Cady et al. "Electrical Impedance Measurements: Rapid Method for Detecting and Monitoring Microorganisms." J. Clin. Mirobiol., 1978, 7(3):265-272.
Ehret et al. "Monitoring of cellular behaviour by impedance measurements on interdigitated electrode structures." Biosensors and Bioelectronics, 1997, 12(1):29-41.
Ehret et al. "On-line control of cellular adhesion with impedance measurements using interdigitated electrode structures." Med. Biol. Eng. Comput., 1998, 36:365-370.
Giaever et al. "Micromotion of mammalian cells measured electrically." Proc. Natl. Acad. Sci. USA, Sep. 8, 1991, 38:7896-7900.
Giaever et al. "Monitoring fibroblast behavior in tissue culture with an applied electric field." Proc. Natl. Acad. Sci. USA; 1984; 81:3761-3764.
Henning et al. "Approach to a mutliparametric sensor-chip-based tumor chemosensitivity assay." Anti-Cancer Drugs, 2001, 12:21-32.
Hidalgo et al. "Characterization of the human colon carcinoma cell line (Caco-2) as a model system for intestinal epithelial Permeability." 1989, 96:736-749.
Hug, Thomas. "Biophysical methods for monitoring cell-substrate interactions in drug discovery." Assay and Drug Development Technologies, 2003, 1(3):479-488.
Kleinman et al. "Basement membrane complexes with biological activity." Biochemistry, 1986, 25(2):312-318.
Aravanis et al. "A genetically engineered cell-based biosensor for functional classification of agents." Biosensors & Bioelectronics, 2001,16:571-577.

(56) References Cited

OTHER PUBLICATIONS

Baumann et al. "Microelectronic sensor system for microphysiological application on living cells." Sensors & Accuators, 1999, B55:77-89.
Becker et al. "Separation of human breast cancer cells from blood by differential dielectric affinity." Cell Biology, 1995, 92:960-964.
Berens et al. "The role of extracellular matrix in human astrocytoma migration and proliferation studied in a microliter scale assay." Clin. Exp. Metastasis, 1994, 12:405-415.
Bergveld, P. "A critical evaluation of direct electrical protein detection methods." Biosensors & Bioelectronics. 6:55-72 (1991).
Burns et al. "Neutrophil Transendothelial Migration Is Independent of Tight Junctions and Occurs Preferentially at Tricellular Corners." Journal of Immunology, 1997, 2893-2903.
Ciambrone et al. "Cellular Dielectric Spectroscopy: A Powerful New Approach to Label-Free Cellular Analysis." J. Biomo. Screening, 2004, 9(6):467-480.
Duan et al. "Separation-Free Sandwich Enzyme Immunoassays Using Microporous Gold Electrodes and Self-Assembled Monolayer/Immobilized Capture Antibodies." Anal. Chem., 1994, 66:1369-1377.
Gutmann et al. "Evidence for Different ABC-Transporters in Caco-2 Cells Modulating Drug Uptake." Pharmaceutical Research, 1999, 16(3):402-407.
Hug, Thomas S. "Biophysical Methods for Monitoring Cell-Substrate Interactions in Drug Discovery." Assay and Drug Dev. Tech., 2003, 1(3):479-488.
Lin and Huang. "Electroporation microchips for in vitro gene transfection." J. Micromech. Microeng., 2001,11:542-547.
Lin et al. "Simulation and experimental demonstration of the electric field assisted electroporation microchip for in vitro gene delivery enhancement" Min. For Chem., Bio., & Bioeng., 2004, 4:104-108.
Lo et al. "Impedance Analysis of MDCK cells measured by electric cell-substrate impedance sensing." Biophysical Journal, 1995, 69:2800-2807.
Mitra et al. "Electric measurements can be used to monitor the attachment and spreading of cells in tissue culture." Biotechniques, 1991, 11(4):504-510.
Miyata et al. "New Wound-Healing Model Using Cultured Corneal Endothelial Cells." Jpn. J. Opthalmol., 1990, 34:257-266.
Mohr et al. "Performance of a thin film microelectrode array for monitoring electrogenic cells in vitro." Sensors and Actuators, 1996, B34:265-269.
Nerurkar et al. "The Use of Surfactants to Enhance the Permeability of Peptides Through Caco-2 Cells by Inhibition of an Apically Polarized Efflux System." Pharmaceutical Research, 1996,13(4):528-534.
"Molecular Viewer" New Products page. Science, 298:2409 (2002).
"Cell Migration Studies with Tecan Systems." TECAN., Sep. 1999, [retrieved from the internet] http://www.tecan.com/migration_introl.pdf, 10 pgs.
"Detect Cell Migration and Invasion in a Homogeneous Fluorescent Assay System." BD Biosciences, [retrieved from the internet] http://www.bdbiosciences.com/discovery_labware/Products/inserts/BD_Falcon_HTS_fluoroblok_inserts/individual_fluoroblok_inserts/index.html, 2004.
"Neuro Probe AA96, AB96, AC96 Chemotaxis Chambers." Neuro Probe, [retrieved from the internet] http://www.neuroprobe.com/protocol/pt_96a.html, 5 pgs.
"Automated Cell Monitoring Instrument." Applied BioPhysics, 2002, [retrieved from the internet] http://www.biophysics.com/pages/front.html, 1 page.
Yamauchi et al. "Spatially and temporally controlled gene transfer by electroporation into adherent cells on plasmid DNA-loaded electrodes." Nuc. Acids Res., 2004, 32(22):1-8.
Yang et al. "Celli Separation on Microfabricated Electrodes Using dielectrophoretic/Gravitational field-flow Fractionation." Anal. Chem., 1999, 71:911-918.

Connolly et al. "An extracellular microelectrode array for monitoring electrogenic cells in culture." Biosensors & Bioelectronics, 1990, 5:223-234.
Falk et al. "A 48-well Micro Chemotaxis Assembly for Rapid and Accurate Measurement of Leukocyte Migration." J. Immunol. Meth., 1980, 33:239-247.
Fuhr et al. "Positioning and Manipulation of Cells and Microparticles Using Miniaturized Electric Field Traps and Travelling Waves." Sensors and Materials 7(2):131-146 (1995).
Hadjout et al., Automated Real-Time Measurement of Chemotactic Cell Motility Biotechniques 31:1130-1138 (2001).
Huang et al., Dielectrophoretic Cell Separation and Gene Expression Profiling on Microelectronic Chip Arrays. Anal. Chem. 74:3362-3371 (2002).
Keese et al., Real-time impedance assay to follow the invasive activities of metastatic cells in culture. Biotechniques, 2002,33:842-850.
Larsen et al. "Somatic Cell Counting with Silicon Apertures." Micro Total Analysis Systems, 2000, 103-106.
Lo et al. "pH Changes in pulsed $CO_2$ incubators cause periodic changes in cell morphology." Experimental Cell Research, 213:391-397 (1994).
Wegener et al. "Electric cell-substrate impedance sensing system (ECIS) as a noninvasive means to monitor the kinetics of cell spreading to artificial surfaces." Eur. J. Physiol., 1999, 437:925-934.
Banach et al. "Development of Electrical Activity in Cardiac Myocyte Aggregates Derived from Mouse Embryonic Stem Cells." Am J Physiol Heart Circ Physiol, 2003, 284: H2114-H2123.
Hescheler et al. "Determination of Electrical Properties of ES Cell-derived Cardiomyocytes Using MEAs." Journal of Electrocardiology, 2004, vol. 37, Suppl.
Horvath et al. "Monitoring of Living Cell Attachment and Spreading Using Reverse Symmetry Waveguide Sensing." Applied Physics Letters, 2005, 86:071101.
Kowolenko et al., Measurement of macrophage adherence and spreading with weak electric fields, Journal of Immunological Methods, 1990; 127:71-77.
Lo et al., Monitoring motion of confluent cells in tissue culture, Experimental Cell Research 1983; 204:102-109.
Luong et al., Monitoring motility, spreading and mortality of adherent insect cells using an impedance sensor, Anal. Chem 2001; 73(8):1844-1848.
Neher, Erwin, Molecular biology meets microelectronics, Nature Biotechnology, 2001; 19:114.
Ong et al., Remote query resonant-circuit sensors for monitoring of bacterial growth: Application to food quality control, Sensors 2002; 2:219-232.
Pancrazio et al., Portable cell-based biosensor system for toxin detection, Sensors and Actuators 1998; 53:179-185.
Slaughter et al., Artificial neural network for temporal impedance recognition of neurotoxins, 2006 International Joint Conference on Neural Networks 2006; Jul. 16-21, 2001-2008.
Stenger et al., Detection of physiologically active compounds using cell-based biosensors, Trends in Biotechnology, 2001; 19(8):304-309.
Wang et al., A theoretical method of electrical field analysis for dielectrophoretic electrode arrays using Green's theorem, J. Phys. D: Appl. Phys 1996; 29:1649-1660.
Wegener et al., Electric cell-substrate impedance sensing (ECIS) as noninvasive means to monitor the kinetics of cell spreading to artificial surfaces, Experimental Cell Research 2000; 259:158-166.
Wolf et al., Monitoring of cellular signalling and metabolism with modular sensor-technique: The PhysioControl-Microsystem (PCM), Biosensors and Bioelectronics 1998; 13:501-509.
Xiao et al., Assessment of cytotoxicity using electric cell-substrate impedance sensing: Concentration and time response function approach, Anal. Chem 2002, 74:5748-5753.
Xiao et al., An in-depth analysis of electric cell-substrate impedance sensing to study the attachment and spreading of mammalian cells, Anal. Chem 2002; 74(6):1333-1339.
Xiao et al., On-line monitoring of cell growth and cytotoxicity using electric cell-substrate impedance sensing (ECIS), Biotechnol. Prog. 2003; 19:1000-1005.

(56) References Cited

OTHER PUBLICATIONS

Berdondini et al. "High-density electrode array for imaging in vitro electrophysiological activity." Biosensors and Bioelectronics, 2005, 21:167-174.
Chang et al. "Impedimetric monitoring of cell attachment on interdigitated microelectrodes." Sensors and Actuators, 2005, B 105:159-163.
Yang et al. "A novel microfluidic impedance assay for monitoring endothelin-induced cardiomyocyte hypertrophy." Biosensors and Bioelectronics, 2007, 22:1688-1693.
PCT/US2009/033801 International Search Report and Written Opinion dated Jul. 9, 2010.
PCT/US2009/042787 International Search Report and Written Opinion dated Jun. 24, 2009.
PCT/US2011/036877 International Search Report dated Sep. 2, 2011.
PCT/US2013/072439 International Search Report dated Feb. 19, 2014.
PCT/US2005/034561 International Preliminary Report on Patentability dated Mar. 27, 2007.
PCT/US2005/034561 International Search Report dated Sep. 27, 2006.
PCT/US2005/027943 International Preliminary Report on Patentability dated Apr. 11, 2007.
PCT/US2005/027943 International Search Report and Written Opinion dated Mar. 21, 2007.
PCT/US2004/037696 International Search Report dated May 16, 2005.
PCT/US2005/04481 International Search Report dated Sep. 12, 2005.
EP05722991 Extended European Search Report dated Apr. 3, 2009.
EP11193882 Extended European Search Report dated Apr. 5, 2012.
EP13171137 Extended European Search Report dated Aug. 16, 2013.
EP05786773 Extended European Search Report dated Mar. 21, 2013.
EP05852157 Extended European Search Report dated Sep. 13, 2011.
EP058122680 Extended European Search Report dated Sep. 7, 2011.
EP03748948 Extended European Search Report dated Mar. 12, 2007.
CA2556219 Office Action dated Aug. 9, 2010.
CA2575573 Office Action dated Apr. 4, 2012.
EP09743420 European Search Report dated Nov. 26, 2013.
Kloss et al. "Microcavity array (MCA)-based biosensor chip for functional drug screening of 3D tissue models" Biosensors and Bioelectronics, 2008, 23:1473-1480.
Oka et al. "A new planar multielectrode array for extracellular recording: application to hippocampal acute slice." Journal of Neuroscience Methods, 1999, 93:61-67, Elsevier Science, B.V.
Qiu et al. "Real-Time Monitoring Primary Cardiomyocyte Adhesion Based on Electrochemical Impedance Spectroscopy and Electrical Cell-Substrate Impedance Sensing" Anal. Chem., 2008, 80:990-996.
Yu et al. "Real-Time Monitoring of Morphological Changes in Living Cells by Electronic Cell Sensor Arrays: An Approach To Study G Protein-Coupled Receptors" Anal. Chem., 2006, 78:35-43.
Xing et al. "Dynamic Monitoring of Cytotoxicity on Microelectronic Sensors" Chem. Res. Toxicol., 2005, 18 (2)154-161.
Blagbrough et al. "Polyamines and novel polyamine conjugates interact with DNA in ways that can be exploited in non-viral gene therapy." Biochemical Society Transactions, 2003, 31, Part 2, pp. 397-406.
Bonetta, Laura. "The inside scoop-evaluating gene delivery methods." Nature Methods, Nov. 2005, 2 (11):875-883.
Hapala, Ivan. "Breaking the Barrier: Methods for Reversible Permeabilization of Cellular Membranes." Critical Reviews in Biotechnology, 1997, 17(2):105-122.
Loffert et al. "Multiplex PCR with QIAGEN: Taq DNA Plymerase and PCR Buffer." QIAGENews, 1994, 4:15-18.
Luan and Li. "Clustering of time-course gene expression data using a mixed-effects model with B-splines." Bioinformatics, 2003, 19(4):474-482.
Nicoazzi et al. "Cationic Lipids for Transfection." Current Medicinal Chemistry, 2003, 10:1263-1277.
Rabow et al. "Mining the National Cancer Institute's Tumor-Screening Database: Identification of Compounds with Similar Cellular Activities." J. Med. Chem., 2002, 45:818-840.
Steinem et al. "Impedance and shear wave resonance analysis of ligand-receptor interactions at functionalized surfaces and of cell monolayers." Biosensors & Bioelectronics, 1997, 12(8):787-808.
Patolsky et al., Detection of single-base DNA mutations by enzyme-amplified electronic transduction. Nature Biotechnology 19:253-257 (2001).
Pethig et al., Positive and negative dielectrophoretic collection of colloidal particles using interdigitated castellated microelectrodes. Appl. Phys. 24:881-888 (1992).
Richards et al., A Modified Microchamber Method for Chemotaxis and Chemokinesis. Immunological Communications 13 (1):49-62.
Rishpon et al., An Amperometric Enzyme-channeling Immunosensor. Biosensors & Bioelectronicsd, 12(3):195-204 (1997).
Simpson et al. "Whole-cell biocomputing." Trends in Biotechnology, 2001, 19(9):317-323.
Sohn et al. "Capacitance cytometry: Measuring biological cells one by one." Proc. Nat. Acad. Sci., 2000, 97 (20):10687-10690.
Svetlicic et al. "Charge Displacement by adhesion and spreading of a cell." Bioelectrochemistry, 2000, 53:79-86.
Tiruppathi et al. "Electrical method for detection of endothelial cell shape change in time: assessment of endothelial barrier function." Proc Natl Acad Sci USA , 1992, 89:7919-7923.
Wang et al. "Selective Dielectrophoretic confinement of bioparticles in potential energy wells." Appl. Phys., 1993, 26:1278-1285.
Wang et al. "Cell Separation by Dielectrophoretic Field-flow-fractionation." Anal. Chem., 2000, 72:832-839.
Wang et al. "Dielectrophoretic Manipulation of Cells with Spiral Electrodes." Biophysical Journal, 1997, 72:1887-1899.
Wang et al. "Separation of Polystyrene Microbeads Using Dielectrophoretic/Gravitational Field-Flow-Fractionation." Biophysical Journal, 1998, 74:2689-2701.
Wang et al. "Electronic Manipulation of Cells on Microchip-Based Devices." In Biochip Technology (eds), pp. 135-159, Harwood Academic Publishers, PA, USA.
Warburg E., "Ueber die Polarisationscapacitaet des Platins," Ann Phys, 1901, 6:125-135.
Wegener et al. "Use of Electrochemical Impedance Measurements to Monitor beta-Adrenergic Stimulation of Bovine Aortic Endothelial Cells," European Journal of Physiology, 1999, 437:925-934.
Klauke et al. "Extracellular Recordings of Field Potentials from Single Cardiomyocytes," Biophysical Journal, Oct. 2006, 91(7)2543-2551.
Lo et al. "Abstract C1.00268: Effect of cMet Inhibitor on HGF-Induced Ovarian Carcinoma Cell Migration," American Physical Societal March Meeting, 2010, Portland Oregon, vol. 55, No. 2 poster session.
10772804.0 Extended European Search Report dated Oct. 27, 2017.
Fusenig et al. "The Need for a Worldwide Consensus for Cell Line Authentication: Experience Implementing a Mandatory Requirement at the Internation International Journal of Cancer". PLOS Biologiy, Apr. 17, 2017, 15(4) p. e2001438 pp. 1-13.
PCT/US2016/063066 ISR and WO dated Jan. 30, 2017.
PCT/US2018/044774 ISR and WO dated Oct. 23, 2018.

\* cited by examiner

SYSTEM AND METHOD FOR MONITORING CARDIOMYOCYTE BEATING, VIABILITY, MORPHOLOGY, AND ELECTROPHYSIOLOGICAL PROPERTIES

CROSS REFERENCE TO RELATED APPLICATIONS

This application claims benefit of priority to U.S. provisional patent application Ser. No. 61/730,427 filed Nov. 27, 2012, entitled, "System and method for monitoring cardiomyocyte beating, viability, morphology and electrophysiological properties."

This application is also a continuation in part of U.S. patent application Ser. No. 12/774,709 filed May 5, 2010, entitled, "System and method for monitoring cardiomyocyte beating, viability and morphology and for screening for pharmacological agents which may induce cardiotoxicity or modulate cardiomyocyte function", which is a continuation in part of U.S. patent application Ser. No. 12/435,569, filed May 5, 2009, entitled, "Label free monitoring of excitation-contraction coupling and excitable cells using impedance based systems with millisecond time resolution," which claims priority to U.S. provisional patent application Ser. No. 61/191,684, filed Sep. 11, 2008, and U.S. provisional patent application Ser. No. 61/126,533, filed May 5, 2008; the contents of each are herein incorporated by reference in their entirety.

Parent U.S. patent application Ser. No. 12/774,709 also claims priority to U.S. patent application Ser. No. 61/323,782, filed on Apr. 13, 2010, entitled, "Impedance based monitoring of cardiomyocytes"; U.S. patent application Ser. No. 61/310,557, filed Mar. 15, 2010, entitled, "Impedance based monitoring of cardiomyocytes"; and U.S. patent application Ser. No. 61/175,566, filed May 5, 2009, entitled, "System and method for monitoring cardiomyocyte beating, viability and morphology and for screening for pharmacological agents which may induce cardiotoxicity or modulate cardiomyocyte function." All of the applications referred to in this paragraph are incorporated by reference in their entireties herein.

Parent U.S. patent application Ser. No. 12/774,709 is also a continuation in part of U.S. patent application Ser. No. 11/235,938 entitled, "Dynamic Monitoring of Cell Adhesion and Spreading Using the RT-CES System", filed on Sep. 27, 2005, now U.S. Pat. No. 7,732,127, which is a continuation in part of U.S. patent application Ser. No. 11/197,994, now U.S. Pat. No. 7,468,255, entitled, "Method for Assaying for Natural Killer, Cytotoxic T-Lymphocyte and Neutrophil-Mediated Killing of Target Cells Using Real-Parent U.S. patent application Ser. No. 12/774,709 is also a continuation in part of U.S. patent application Ser. No. 11/235,938 entitled, "Dynamic Monitoring of Cell Adhesion and Spreading Using the RT-CES System", filed on Sep. 27, 2005, now U.S. Pat. No. 7,732,127, which is a continuation in part of U.S. patent application Ser. No. 11/197,994, now U.S. Pat. No. 7,468,255, entitled, "Method for Assaying for Natural Killer, Cytotoxic T-Lymphocyte and Neutrophil-Mediated Killing of Target Cells Using Real-Time Microelectronic Cell Sensing Technology", filed on Aug. 4, 2005, which is a continuation-in-part of U.S. patent application Ser. No. 11/055,639, now U.S. Pat. No. 7,560,269, entitled "Real time electronic cell sensing system and applications for cytotoxicity profiling and compound assays" filed on Feb. 9, 2005 which is a continuation-in-part of U.S. patent application Ser. No. 10/987,732, now U.S. Pat. No. 7,192,752, entitled "Real time electronic cell sensing system and application for cell based assays" filed on Nov. 12, 2004, which claims priority to U.S. provisional application Ser. No. 60/519,567, filed on Nov. 12, 2003. All applications referred to in this paragraph are incorporated by reference in their entireties herein.

Parent U.S. patent application Ser. No. 11/235,938, also claims benefit of priority to U.S. provisional patent application Ser. No. 60/630,131, filed on Nov. 22, 2004; U.S. provisional patent application Ser. No. 60/630,071 filed on Nov. 22, 2004; U.S. provisional patent application Ser. No. 60/613,872 filed on Sep. 27, 2004; U.S. provisional patent application Ser. No. 60/613,749, filed on Sep. 27, 2004; U.S. provisional patent application Ser. No. 60/630,809 filed on Nov. 24, 2004; U.S. provisional patent application Ser. No. 60/633,019 filed on Dec. 3, 2004; U.S. provisional patent application Ser. No. 60/647,159 filed on Jan. 26, 2005; U.S. provisional patent application Ser. No. 60/653,904 filed on Feb. 17, 2005; and U.S. provisional patent application Ser. No. 60/673,678 filed on Apr. 25, 2005; U.S. provisional patent application Ser. No. 60/689,422 filed on Jun. 10, 2005. All of the applications referred to in this paragraph are incorporated by reference in their entireties herein.

Parent U.S. patent application Ser. No. 11/235,938 is also a continuation-in-part of U.S. patent application Ser. No. 11/198,831, entitled, "Dynamic Monitoring of Activation of G-Protein Coupled Receptor (GPCR) and Receptor Tyrosine Kinase (RTK) in Living Cells using Real-Time Microelectronic Cell Sensing Technology, filed on Aug. 4, 2005, now U.S. Pat. No. 8,263,375, which is herein incorporated by reference in its entirety.

Parent U.S. patent application Ser. No. 10/987,732, now U.S. Pat. No. 7,192,752, is also a continuation-in-part of U.S. patent application Ser. No. 10/705,615, now U.S. Pat. No. 7,459,303, entitled "Impedance Based Apparatuses and Methods for Analyzing Cells and Particles", filed on Nov. 10, 2003, which claims priority to U.S. provisional patent application Ser. No. 60/397,749 filed on Jul. 20, 2002; U.S. provisional patent application Ser. 60/435,400, filed on Dec. 20, 2002; and U.S. provisional patent application Ser. No. 60/469,572, filed on May 9, 2003. All of the applications referred to in this paragraph are incorporated by reference in their entireties herein.

Parent U.S. patent application Ser. No. 10/987,732, now U.S. Pat. No. 7,192,752, is also a continuation in part of U.S. patent application Ser. No. 10/705,447, now U.S. Pat. No. 7,470,533, filed on Nov. 10, 2003, entitled "Impedance Based Devices and Methods for Use in Assays" which claims priority to U.S. provisional patent application Ser. No. 60/397,749, filed on Jul. 20, 2002; U.S. provisional patent application Ser. No. 60/435,400, filed on Dec. 20, 2002; and U.S. provisional patent application Ser. No. 60/469,572, filed on May 9, 2003. All of the applications referred to in this paragraph are incorporated by reference in their entireties herein.

Parent U.S. patent application Ser. No. 11/055,639, now U.S. Pat. No. 7,560,269 also claims priority to U.S. provisional patent application Ser. No. 60/542,927 filed on Feb. 9, 2004; U.S. provisional patent application Ser. No. 60/548,713, filed on Feb. 27, 2004, and U.S. provisional patent application Ser. No. 60/614,601, filed on Sep. 29, 2004. All of the applications referred to in this paragraph are incorporated by reference in their entireties herein.

Parent U.S. patent application Ser. No. 11/197,994, now U.S. Pat. No. 7,468,255 also claims priority to U.S. provisional patent application Ser. No. 60/598,608, filed on Aug. 4, 2004, U.S. provisional patent application Ser. No. 60/630,131, filed on Nov. 22, 2004, U.S. provisional patent application Ser. No. 60/689,422, filed on Jun. 10, 2005, U.S. provisional patent application Ser. No. 60/598,609, filed on Aug. 4, 2004, U.S. provisional patent application Ser. No. 60/613,749, filed on Sep. 27, 2004, U.S. provisional patent application Ser. No. 60/647,189, filed on Jan. 26, 2005, U.S. provisional patent application Ser. No. 60/647,075, filed on Jan. 26, 2005, U.S. provisional patent application Ser. No. 60/660,829, filed on Mar. 10, 2005, and U.S. provisional patent application Ser. No. 60/660,898, filed on Mar. 10, 2005. All of the applications referred to in this paragraph are incorporated by reference in their entireties herein.

TECHNICAL FIELD

This invention relates to the field of cell-based assays and more specifically to devices, systems and methods for electro-stimulation of excitable cells, such as cardiomyocyte or cardiomyocyte precursor cells and performing extracellular recording and/or impedance monitoring of electro-stimulated cells.

BACKGROUND OF THE INVENTION

Bioelectronics is a progressing interdisciplinary research field that involves the integration of biomaterials with electronic devices. Bioelectronics methods have been used for analyzing cells and assaying biological molecules and cells. In one type of application, cells are cultured on microelectrodes and cell-electrode impedance or cell-substrate impedance is measured and analyzed to monitor cellular changes, such as changes in cell morphology. For example, PCT Application No. PCT/US03/22557, titled "Impedance Based Devices and Methods for Use in Assays", discloses a device for detecting cells and/or molecules on an electrode surface. The device detects cells and/or molecules through measurement of impedance changes resulting from the attachment or binding of cells and/or molecules to the electrode surfaces. A number of embodiments of the device are disclosed, together with the apparatuses, and systems for using such devices to perform certain cell based assays.

Bringing a new drug to the market can take anywhere between 8 to 16 years, and the average cost of developing a drug is now around $500-$800 million with the cost expected to hit the $1 billion mark within the next four years. Cardiotoxicity has been cited as the reason for 30 percent of all failed drug compounds during development and is a major cause of compound attrition. The late detection of cardiotoxic side effects caused by pharmacological compounds can impede drug discovery and development projects, and consequently increase their cost. Testing for the potential cardiotoxic side effects of compounds at an early stage of drug development has therefore been the goal of many pharmaceutical and biotechnology companies. Cardiotoxicity itself can entail a number of short-term and long term cellular events including directly affecting the beating rate of cardiomyocytes, viability of cardiomyocytes and morphology of cardiomyocytes as would occur in hypertrophy. The core of the current issue in pharmacological safety assessment and drug development is the lack of a reliable screening methodology capable of monitoring potential drug-mediated cardiotoxicity and distinguishing between different modes of cardiotoxicity. What is urgently needed in the field is a good cell-based model system as well as a monitoring system with a physiological and functional read-out that can provide incisive information regarding potential cardiotoxic side effects of drugs.

Traditionally, the drug discovery industry has undertaken two different approaches for toxicological assessment of drug candidate leads in cardiac function. The first approach involves isolation of cardiomyocytes directly from a mammalian species such as rats and dogs followed by electrophysiological and viability studies on the isolated cardiomyocytes. This approach is extremely labor-intensive, time consuming and costly and at the same time not very amenable to the high throughput demands of pharmaceutical industry An alternative method for prediction of cardiotoxicity of drug candidate leads early in the drug development process has involved utilizing cell-based assay models which heterologously express specific ion channels such as hERG channels or voltage-gated calcium channels. These cardiac ion channels have been envisioned as possible molecular targets through which drugs could induce cardiotoxicity. These cell-based systems allow the assessment of drug-channel interaction by monitoring the effect of the drug on the currents produced by the different channels in cultured cells using a technique known as 'patch clamping', which isolates regions of the cell membrane containing channel proteins and measures changes in electrical potential difference. Use of this method in high throughput requires automation of patch clamping in array format, which even though is available in last several years is not yet widespread. Another issue with this approach is that cardiac toxicity may occur by other mechanisms which can easily be missed by this type of targeted approach.

An alternative to the in vitro ion-channel recording assays as well as the labor-intensive isolation of primary tissue is to utilize the differentiation of embryonic stem (ES) cells into cardiomyocytes as a starting material for functional assays. The utility of ES cells as a treatment for various chronic diseases has received much attention in recent years. Mammalian ES cells are self-renewing cells derived from the inner cell mass of a blastocyst stage embryo, which can be differentiated into multiple different cell types. It has been demonstrated that the mouse ES cells as well as human ES cells can be differentiated into cardiomyocytes, which retain the ability to beat in culture.

The differentiation of ES cells first involves an intermediate in vitro developmental stage in which ES cells form compact cell structures known as embryoid bodies. These embryoid bodies can induce the developmental program of ES cell differentiation into multiple cell types including cardiomyocytes, which are distinguished in culture by their ability to undergo spontaneous beating. These ES derived in vitro differentiated cardiomyocytes recapitulates the normal development of cardiomyocytes as evidenced by the stage-specific expression of cardiomyocyte specific genes. All the known transcription factors, ion channels and structural proteins that are part of normal heart development and function in vivo are also expressed in ES-derived cardiomyocyte.

Because ES cells are self-renewing, cells in culture can serve as an excellent source for continuous production of cardiomyocytes. Therefore, these cardiomyocytes which behave in every way like normal cardiomyocytes isolated from the heart tissue itself addresses the ever important supply problem and for the first time allows for assessment of cardiac function and its modulation by lead candidate drugs and compounds in relatively large scale in both viability assays, assessment of morphology and in monitoring the beating function of cardiomyocytes. Furthermore, because the technology exists to selectively knockout or express trans-genes in ES cells, it provides an excellent model system to study the role of certain genes in cardiac development and function without having to be concerned about adverse affects on overall embryonic development in transgenic animals.

The ability to express transgenes in ES cells has been utilized as a way to enrich for preparation of cardiomyocytes that are 100% pure. For example, the gene encoding GFP has been cloned downstream of a cardiac-specific promoter and then introduced into ES cells. Embryoid cells, which ultimately differentiate into cardiomyocytes, will therefore express the GFP transgenes and these cells can be easily isolated by cell sorting techniques and therefore an enriched cardiomyocyte population can be obtained.

Technologies designed to assess cardiomyocyte behavior and function and the effect of drugs and other manipulations in vitro can be divided into two different approaches. One approach involves long term assessment of cardiomyocyte viability for example in response to certain compounds. Such assays are typically end point assays designed to measure a cellular component such as ATP, which correlates with the degree of viability of the cells. The other approach involves studying short term effect of drugs and compounds on beating function of cardiomyocytes. High throughput techniques for short term functional characterization of ion channels and other targets in cardiomyocytes has been rather challenging and limited. Systems such as automatic patch clamp instrumentation that are available can monitor a single cardiomyocyte at a time and with very limited throughput.

In US 2011/0039294 an approach to monitoring a cardiomyocyte population is disclosed, which includes both impedance monitoring and extracellular recording technologies with high precision. While acceptance of the technology is increasing, there still remain challenges when working with the cells themselves. For example, when using primary cardiomyocyte cells harvested from tissue or after extended culturing, the beating of cells can stop or slow. Accordingly, there is a need to provide devices, systems and methods that assess the cardiotoxicity of compounds while working to ensure the continued or regular beating of cardiomyocyte cells.

SUMMARY OF THE INVENTION

The present invention discloses devices, systems and methods for performing impedance monitoring and/or extracellular recording of excitable cells, such as cardiomyocytes in cell based assays that encourage the continued and regular beating of excitable cells such that the cardiotoxicity of potential drugs can be assessed. In addition, the devices, systems and methods provide improved characterization of excitable cells in response to compound administration to assess responses of cardiomyocytes including cardiotoxic effects, while increasing efficiency of throughput for potential drug candidates. The invention further provides improved characterization of cells during differentiation processes related to development of cardiomyocytes.

In one aspect of the invention a system for monitoring excitable cells is disclosed, which includes a device having at least one well, each well having a bottom having a nonconductive substrate, wherein the substrate has a surface suitable for attachment of excitable cells; a power source configured to deliver an electrical signal capable of electro-stimulating excitable cells; and at least one analyzing module for measuring an electrical property from electro-stimulated excitable cells, characterized in that each well includes a pair of electro-stimulation electrodes configured to receive the electrical signal from the power source thereby delivering an electro-stimulating signal to the well for electro-stimulation of excitable cells attached to the substrate; and at least a second pair of electrodes communicatively coupled to the at least one analyzing module, which is selected from the group consisting of a pair of impedance monitoring electrodes communicatively coupled to the at least one analyzing module in the form of an impedance analyzer thereby permitting impedance monitoring of excitable cells attached to the substrate, and an extracellular recording electrode pair communicatively coupled to the at least one analyzing module in the form of an extracellular recording amplifier thereby permitting extracellular recording of excitable cells attached to the substrate.

In regards to electro-stimulation, in some embodiments the electrical signal is a series of pulses at a regular time interval, such as but not limited to 0.5 seconds to 2 seconds. The electrical signal can vary but is preferably 1V to 2.5V for 0.5-2 milliseconds. A percentage of a surface area of the bottom of the at least one well occupied by the pair of electro-stimulation electrodes can vary but in some embodiments is selected from the group consisting of 5% or more, 10% or more, 20% or more, 30% or more, 50% or more, and 70% or more. The electro-stimulation electrodes independently includes an unbranched electrode structure or a branched electrode structure.

In preferred impedance monitoring configurations, the at least second pair of electrodes is the pair of impedance monitoring electrodes and the analyzing module is in the form of the impedance analyzer. The pair of impedance monitoring electrodes can be provided in a variety of configurations but is preferably a pair of interdigitated electrode structures, wherein each electrode structure comprises a plurality of electrode elements. In addition, the pair of impedance monitoring electrodes can be a pair of electrode structures having a same surface area. In preferred embodiments the impedance analyzer monitors impedance at millisecond time resolution In further embodiments, the extracellular recording electrode pair as a third pair of electrodes. In still further embodiments at least one electrode of the pair of electro-stimulation electrodes is also at least one electrode of the extracellular recording electrode pair thereby permitting electro-stimulation of excitable cells and extracellular recording of attached cells using a same electrode at different time points.

In regards to extracellular recording, the at least second pair of electrodes can be the extracellular recording electrode pair and the analyzing module can be the extracellular recording amplifier. Preferably, the extracellular recording electrode pair includes a recording electrode and a reference electrode. In some embodiments the recording electrode has a diameter from about 10 µm to about 200 µm or from about 30 µm to about 100 µm. In some embodiments, the extracellular recording electrode pair comprises a recording electrode and a reference electrode, further wherein a ratio of the area of reference electrode to the area of recording electrode is selected from the group consisting of 2 or more, 10 or more, 100 or more, 1,000 or more, and 10,000 or more. In further embodiments a second recording electrode is provided having a same diameter as a first.

In some extracellular recording embodiments, at least one electrode of the pair of electro-stimulation electrodes is also at least one electrode of a pair of impedance monitoring electrodes thereby permitting electro-stimulation of excitable cells and impedance monitoring of attached cells using a same electrode at different time points and thus electro-stimulation together with simultaneous impedance monitoring using as few as four total electrodes. In such embodiments, preferably the pair of impedance monitoring electrodes is a pair of interdigitated electrode structures, wherein each electrode structure comprises a plurality of electrode elements. In variations of the extracellular recording embodiments, at least one electrode of the pair of impedance monitoring electrodes is the reference electrode.

In addition a device for monitoring excitable cells is also provided, the device including at least one well, each well having a bottom having a nonconductive substrate, wherein the substrate has a surface suitable for attachment of excitable cells; a pair of electro-stimulation electrodes positioned on the substrate within the at least one well and configured to electro-stimulate the excitable cells; and at least a second pair of electrodes positioned within the at least one well and selected from the group consisting of a pair of impedance monitoring electrodes and extracellular recording electrode pair, wherein the pair of impedance monitoring electrodes is configured for monitoring cell-substrate impedance of cells attached to the substrate, and wherein the extracellular recording electrode pair is configured for monitoring extracellular potential of cells attached to the substrate.

In regards to electro-stimulation electrodes a percentage of a surface area of the bottom of the at least one well occupied by the pair of electro-stimulation electrodes can vary but may be selected from the group consisting of 5% or more, 10% or more, 20% or more, 30% or more, 50% or more, and 70% or more. In some embodiments each of the electro-stimulation electrodes independently include an unbranched electrode structure or a branched electrode structure.

In some embodiments, the at least second pair of electrodes is the pair of impedance measurement electrodes. In such configurations each electrode within the pair of impedance measurement electrodes can include a plurality of electrode elements and can be configured as one half of a pair of interdigitated electrodes. In some embodiments, electrode of the pair of impedance monitoring electrodes has a same surface area.

In regards to extracellular recording configurations, the at least second pair of electrodes can be the extracellular recording electrode pair. Preferably, the extracellular recording electrode pair includes a recording electrode and reference electrode; however, two or more recording electrodes may be associated with one or more reference electrodes. Preferably each recording electrode has a diameter from about 10 µm to about 200 µm or from about 30 µm to about 100 µm. The ratio of the area of reference electrode to the area of recording electrode can vary but may be selected from the group consisting of 2 or more, 10 or more, 100 or more, 1,000 or more, and 10,000 or more. The reference electrode of the recording and reference electrode pair can have a branched or an unbranched structure.

In some embodiments at least one electrode is shared between the pair of electro-stimulation electrodes and the at least second electrode pair. In such configurations, the at least second electrode pair is the pair of impedance measurement electrodes. In other configurations the at least second electrode pair is the extracellular recording electrode pair.

In still further embodiments of the device the at least second electrode pair is the pair of impedance measurement electrodes, and device further includes the extracellular recording pair as a third pair of electrodes. In such configurations, at least one electrode can be shared between the pair of impedance measurement electrodes and the recording and reference electrode pair.

In another aspect of the invention a method for monitoring excitable cells is provided, which includes providing a system for electro-stimulating excitable cells and monitor impedance and/or extracellular potential of stimulated cells which has at least two pairs of electrodes; adding a sample of excitable cells to the device; electro-stimulating the excitable cells with electro-stimulation electrodes; and monitoring electro-stimulated cells through the at least second pair of electrodes. In some embodiments the excitable cells are cardiomyocytes or cardiomyocyte precursor cells. Electro-stimulation can be performed at a plurality of time intervals, optionally at regular time intervals.

When impedance monitoring, a pair of impedance monitoring electrodes can communicatively coupled to an impedance analyzer, thereby permitting the step of monitoring electro-simulated cells to include monitoring impedance of electro-stimulated cells. Preferably, impedance is monitored in millisecond time resolution. The methods may also include adding a compound suspected of affecting excitation contraction coupling of the excitable cells to the at least one well for analysis. The methods may include calculating and comparing an impedance-based parameter prior to and after adding the compound to identify whether a change occurs in the excitable cells in response to the compound. In some embodiments, the impedance-based parameter is compared between at least two different electro-stimulation intervals. Examples of suitable impedance-based parameter include an impedance measurement, a cell index calculated from the impedance measurement, and a cell change index calculated from the cell index. Preferably, the impedance based parameter is plotted as an impedance-based curve over time and the step of comparing the impedance-based parameter between at least two different electro-stimulation intervals includes comparing impedance-based curves between at least to different electro-stimulation intervals. In some embodiments, the excitable cells are added to each of at least two wells and the step of performing impedance measurements is performed for each of the at least two wells, the method can therefore further include adding a compound suspected of affecting excitation contraction coupling of the excitable cells to a first of the at least two wells to form a test well and adding a control to a second of the lease two wells to form a control well, and comparing an impedance-based parameter between the test well and control well. Again, suitable impedance-based parameters can be the impedance measurement, a cell index calculated from the impedance measurement, and a cell change index calculated from the cell index. Preferably, the impedance-based parameter is plotted as an impedance-based curve over time and the step of comparing the impedance-based parameter between the test well and control well includes comparing the impedance-based curve of the test well to the impedance based curve of the control well.

In some embodiments, the extracellular recording electrode pair is communicatively coupled to the an extracellular recording amplifier, and the step of monitoring electro-simulated cells includes extracellular recording of electro-stimulated cells. Preferably, the embodiments include plotting extracellular potential from the extracellular recording of electro-stimulated cells over time to form a field potential curve. Extracellular recording can be performed before and after the step of electro-stimulating the excitable cells.

In further embodiments, the method includes adding a compound suspected of affecting excitation contraction coupling of the excitable cells to the at least one well for extracellular recording. In such embodiments, extracellular potential of the excitable cells prior to and after adding the compound can be compared to identify changes in extracellular potential in response to the compound. Extracellular potential may be plotted over time to form a field potential curve for analysis.

In further embodiments, excitable cells are added to each of at least two wells and the step of performing extracellular recording measurements is performed for each of the at least two wells. In such instances, the method can include adding a compound suspected of affecting excitation contraction coupling of the excitable cells to a first of the at least two wells to form a test well and adding a control to a second of the lease two wells to form a control well, and comparing extracellular potential between the test well and control well. Extracellular recording can be performed before and after adding the compound.

In some embodiments, a pair of impedance monitoring electrodes are communicatively coupled to the impedance analyzer and the extracellular recording electrode pair is communicatively coupled to the extracellular recording amplifier, and the step of monitoring electro-stimulated cells includes impedance monitoring and extracellular recording of electro-stimulated cells. In some embodiments at least one electrode is shared between two pairs of electrodes selected from the group consisting of the pair of electro-stimulation electrodes and the pair of impedance monitoring electrodes, the pair of electro-stimulation electrodes and the extracellular recording electrode pair, and the pair of impedance monitoring electrodes and the extracellular recording electrode pair. In such configurations, the sharing of the electrode(s) is performed by switching communication to the at least one electrode.

In some embodiments the method include adding a compound suspected of affecting excitation contraction coupling of the excitable cells to the at least one well. Such methods may also include comparing an impedance-based parameter and extracellular field potential prior to and after adding the compound to identify whether a change occurs in the excitable cells in response to the compound. Preferably, the impedance-based parameter is selected from the group consisting of an impedance measurement, a cell index calculated from the impedance measurement, and a cell change index calculated from the cell index. In still further embodiments, the impedance based parameter is plotted as an impedance-based curve over time and the extracellular field potential is plotted as field potential over time and the step of comparing the impedance-based parameter and extracellular field potential between at least two different electro-stimulation intervals includes comparing impedance-based curves and comparing field potential curves between at least two different electro-stimulation intervals.

BRIEF DESCRIPTION OF THE DRAWINGS

FIG. 8F shows an overlay of an interval of ECR field potentials from each of FIGS. 8A-E.

FIG. 11F being an overlay of field potential curves from FIGS. 11A-E.

FIG. 12G is an overlay of FIGS. 12A-F)

In FIG. 13B, impedance and field potential are split in that the upper panel is impedance and the lower panel is field potential. FIG. 13C is an enlarged view showing a single interval and the relationship between impedance and field potential.

DETAILED DESCRIPTION OF PREFERRED EMBODIMENTS

Figure 1:
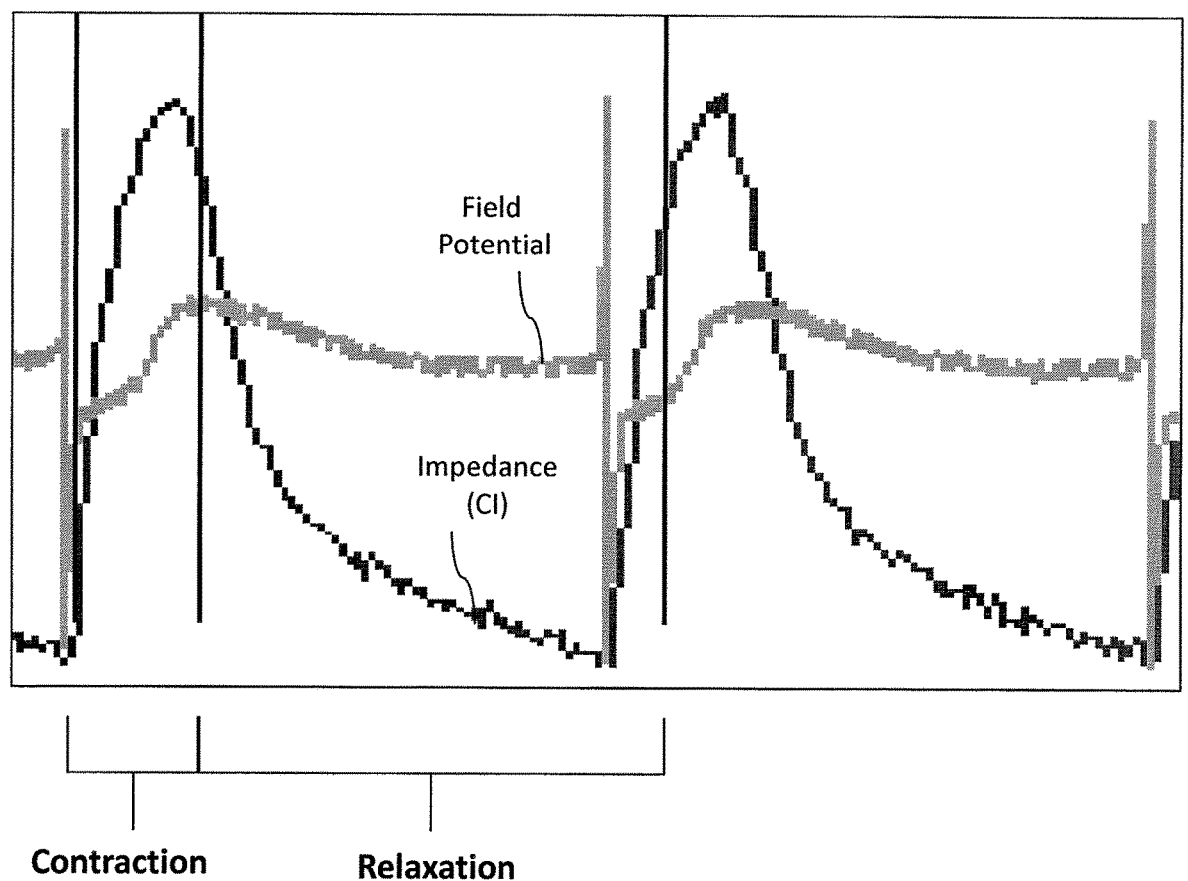
FIG. 1 is a schematic illustration showing a correlation of a cell index impedance parameter and field potential for a contraction-relaxation interval in a primary neonatal rat cardiomyocyte.

As an introduction, we describe label-free methods for electro-stimulating and monitoring excitable cells, such as cardiomyocytes, in vitro. It is an object of the invention to apply appropriate electro-stimulation signals for stimulating and/or pacing excitable cells, together with extracellular recording of cells, impedance monitoring of cells, or parallel impedance monitoring and extracellular recording cells using microelectrodes to non-invasively monitor cells. To this end, the devices, systems and methods allow the continuous monitoring of cardiomyocyte viability overtime and can monitor the interaction of compounds which ultimately result in promoting loss of cardiomyocyte viability. Further, the devices systems and methods permit high resolution monitoring of the beating cycle of a population of cardiomyocyte cells thus can detect changes in cell beating, such as shifts in contraction or relaxation that would be difficult to detect otherwise. As further introduction, an exemplary plot of the relationship between impedance and extracellular recording is shown in FIG. 1, where high resolution monitoring demonstrates that contraction and relaxation of cells, such as cardiomyocytes can be effectively monitored using an impedance-based approach and more preferably together with extracellular recording. In particular a peak in impedance (as measured in cell index) is followed by a peak in field potential. According changes in either impedance or extracellular recording provides insight as to changes occurring in the excitable cell population. Still further, by incorporating short term impedance monitoring with long term impedance monitoring the status excitable cell population can be further studied, An implication of this high resolution monitoring discussed herein is that impedance monitoring and extracellular recording can be used as a high throughput approach to screen for potential cardiotoxic affects of compounds. Further it also provides approaches for monitoring embryonic stem cell development into cardiomyocytes and implications associated with genetic knock outs and transgene expression at different developmental stages.

Definitions

For clarity of disclosure, and not by way of limitation, the detailed description of the invention is divided into the subsections that follow. Further, unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "biocompatible membrane or biocompatible surface" means a membrane or surface that does not have deleterious effects on cells, including the viability, attachment, spreading, motility, growth, cell division or cell beating.

As used herein, "biomolecular coating", "biological molecule coating" or "coated with a biomolecule" refers a coating on a surface that comprises a molecule that is a naturally occurring biological molecule or biochemical, or a biochemical derived from or based on one or more naturally occurring biomolecules or biochemicals. For example, a biological molecule coating can include an extracellular matrix component (e.g., fibronectin, collagens), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals.

An "organic compound coating" or a "coating having an organic compound) as used herein refers to a coating on a substrate that includes an organic compound. For example an organic compound may include a natural ligand or an agonist or an antagonist for a cell surface receptor.

An "electrode" is a structure having a high electrical conductivity, that is, an electrical conductivity much higher than the electrical conductivity of the surrounding materials, which in the present invention are typically nonconductive. An "extracellular recording electrode" or "recording electrode" or "ECR electrode" is such a structure used to detect electrical signal corresponding to extracellular field potential of the cell or cell population. For instance, a "recording electrode" may be used to monitor the extracellular field potential of a cardiomyocyte during the generation of membrane action potentials. A "reference electrode" is the complementary structure used to complete the electrical circuit during extracellular recording. An "impedance electrode", "impedance monitoring electrode", "impedance measurement electrode" or "impedance electrode structure" is a structure, such as an electrode, used for impedance monitoring. An "impedance electrode" may also operate as an extracellular recording electrode or electro-stimulation and thus may provide both impedance monitoring and extracellular recording measurements or both impedance monitoring and electro-stimulation, albeit at different time points.

As used herein, an "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike or branched projection of an interdigitated electrode structure. An electrode structure may have a plurality of electrode elements.

As used herein, a "unitary electrode structure" refers to a single electrode that is unbranched. That is, a "unitary electrode structure" does not include a plurality of electrode elements. For example, an unitary electrode structure may be of a circle, a square or other geometry.

As used herein, a "pair of electrodes" or "electrode pair" is two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Non-limiting examples of electrode structure units are interdigitated electrode structure units and concentric electrode structure units.

As used herein "electrode bus" is a portion of an electrode that connects individual electrode elements or substructures. An electrode bus provides a common conduction path from individual electrode elements or individual electrode substructures to another electrical connection. In the devices of the present invention, an electrode bus can contact each electrode element of an electrode structure and provide an electrical connection path to electrical traces that lead to a connection pad.

As used herein "electrode traces" or "electrically conductive traces" or "electrical traces", are electrically conductive paths that extend from electrodes or electrode elements or electrode structures toward one end or boundary of a device or apparatus for connecting the electrodes or electrode elements or electrode structures to a electro-stimulation power source, an analyzer or amplifier, such as an impedance analyzer or amplifier, a voltage amplifier and the like. Electrical communication of electro-stimulation electrodes, impedance electrodes or extracellular recording electrodes typically involves connection to a connection pad using an "electrode trace."

As used herein "connection pad" is an area on an apparatus or a device of the present invention which is electrically connected to at least one electrode or all electrode elements within at least one electrode structure on an apparatus or a device and which can be operatively connected to external electrical circuits (e.g., an impedance measurement circuit or a signal source or an extracellular voltage signal amplifier). The electrical connection between a connection pad and an impedance measurement circuit, an extracellular recording circuit or a signal source can be direct or indirect, through any appropriate electrical conduction means such as leads or wires. Such electrical conduction means may also go through electrode or electrical conduction paths located on other regions of the apparatus or device.

As used herein "Interdigitated" means having projections coming one direction that interlace with projections coming from a different direction in the manner of the fingers of folded hands (with the caveat that interdigitated electrode elements preferably do not contact one another).

As used herein, "at least two electrodes fabricated on the substrate" means that the at least two electrodes are fabricated or made or produced on the substrate. The at least two electrodes can be on the same side of the substrate or on the different side of the substrate. The substrate may have multiple layers, the at least two electrodes can be either on the same or on the different layers of the substrate.

As used herein, "at least two electrodes fabricated to a same plane of the substrate" means that, if the nonconducting substrate has multiple layers, the at least two electrodes are fabricated to the same layer of the substrate.

As used herein, "an electrode positioned on a different plane" refers to the positioning of an electrode, typically an external electrode or reference electrode, above, below or along a different surface angle than that which it is compared. An "electrode positioned on a different plane" may be parallel to that of the first.

As used herein, "the . . . electrodes (or electrode structures) have substantially the same surface area" means that the surface areas of the electrodes referred to are not substantially different from each other, so that the impedance change due to cell attachment or growth on any one of the electrodes (or electrode structures) referred to will contribute to the overall detectable change in impedance to a same or similar degree as the impedance change due to cell attachment or growth on any other of the electrodes (or electrode structures) referred to. In other words, where electrodes (or electrode structures) have substantially the same surface area, any one of the electrodes can contribute to overall change in impedance upon cell attachment or growth on the electrode. In most cases, the ratio of surface area between the largest electrode and the smallest electrode that have "substantially the same surface area" is less than 10. Preferably, the ratio of surface area between the largest electrode and the smallest electrode of an electrode array is less than 5, 4, 3, 2, 1.5, 1.2 or 1.1. More preferably, the at least two electrodes of an electrode structure have nearly identical or identical surface area.

As used herein, "the device has a surface suitable for cell attachment or growth" means that the electrode and/or non-electrode area of the apparatus has appropriate physical, chemical or biological properties such that cells of interest can viably attach on the surface and new cells can continue to attach, while the cell culture grows, on the surface of the apparatus. However, it is not necessary that the device, or the surface thereof, contain substances necessary for cell viability or growth. These necessary substances, e.g., nutrients or growth factors, can be supplied in a medium. Preferably, when a suspension of viable cardiomyocytes, neuron cells, muscle cells or other excitable cells or other adherent cells such as epithelial cells or endothelial cells is added to the "surface suitable for cell attachment" when at least 50% of the cells are adhering to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

As used herein, "detectable change in impedance between or among said electrodes" (or "detectable change in impedance between or among the electrode structures") means that the impedance between or among the electrodes (or electrode structures) would have a significant change that can be detected by an impedance analyzer or impedance measurement circuit when cells attach on the electrode surfaces. The impedance change refers to the difference in impedance values when cells are attached to the electrode surface and when cells are not attached to the electrode surface, or when the number, type, activity, adhesiveness, or morphology of cells attached to the electrode-comprising surface of the apparatus changes. In most cases, the change in impedance is larger than 0.1% to be detectable. Preferably, the detectable change in impedance is larger than 1%, 2%, 5%, or 8%. More preferably, the detectable change in impedance is larger than 10%. Impedance between or among electrodes is typically a function of the frequency of the applied electric field for measurement. "Detectable change in impedance between or among the electrodes" does not require the impedance change at all frequencies being detectable. "Detectable change in impedance between or among said electrodes" only requires a detectable change in impedance at any single frequency (or multiple frequencies). In addition, impedance has two components, resistance and reactance (reactance can be divided into two categories, capacitive reactance and inductive reactance). "Detectable change in impedance between or among said electrodes" requires only that either one of resistance and reactance has a detectable change at any single frequency or multiple frequencies. In the present application, impedance is the electrical or electronic impedance. The method for the measurement of such impedance is achieved by, (1) applying a voltage between or among the electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. Measurement of such electric impedance is an electronic or electrical process that does not involve the use of any reagents.

As used herein, "arranged in a row-column configuration" means that, in terms of electric connection, the position of an electrode, an electrode array or a switching circuit is identified by both a row position number and a column position number.

As used herein, "each well contains substantially same number . . . of cells" means that the lowest number of cells in a well is at least 50% of the highest number of cells in a well. Preferably, the lowest number of cells in a well is at least 60%, 70%, 80%, 90%, 95% or 99% of the highest number of cells in a well. More preferably, each well contains an identical number of cells.

As used herein, "each well contains . . . same type of cells" means that, for the intended purpose, each well contains same type of cells; it is not necessary that each well contains exactly identical type of cells. For example, if the intended purpose is that each well contains mammalian cells, it is permissible if each well contains same type of mammalian cells, e.g., human cells, or different mammalian cells, e.g., human cells as well as other non-human mammalian cells such as mice, goat or monkey cells, etc.

As used herein, "each well contains . . . serially different concentration of a test compound" means that each well contains a test compound with a serially diluted concentrations, e.g., an one-tenth serially diluted concentrations of 1 M, 0.1 M, 0.01 M, etc.

As used herein, "dose-response curve" means the dependent relationship of response of cells on the dose concentration of a test compound. The response of cells can be measured by many different parameters. For example, a test compound is suspected to have cytotoxicity and cause cell death. Then the response of cells can be measured by percentage of non-viable (or viable) cells after the cells are treated by the test compound. Plotting this percentage of non-viable (or viable) cells as a function of the dose concentration of the test compound constructs a dose response curve. In the present application, the percentage of non-viable (or viable) cells can be expressed in terms of measured impedance values, or in terms of cell index derived from impedance measurement, or in terms of cell change indexes. For example, for a give cell type and under specific cellular physiological condition (e.g., a particular cell culture medium), cell index can be shown to have a linear correlation or positive correlation with the number of viable cells in a well from which cell index was derived from the impedance measurement. Thus, in the present application, one can plot cell index as a function of the dose concentration of the test compound to construct a "dose-response curve". Note that, generally, cell index not only correlate with the number of viable cells in the wells but also relate to the cell morphology and cell attachment. Thus plotting cell index versus dose concentration provides information not only about number of cells but also about their physiological status (e.g. cell morphology and cell adhesion). Furthermore, an important advantage offered by the system and devices of the present invention is that in a single experiment, one can obtain "dose-response curves" at multiple time points since the system allows for the continuous monitoring of cells and provides impedance measurement at many time points over a time range as short as a few minutes to as long as days or weeks.

As used herein, "sample" refers to anything which may contain a moiety to be isolated, manipulated, measured, quantified, detected or analyzed using apparatuses, microplates or methods in the present application. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

A "compound" or "test compound" is any compound whose activity or direct or indirect effect or effects on cells is investigated in any assay. A test compound can be any compound, including, but not limited to, a small molecule, a large molecule, a molecular complex, an organic molecule, an inorganic molecule, a biomolecule or biological molecule such as but not limited to a lipid, a steroid, a carbohydrate, a fatty acid, an amino acid, a peptide, a protein, a nucleic acid, or any combination thereof. A test compound can be a synthetic compound, a naturally occurring compound, a derivative of a naturally-occurring compound, etc. The structure of a test compound can be known or unknown. In one application of the present invention, a compound is capable of, or is suspected of, effecting cell adhesion or cell spreading. In another application of present invention, a compound is capable of, or is suspected of, stimulating or inhibiting cell adhesion or cell spreading. In still another application, a compound is capable of, or is suspected of, interacting with an ion channel. In still another application, a compound is capable of, or is suspected of, modulating cardiomyocyte excitation contraction coupling or beating. In still another application, a compound is capable of, or is suspected of, interacting with cells (for example, binding to cell surface receptor, or inhibiting certain intracellular signal transduction pathway, or activating cells).

A "known compound" is a compound for which at least one activity is known. In the present invention, a known compound preferably is a compound for which one or more direct or indirect effects on cells is known. Preferably, the structure of a known compound is known, but this need not be the case. Preferably, the mechanism of action of a known compound on cells is known, for example, the effect or effects of a known compound on cells can be, as nonlimiting examples, effects on cell beating, cell viability, cell adhesion, apoptosis, cell differentiation, cell proliferation, cell morphology, cell cycle, IgE-mediated cell activation or stimulation, receptor-ligand binding, cell number, cell quality, cell cycling, cell adhesion, cell spreading, etc.

As used herein "Cell Index" or "CI" is a parameter that can derived from measured impedance values and that can be used to reflect the change in impedance values. There are a number of methods to derive or calculate Cell Index. The details of the method for calculating Cell Index, Normalized Cell Index, Delta Cell Index and cell change index can be found in U.S. patent application Ser. No. 10/705,447, filed on Nov. 10, 2003; U.S. patent application Ser. No. 10/705,615, filed on Nov. 10, 2003; U.S. patent application Ser. No. 10/987,73, filed on Nov. 12, 2004; U.S. patent application Ser. No. 11/055,639, filed on Feb. 9, 2005; U.S. patent application Ser. No. 11/198,831, filed on Aug. 4, 2005; U.S. patent application Ser. No. 11/197,994, filed on Aug. 4, 2005; U.S. patent application Ser. No. 11/235,938, filed on Sep. 27, 2005, all of them are incorporated here by reference.

A "Normalized Cell Index" at a given time point is calculated by dividing the Cell Index at the time point by the Cell Index at a reference time point. Thus, the Normalized Cell Index is 1 at the reference time point. Generally, for an assay involving treatment of the cells with compounds or with other bio-manipulation of the cells, the reference time point is the last time point for impedance measurement before the treatment of the cells.

A "delta cell index" at a given time point is calculated by subtracting the cell index at a standard time point from the cell index at the given time point. Thus, the delta cell index is the absolute change in the cell index from an initial time (the standard time point) to the measurement time.

A "Cell Change Index" or "CCI" is a parameter derived from Cell Index and "CCI" at a time point is equal to the $1^{st}$ order derive of the Cell Index with respect to time, divided by the Cell Index at the time point. In other words, CCI is calculated as $$CCI(t) = \frac{dCI(t)}{CI(t) \cdot dt}.$$

As used herein "extracellular recording" refers to measuring, monitoring and/or recording of electric potential difference between two electrodes typically caused by ionic movement or ionic current through the media or solution due to charge fluctuations across ion channels in a cell or in a group of cells. The cells are in the media or the solution. In contrast to intracellular recording where the recording electrodes are placed inside a cell through the cell membrane, the extracellular recording electrodes are located outside of the cells.

Devices and Systems for Electro-Stimulation and Measurement of Excitable Cells

Provided herein are devices and systems that permit the electro-stimulation as well as extracellular recording and/or impedance monitoring of cells. In particular, an exemplary device includes at least one well, each well having a bottom having a nonconductive substrate, the substrate having a surface suitable for attachment of excitable cells; a pair of electro-stimulation electrodes positioned on the substrate within the at least one well and configured to electro-stimulate the excitable cells; and at least a second pair of electrodes positioned within the at least one well. The at least second pair of electrodes can be a pair of impedance monitoring electrodes or an extracellular recording electrode pair. In some embodiments, the second pair of electrodes is the pair of impedance monitoring electrodes and the extracellular recording pair is provided as a third electrode pair. The pair of impedance monitoring electrodes are configured to measure cell-substrate impedance of cells attached to the substrate, and the extracellular recording electrode pair are configured to measure extracellular potential of cells attached to the substrate. Accordingly, the device permits the electro-stimulation of excitable cells, such as cardiomyocytes while various embodiments permit impedance monitoring, extracellular recording or both impedance monitoring and extracellular recording of excitable cells.

The above is accomplished at least in part because while the substrate has a surface suitable for attachment of excitable cells, it has been found that the attachment of excitable cells on the substrate provides a suitable form for measuring extracellular potential through the extracellular recording electrode pair, and measuring cell-substrate impedance through the pair of impedance monitoring electrodes, and still further that the attached excitable cells can be electro-stimulated or paced by electro-stimulation when appropriate electrical signals are delivered to the pair of electro-stimulation electrodes. Thus, by providing a device that permits alternating electro-stimulation coupled with cell detection or measurement techniques the cell culture can maintain a regular beating interval to test the cardiotoxic affects of various compounds or monitor the development of cardiomyocyte precursor cells to cardiomyocytes.

Preferably, the device includes one or more fluid-impermeable receptacles which serve as fluid containers or wells. Such receptacles may be reversibly or irreversibly attached to or formed within the substrate or portions thereof (such as, for example, wells formed as in a microtiter plate). Suitable fluid container materials comprise plastic, glass, or plastic coated materials such as a ceramic, glass, metal, etc. Descriptions and disclosure of devices that comprise fluid containers can be found in U.S. Pat. No. 7,470,533, herein incorporated by reference for all disclosure of fluid containers and fluid container structures that can engage a substrate comprising electrodes for impedance measurements, including their dimensions, design, composition, and methods of manufacture.

In some embodiments, commercial tissue culture plates can be adapted to fit the substrate. Bottomless plates may also be custom-made to preferred dimensions. The device may have any number of wells as desired for the particular experiment. For instance, the device may have 1 well, 2 wells, 3 wells, 6 wells, 8 wells, 12 wells, 24 wells, 36 wells, 96 wells, 384 wells, 1536 wells or the like. Preferably, well diameters are from about 1 millimeter to about 20 millimeters, more preferably from about 2 millimeters to about 8 millimeters at the bottom of the well (the end disposed on the substrate). The wells can have a uniform diameter or can taper toward the bottom so that the diameter of the container at the end in contact with the substrate is smaller than the diameter of the opposing end.

The surface of the substrate is suitable for cell attachment and optionally growth. Preferably, the nonconducting substrate is planar, and is flat or approximately flat. The substrate may be constructed from a variety of nonconductive materials known in the present art, including, but not limited to, silicon dioxide on silicon, silicon-on-insulator (SOI) wafer, glass (e.g., quartz glass, lead glass or borosilicate glass), sapphire, ceramics, polymer, fiber glass, plastics, e.g., polyimide (e.g. Kapton, polyimide film supplied by DuPont), polystyrene, polycarbonate, polyvinyl chloride, polyester, polypropylene and urea resin. Preferably, the substrate is biocompatible with excitable cells such as cardiomyocytes; however, materials that are not biocompatible can be made biocompatible by applying a biocompatible or biomolecular coating with a suitable material, such as a biocompatible polymer or the like. Further, attachment or growth along the substrate or electrodes may be enhanced by pre-coating the substrate with a protein or compound that facilitates attachment or growth. Such compounds may be chosen according to techniques known in the cellular biology arts; however, in some embodiments fibronectin is effective. Alternatively, the substrate may be chemically modified to display reactive groups or binding moieties such as adhesion molecules that enhance cell attachment, particularly ES cells that are cardiomyocyte precursor cells or cardiomyocytes.

To improve efficiency of production, electrodes of the invention may be applied to the substrate followed by joining the electrode applied substrate to a plate of bottomless wells or may be applied to a well already having the substrate as a bottom. Electrodes may be formed from larger sheets of conductive metal, such as via laser ablation of a metallic film and may be applied directly to the substrate. Alternatively, electrodes may be printed on the substrate using printing techniques such as those similar to ink-jet printing where a conductive fluid having ultraviolet (UV) curable monomers, polymers or compounds is printed on the substrate, then a light source is applied to cure the applied conductive fluid to form electrodes. The skilled artisan will appreciate that conductive material may be applied directly to a planar substrate or may be inserted into grooves laser ablated or formed into the substrate surface. A glue, such as a UV curable glue, can be applied between the substrate and electrode or above the electrode for added security. Further, when applying conductive fluids, it may be preferred to apply a mask prior to applying the fluid to further define the electrode area.

Figure 2A:
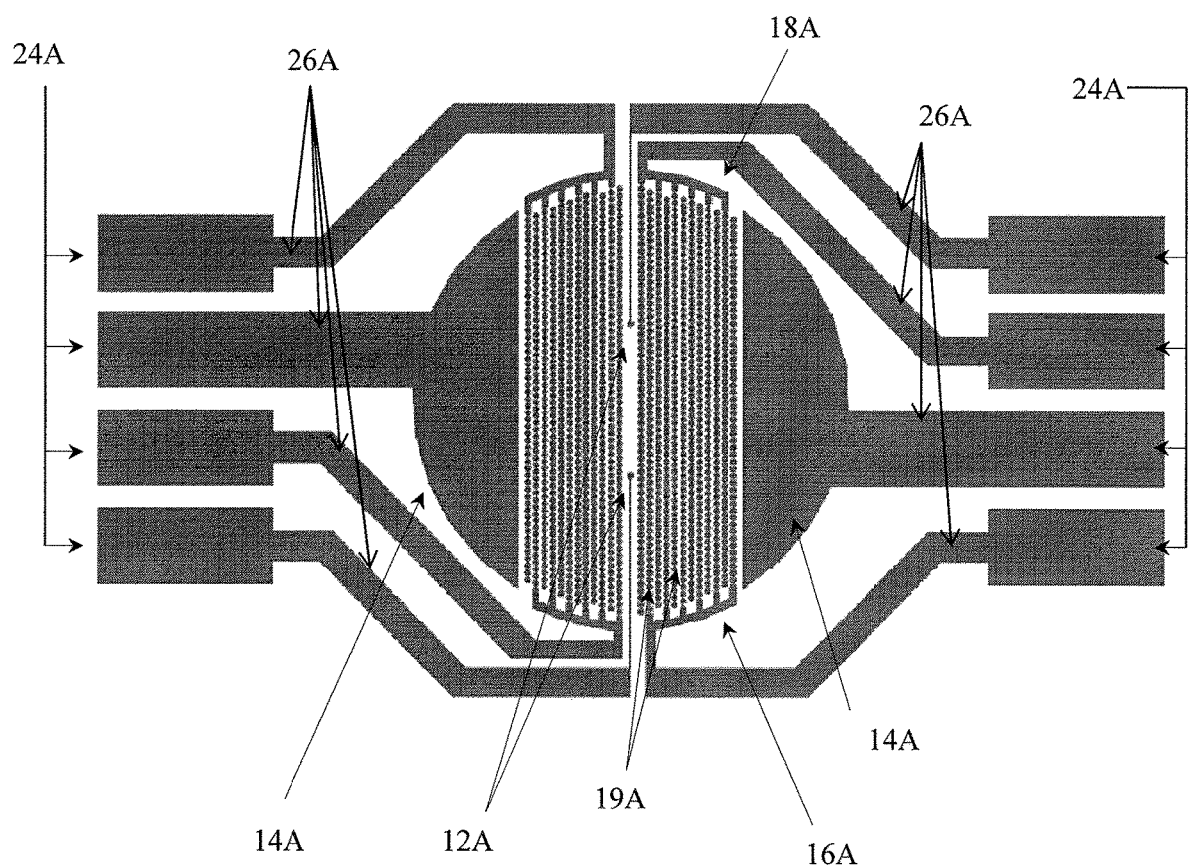
FIGS. 2A-D depict different configurations of electrode arrays 10A-D that can perform electro-stimulation, impedance measurement and extracellular recording.
Figure 2B:
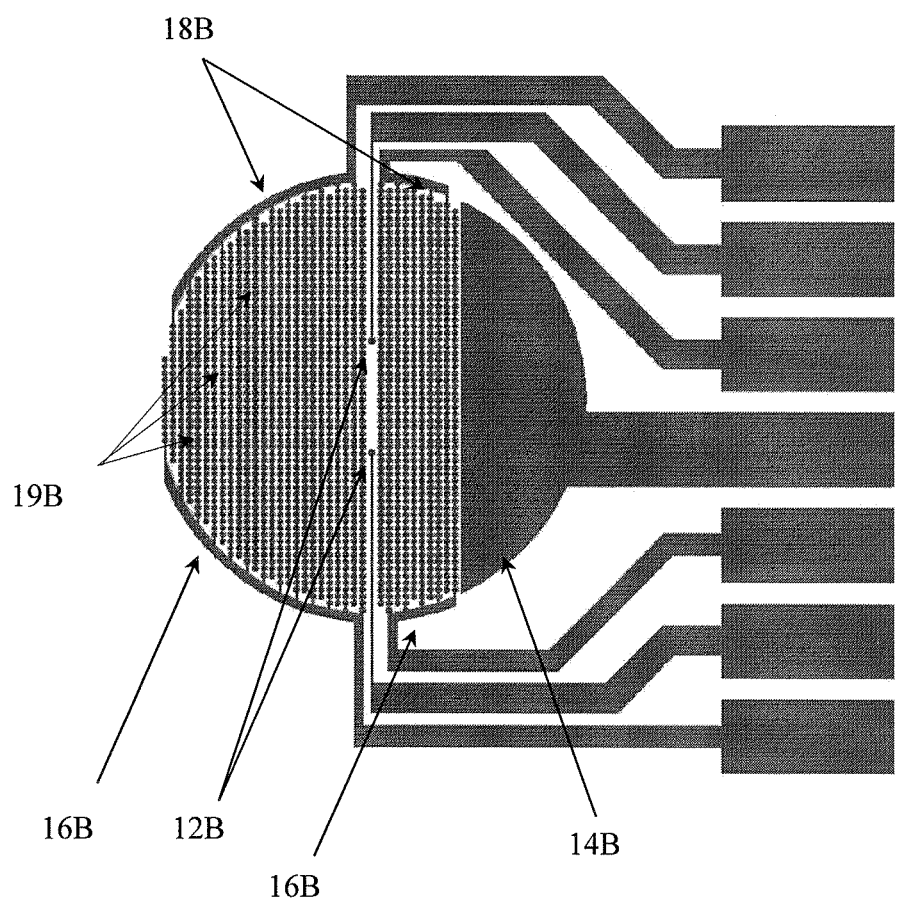

Examples of suitable electrode configurations are shown in FIGS. 2A-2D, which depict examples where electrodes are shared between different functional pairs, in particular, where two electrodes from the pair of electro-stimulation electrodes are shared with a pair of impedance monitoring electrodes. Using this technical approach the pair of impedance monitoring electrodes can be used for electro-stimulating the excitable cells when not measuring impedance. Thus, the electrode arrays provide electrode structures for cell electro-stimulation, cell-impedance measurement and extra-cellular recording, as designed on a non-conductive substrate associated with a single well. Turning in more detail to FIG. 2A an exemplary electrode array 10A includes an extracellular recording electrode pair formed from two round-circular extra-cellular recording electrodes 12A positioned at about the middle of the entire array 10A and a unitary one-piece reference electrode 14A positioned at opposing ends of the array 10A. A pair of interdigitated electrodes (16A, 18A) formed from a plurality of electrode elements 19A function to electro-stimulate a cell population when switched to a electro-stimulation mode and function to measure cell substrate impedance when switched to an impedance monitoring mode. These shared electro-stimulation/impedance monitoring electrodes 16A, 18A are shown in a branched configuration. More specifically, a plurality of electrode elements 19A of each electrode structure 16A, 18A are shown having a circle on line configuration.

As a nonlimiting example, particular specifications shown in FIG. 2A are that the diameter of each of the two the recording electrodes 12A is 100 µm; the distance between two recording electrodes 12A is 2.98 mm; the diameter of circles in the circle-on-line electrode elements 19A is 90 µm, the center-to-center distance between two adjacent circle-on-line electrode elements 19A is 110 µm; and the gap between two shared impedance/electro-stimulation electrodes 16A, 18A and covering the recording electrodes 12A is ~290 µm. Each of the electrodes 12A, 14A, 16A, 18A are connected to a connection pad 26A via an electrical trace 26A A variety of other configurations have been developed including electrode structures for cell electro-stimulation, cell-impedance measurement and extracellular recording of cells, as designed on a non-conductive substrate associated with a single well. For example, in FIG. 2B, each electrode array 10B includes two round-circular extracellular recording electrodes 12B and a single unitary one-piece reference electrode 14B. Electrode structures 16B, 18B are used for both electro-stimulation and cell impedance monitoring albeit at different time points by electronic switching. In this exemplary embodiment, the diameter of each recording electrode 12B is 60 um; the distance between two recording electrodes 12B is 2 mm; the diameter of circles in the circle-on-line electrode elements 19B is 90 um, the center-to-center distance between two adjacent circle-on-line electrode elements 19B is 110 um; the gap between two impedance-electrode-structures 16B, 18B and covering the recording electrodes 12B is 290 um.

Figure 2C:
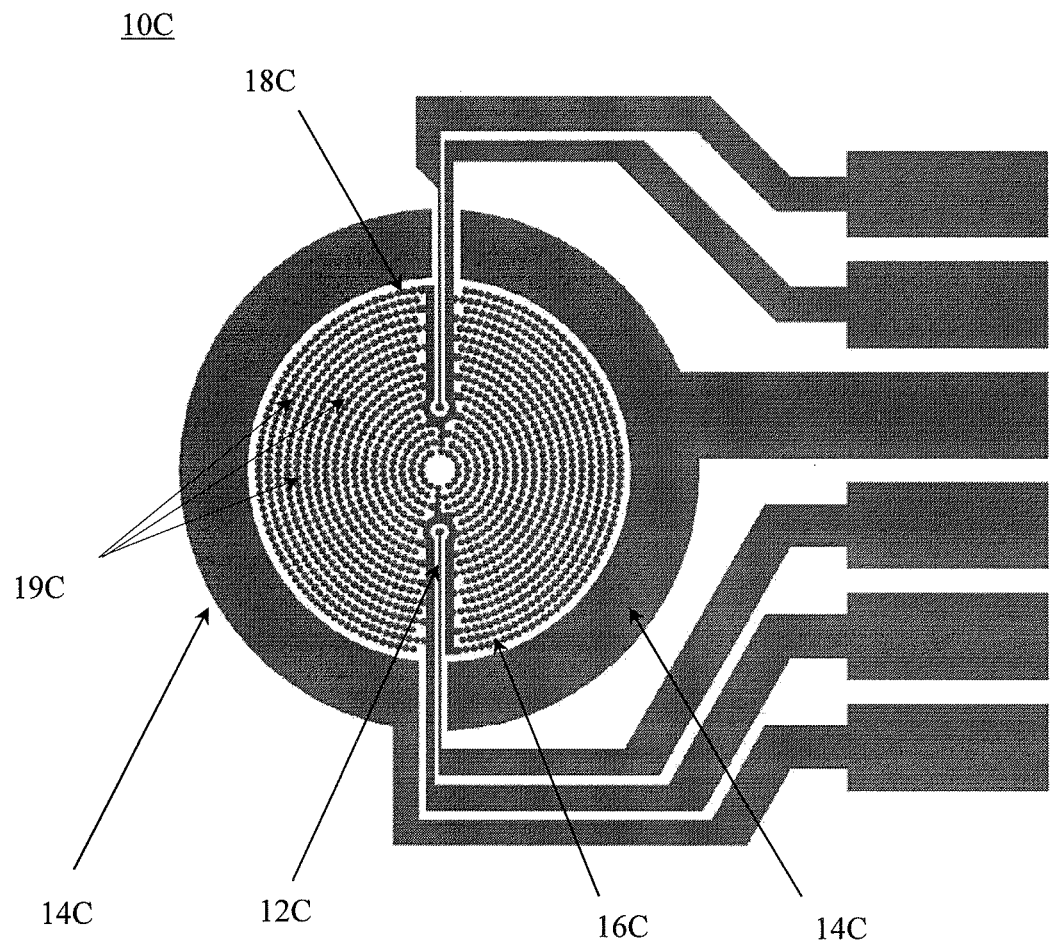

Still another configuration is shown in FIG. 2C, where each electrode array 10C is configured on a non-conductive substrate associated with a single well. The electrode array 10C includes a round-circular extra-cellular recording electrode 12C and a unitary one-piece reference electrode 14C. Electrode structures 16C, 18C perform both impedance measurement and electro-stimulation of cells at different time points by electronic switching. In this example, a plurality of circle-on-circular-line electrode elements 19C form interdigitated electrode structures 16C, 18C. In this exemplary embodiment, the diameter of the recording electrodes 12C is 80 um; the distance between two recording electrodes 12C is 1.44 mm; the diameter of circles in the circle-on-line electrode elements 19C is 90 um, the center-to-center distance between two adjacent circle-on-line electrode elements 19C is 110 um.

Figure 2D:
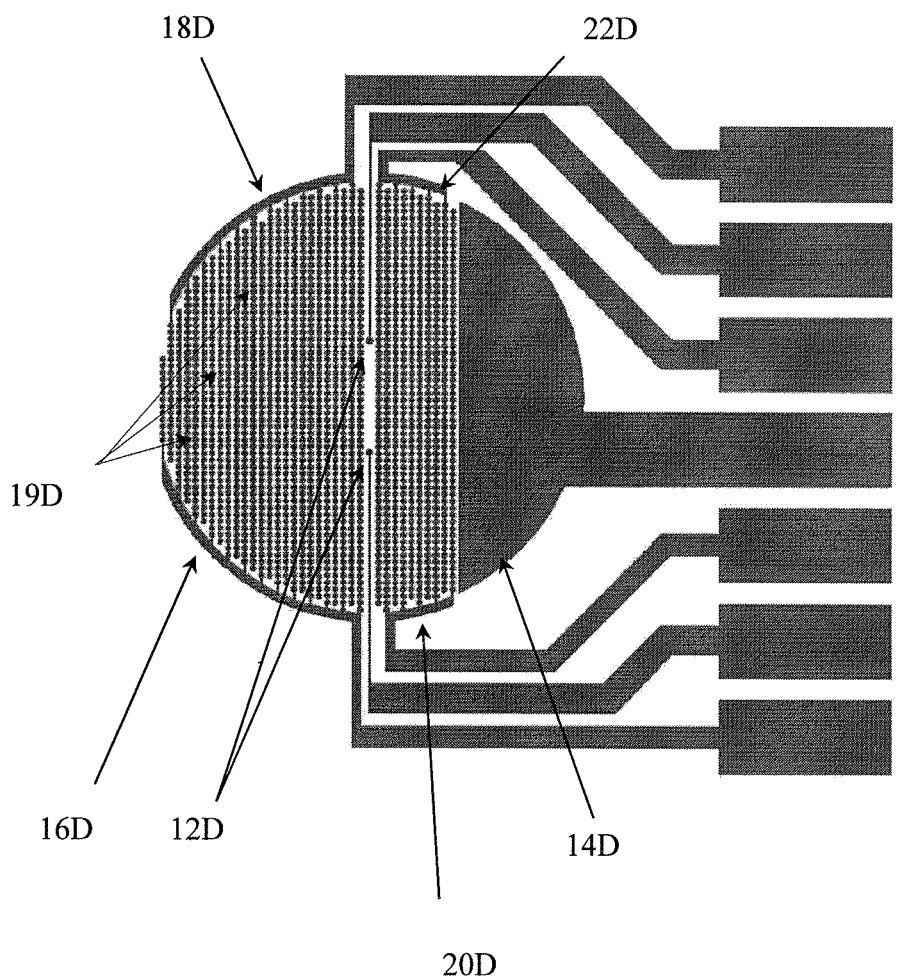

Still another configuration is shown in FIG. 2D, where an electrode array 10D includes two round-circular extra-cellular recording electrodes 12D and a single unitary one-piece reference electrode 14D. Electrode structures 16D, 18D are used for cell impedance monitoring. Electrode Structures 20D, 22D are used for electro-stimulation and for cell impedance monitoring. In this exemplary embodiment, the diameter of each recording electrode 12D is 60 um; the distance between two recording electrodes 12D is 2 mm; the diameter of circles in the circle-on-line electrode elements 19D is 90 um, the center-to-center distance between two adjacent circle-on-line electrode elements 19D is 110 um; the gap between two impedance-electrode-structures 16D, 22D and covering the recording electrodes 12D is ~290 um.

In regards to the device generally, configurations including two or more wells, preferably electrodes within each well of the device are individually addressed, meaning that electrical traces and connection pads of the arrays are configured such that an array can be connected to its power source, impedance amplifier or extracellular recording amplifier independent of the operation of an array in a neighboring well and thus each well can operate using different electro-stimulation intervals, perform different measurements and the like without adversely affecting neighboring wells.

Electrical traces of conductive material used to connect each of the electrodes to a corresponding connection pad can be fabricated of any electrically conductive material. The traces can be localized to the surface of the substrate, and can be optionally covered with an insulating layer. Alternatively the traces can be disposed in a second plane of the substrate.

Turning to the pair of electro-stimulation electrodes generally, the electrodes may be provided in a variety of shapes and configurations so long as the configuration permits electro-stimulation. Electro-stimulation can be accomplished using a variety of different waveforms such as rectangular, ramp, sinusoidal signals and the like. Either uni-polarity or bi-polarity signals can be used, with signal amplitude ranging from −2.5 V to +2.5 V. When pacing cardiomyocytes electrical signal from between 1 V-2V was preferred while electrical signal between about 1.1-1.3V was most preferred. In preferred embodiments, the electro-stimulation voltage can be controlled at voltage resolutions up to 2 mV. Maximum frequency of the stimulation signals could be up to 50 kHz.

Preferably, each of the pair of electro-stimulation electrodes of an electrode array is connected to a separate connection pad, which is preferably located at the edge of the substrate. Connecting the pair of electro-stimulation electrodes to the connection pads can be performed by applying electrical traces of conductive material therebetween. This facilitates connection to a suitable power source by providing an interface at which the power source can connect. Connection to the connection pads is generally performed through the use of electrically conductive pins, clips or the like.

One or more electro-stimulation electrodes can be shared with either the extracellular recording electrode pair or the pair of impedance monitoring electrodes by timing the switching between the power source that delivers the electro-stimulation signal through the electro-stimulation electrodes and the extracellular recording amplifier or the impedance analyzer.

Turning now to the extracellular recording electrode pair generally, extracellular recording is conducted by amplifying and recording electrical voltage signals between a recording electrode(s) and reference electrode(s). Such electrical voltages are induced on the electrodes as a result of ionic current or movement through cell culture media or solution supporting the cells during the experiment as a result of opening and/or closing of different ion channels across cell membrane during the action potential duration. In order to achieve improved consistency and reproducibility of the recorded voltage signals, it is desirable to minimize the contribution of any electrical signal from the reference electrode to the recorded voltage signals and to ensure that the majority, if not all, of the recording voltage signals are derived from that on the recording electrode. Thus, generally, it is desirable and it is recognized for the reference electrodes to have small electrode impedances. The small electrode impedance is achieved by using reference electrodes with large effective surface areas by increasing the ratio of the surface area of the reference electrodes to that of recording electrode by a factor of a hundred, even thousands of times. For example, FIG. 2A shows a schematic representation of such electrode pairs placed on a non-conductive substrate, including a small area recording electrode 12A and a much larger area reference electrode 14A. As shown throughout FIGS. 2A-2D, preferably the reference electrode 14 is positioned towards the perimeter of the electrode array 10; however, it must not physically contact the recording electrode 12.

The reference electrode generally, can be a unitary or unbranched electrode and may be of a simple geometry such as a circle, a square and the like. In other embodiments, the reference electrode has a branched configuration, which may result in a large surface for the reference electrode. In some embodiments, the ratio of the surface area of the reference electrode to that of the recording electrode is more than 2. In other embodiments, the ratio of the surface area of the reference electrode to that of the recording electrode is 10 or more than 10. In still other embodiments, the ratio of the surface area of the reference electrode to that of the recording electrode is 100 or more than 100. In other embodiments the ratio of the surface area of the reference electrode to that of the recording electrode is 1000 or more than 1000. In other the ratio of the surface area of the reference electrode to that of the recording electrode is 10,000 or more than 10,000.

While it is preferable to simultaneously measure impedance and perform extracellular recording, in some embodiments one or both electrodes of the pair of impedance measurement electrodes is shared with the extracellular recording electrode pair. When using impedance electrodes in the form of interdigated electrode structures having a plurality of electrode elements, typically the shared electrode would be used as a reference electrode in the extracellular recording electrode pair. This can be accomplished when the surface area of the impedance monitoring electrode(s) is sufficiently larger than the surface area of the recording electrode to act as a reference electrode. The skilled artisan will appreciate that by electrically switching a pair of interdigitated impedance electrodes from impedance monitoring to function as a single reference electrode, the surface area ratio of the combined interdigitated electrodes to recording electrode would substantially increase and thus may be preferable in some instances. Further, it is also possible, though not preferred to utilize an impedance measurement electrode as a recording electrode when the reference electrode is sufficiently larger than the impedance measurement electrode. While not preferred this approach is more likely when using impedance measurement electrode configurations having a small working electrode and large counter electrode as previously detailed in the art.

Turning now to the pair of impedance monitoring electrodes themselves, each pair includes two or more electrode structures that are constructed to have dimensions and spacing such that they can, when connected to an impedance analyzer, operate as a unit to generate an electrical field in the region of spaces around the impedance electrode structures. Preferably the electric field is substantially uniform across the pair of impedance electrodes. In preferred embodiments, the pair of impedance electrodes includes two impedance measurement electrode structures, each of which includes multiple electrode elements, or substructures, which branch from the electrode structure. In preferred embodiments, the electrode structures in each pair have substantially the same surface area.

Each of the two complementary impedance monitoring electrode structures of a pair connect to a separate connection pad that is preferably located at the edge of the substrate. In some embodiments, the array includes two pairs of impedance monitoring electrodes separated by a recording electrode region where one or two recording electrodes are positioned on a same plane of the substrate. In such embodiments it is preferred that each electrode structure be assigned to a separate connecting pad however the pairs could be electrically joined such as by connection at a shared connection pad or through an electronic switch.

In some embodiments, for each of two or more pairs of impedance monitoring electrodes in two or more wells, a first of the two impedance monitoring electrode structures is connected to one of two or more connection pads, and the second of the two impedance monitoring electrode structures is connected to another of the two or more connection pads.

Preferably, each pair of impedance monitoring electrodes of the device has an approximately uniform electrode resistance distribution across the entire pair of electrodes. By "uniform resistance distribution across the pair" is meant that when a measurement voltage is applied across the electrode structures of pair of impedance measurement electrodes, the electrode resistance at any given location of the pair is approximately equal to the electrode resistance at any other location on the pair. Preferably, the electrode resistance at a first location on the pair and the electrode resistance at a second location on the pair does not differ by more than 30%. More preferably, the electrode resistance at a first location on the pair and the electrode resistance at a second location on the same pair does not differ by more than 15%. Even more preferably, the electrode resistance at a first location on the pair and a second location on the same pair does not differ by more than 5%. More preferably yet, the electrode resistance at a first location on the pair and a second location on the same pair does not differ by more than 2%.

Preferred arrangements for electrode elements that form the pair of impedance monitoring electrodes and gaps between the electrodes and electrode buses in a given pair are used to allow all cells, no matter where they land and attach to the pair of impedance measurement electrodes to contribute similarly to the total impedance change measured for the pair. Thus, it is desirable to have similar electric field strengths at any two locations within any given pair of impedance measurement electrodes when a measurement voltage is applied to the pair. At any given location of the pair, the field strength is related to the potential difference between the nearest point on a first electrode structure of the pair and the nearest point on a second electrode structure of the pair. It is therefore desirable to have similar electric potential drops across the electrode elements and across the electrode buses of a given pair. Based on this requirement, it is preferred to have an approximately uniform electrode resistance distribution across the whole pair where the electrode resistance at a location of interest is equal to the sum of the electrode resistance between the nearest point on a first electrode structure (that is the point on the first electrode structure nearest the location of interest) and a first connection pad connected to the first electrode structure and the electrode resistance between the nearest point on a second electrode structure (that is the point on the first electrode structure nearest the location of interest) and a second connection pad connected to the second electrode structure.

Achieving an approximately uniform distribution across the pair of impedance measurement electrodes can be achieved, for example, by having electrode structures and electrode buses of particular spacing and dimensions (lengths, widths, thicknesses and geometrical shapes) such that the resistance at any single location on the pair is approximately equal to the resistance at any single other location on the pair. In most embodiments, the electrode elements (or electrode structures) of a given pair will have even spacing and be of similar thicknesses and widths, the electrode buses of a given pair will be of similar thicknesses and widths, and the electrode traces leading from a given pair to a connection pad will be of closely similar thicknesses and widths. Thus, in these preferred embodiments, a pair of electrode structures is designed such that the lengths and geometrical shapes of electrode elements or structures, the lengths and geometrical shapes of electrode traces, and the lengths and geometrical shapes of buses allow for approximately uniform electrode resistance distribution across the pair.

In some preferred embodiments of impedance measurement configurations, electrode structures comprise multiple electrode elements, and each electrode element connects directly to an electrode bus. Electrode elements of a first electrode structure connect to a first electrode bus, and electrode elements of a second electrode structure connect to a second electrode bus. In these embodiments, each of the two electrode buses connects to a separate connection pad via an electrical trace. Although the resistances of the traces contribute to the resistance at a location on the pair, for any two locations on the pair the trace connections from the first bus to a first connection pad and from the second bus to a second connection pad are identical. Thus, in these preferred embodiments trace resistances do not need to be taken into account in designing the geometry of the pair to provide for uniform resistances across the array.

When incorporating configurations having two or more wells, impedance measurement electrodes between electrode arrays of different wells can share a connection pad. Preferably one of the impedance measurement electrode structures of at least one of the electrode arrays of the device is connected to a connection pad that also connects to an impedance measurement electrode structure of at least one other of the electrode arrays of another well device. Preferably for at least two arrays of the device, each of the two or more arrays has a first impedance monitoring electrode structure connected to a connection pad that connects with an impedance measurement electrode structure of at least one other electrode array of another well, and each of the two or more arrays has a second impedance monitoring electrode structure that connects to a connection pad that does not connect with any other electrode structures or arrays of the device. Thus, in preferred configurations of a device there are at least two electrode arrays each of which has a first impedance monitoring electrode structure that is connected to a common connection pad and a second impedance monitoring electrode structure that is connected to an independent connection pad.

Preferred arrays for devices of the present invention include at least one pair of impedance measurement electrodes, each comprising two electrode structures, such as, in the form of a spiral configuration or an interdigitated configuration. Preferably the pair of impedance monitoring electrodes are fabricated on the substrate, in which the pair comprises two impedance monitoring electrode structures, each of which comprises multiple circle-on-line electrode elements, in which the electrode elements of one electrode structure alternate with the electrode elements of the opposite electrode structure. The pair of impedance monitoring electrodes may be provided in configurations, such as interdigitated, circle-on-line, diamond-on-line, concentric, sinusoidal and castellated.

A central advantage to systems described herein is that they can incorporate two separate and complete recording systems into one single instrument, namely, an extracellular signal recording system and impedance measurement system. This is accomplished by collecting field potential, which is a local readout such as by an extracellular recording electrode and impedance monitoring, which is an entire well readout by at least one pair of impedance electrodes respectively. In addition, with the capability of simultaneous recording of extracellular recording and impedance, the interaction of the results obtained from these separate recording system can be used to support each other.

Parallel impedance-based monitoring as well as extracellular recording based monitoring of cardiomyocytes, under the condition of electro-stimulation of cardiomyocytes, fills a major technological gap in monitoring cardiomyocytes in vitro. At present to our knowledge there are only a few technologies that can monitor cardiomyocyte population function in vitro, especially with regards to cardiotoxicity and are limited in their throughput. In addition to functional monitoring of cardiomyocyte beating the current invention offers several other major benefits which are worth discussing. Among these include the impedance system described here can monitor cardiomyocytes for short durations, milliseconds to minutes and long durations, several hours to days. Therefore, both short term and long term effects of drugs not only on cardiomyocyte beating, but viability and changes in morphology and adhesion can also be assessed. This feature is especially important because certain compounds such as $\beta$-2 adrenergic receptor agonists, well known and characterized modulators of heart function in vivo and in vitro, can induce long term hypertrophic responses in cardiomyocytes, which is associated with elongated morphology of the cells. Also, the systems of the present invention can also record cardiomyocyte action potentials or field potentials, allowing detailed electrophysiological analysis and assessment of cardiomyocytes for relatively short duration at a time. Furthermore, the ability of electro-stimulating cardiomyocytes allow for electrophysiological measurement and impedance measurement of otherwise non-beating cardiomyocytes. The synchronization of electro-stimulation with extra-cellular potential recording and cell impedance measurement would allow better and precise control of initiation timing points for excitation process and allow more reproducible measurement of extracellular potential and cell impedances.

In view of the above with or without applying electro-stimulation signals to stimulate or pace cardiomyocytes, impedance readout can be used to monitor the morphological or differentiative behavior of cardiomyocytes in vitro. Certain treatments can induce changes in morphological behavior of cardiomyocytes, such as inducing hypertrophy which is associated with cardiomyocyte elongation and expansion. Because impedance monitoring can detect changes in cell morphology, it can be used to for detection of hypertrophy in cardiomyocytes.

In cardiac culture preparation, impedance monitoring reflects the cell growth, which can be correlated through an impedance-based curve, namely, a cell index curve and contraction/relaxation function by impedance beating signals; while extracellular recording reflects cardiac excitation and conduction by field potential signals. Further, this the invention provides the ability to monitor viability of cardiomyocytes, the field potential of cardiomyocytes, or the excitation-contraction coupling or beating and morphological and differentiative aspects of cardiomyocytes in a label-free manner and real-time manner.

While the invention is primarily discussed in regards to cardiotoxicity and monitoring cardiomyocytes, the devices and systems can also be used to study a neuronal culture preparation, in which impedance monitoring reflects the cell growth, which can be correlated through a cell index growth curve. In addition as with electro-stimulation of cardiomyocytes, an impedance electrode can also serve for stimulation in the neuronal cell preparation, while evoking a response for network stimulation by either chemical or electrical could be recorded at the extracellular recording electrode(s). Theoretically, the configurations could also be used for any excitable cell cultures and tissue slices, so the system possesses high capacity for multiple applications.

An exemplary system for electro-stimulation, impedance monitoring and extracellular recording of excitable cells requires electrical connection of a device to a suitable a suitable electro-stimulation power source, impedance analyzer, and/or extracellular recording amplifier. With the above in mind, the invention provides a system for monitoring excitable cells, which includes a device having at least one well, each well having a bottom having a nonconductive substrate, wherein the substrate has a surface suitable for attachment of excitable cells; a power source configured to deliver an electrical signal capable of electro-stimulating excitable cells; and at least one analyzing module for measuring an electrical property from electro-stimulated excitable cells, characterized in that each well includes a pair of electro-stimulation electrodes configured to receive the electrical signal from the power source thereby delivering an electro-stimulating signal to the well for electro-stimulation of excitable cells attached to the substrate; and at least a second pair of electrodes communicatively coupled to the at least one analyzing module, which is selected from the group consisting of a pair of impedance monitoring electrodes communicatively coupled to the at least one analyzing module in the form of an impedance analyzer thereby permitting impedance monitoring of excitable cells attached to the substrate, and an extracellular recording electrode pair communicatively coupled to the at least one analyzing module in the form of an extracellular recording amplifier thereby permitting extracellular recording of excitable cells attached to the substrate.

Figure 3:
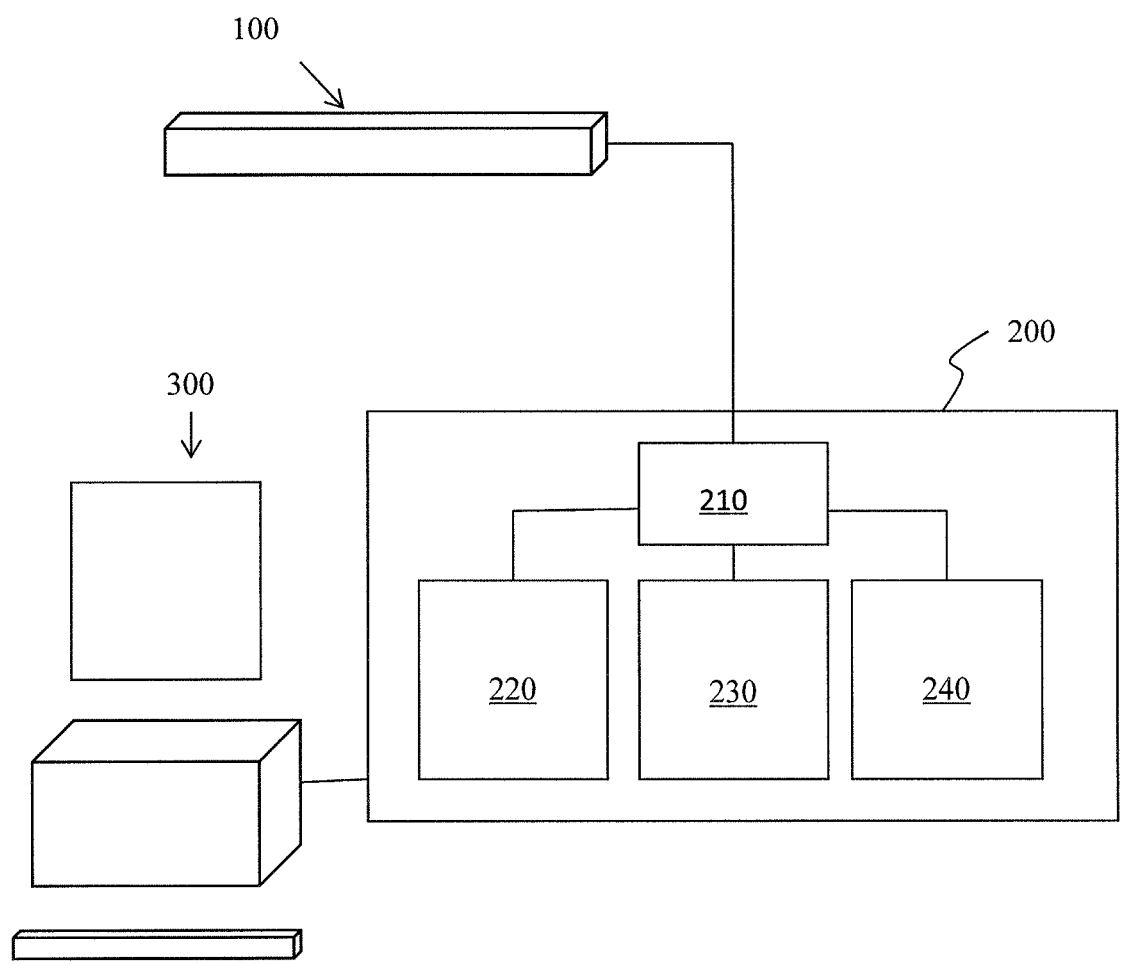
FIG. 3 depicts an exemplary system of a device 100, a combined analyzer 200 having switchable electro-stimulation, impedance monitoring, and extracellular recording functions and computer 300.

Referring to FIG. 3, in some embodiments a the power source 220, impedance analyzer 230 and extracellular recording amplifier 240 are combined into a combined analyzing module 200, which is operably connected to a multiwall device 100 for electro-stimulation and monitoring of excitable cells. An electronic switch 210 can selectively switch electrical connection with at least one electrode of the device 100 between the power source 220 and impedance analyzer 230, between the power source 220 and extracellular recording amplifier 240, and/or the impedance analyzer 230 and extracellular recording amplifier 240, thereby providing numerous combinations. The combined analyzing module 200 can then be coupled to a computer 300 loaded with software to execute programming or analyze data.

Accordingly, in some embodiments of the invention, a system for monitoring excitable cells is provided, which includes a device for electro-stimulation and monitoring of excitable cells, a power source capable of delivering an electrical signal to a pair of electro-stimulation electrodes that stimulates excitable cells; at least one analyzing module in the form of an impedance analyzer capable of monitoring cell substrate impedance of cells through the pair of impedance monitoring electrodes or an extracellular recording amplifier capable of recording extracellular potentials of cells through the extracellular recording electrode pair. The system is configured to electro-stimulate the excitable cells at a different time compared to measurement from the at least second pair of electrodes.

Electro-stimulation is accomplished by an electrical signal delivered from the power source to the electro-stimulation electrodes and to attached cells, which can be in the form of a series of electrical pulses. That is, while impedance monitoring and extracellular recording may incorporate different spectra, waveforms or the like that can continue over an extended time, electro-stimulation is typically performed more quickly in a fast on-off approach followed by a delay in the off state to permit measurement of the excitable cells without interference of the electro-stimulation signal. The skilled artisan will appreciate that in some instances the electro-stimulation signal may be at least partially filtered to prevent interference from a lower intensity state. Preferably, electro-stimulation of the excitable cells is performed at a plurality of time intervals. Most preferably, the time intervals are at regular time intervals. As a nonlimiting example, electro-stimulation can be performed by delivering a biphasic pulse of about 0.8-1.5 ms, more preferably about 1 ms and at an output voltage of 1-2 V or more preferably about 1.2 V.

An extracellular recording amplifier is communicatively coupled to the extracellular recording electrode pair for electrical communication to permit amplifying and recording electrical voltage signals between the recording electrodes and reference electrodes. That is, extracellular recorded voltage signals are recorded as the difference in the electrical potentials between the recording electrode and reference electrode. Such electrical voltages are induced on the electrodes as a result of ionic current or movement through cell culture media or solution supporting the cells during the experiment as a result of opening and/or closing of different ion channels across cell membrane during the action potential duration. In order to achieve improved consistency and reproducibility of the recorded voltage signals, it is desirable to minimize the contribution of any electrical signal from the reference electrode to the recorded voltage signals and to ensure that the majority, if not all, of the recording voltage signals are derived from that on the recording electrode.

Generally, it is desirable and it is recognized for the reference electrodes to have small electrode impedances. The small electrode impedance is achieved by using reference electrodes with large effective surface areas by increasing the ratio of the surface area of the reference electrodes to that of recording electrode by a factor of a hundred, even thousands of times. Such small electrode geometry has advantages of recording the electrical potential generated by a small number of the cells located on the recording electrodes. Action potentials from such a small number of the cells tend to be synchronized or nearly synchronized, allowing for a better time resolution for recording extracellular potential and for resolving different features of the recorded potential. However, one limitation of such extracellular recording is that due to small area of such electrodes, there tends to be large variations in recorded signals between different recorded electrodes of the same geometry in the same wells (if multiple recording electrodes are positioned inside a single well) or different wells. In particular, if insufficient number of the cells is added to the well to cover all the recording electrodes, it is possible that some recording electrodes may not show any recorded signal or only show recorded signals of very small magnitude. Furthermore, depending on exact distribution or locations of the cells on the recording electrodes, different recording electrodes may show significantly different extracellular potential waveforms. For this reason, it may be preferable to have at least two recording electrodes positioned at about the middle of the array an in some instances more. Extra-cellular potentials from each such recording electrode can amplified and recorded separately. The user can then pick and choose appropriate signal waveforms recorded from individual recording electrodes for data analysis. Alternatively or in combination, a preferred approach is to culture a layer of excitable cells such that the layer covers all recording electrodes.

In the system for monitoring impedance of excitable cells the impedance analyzer is communicatively coupled to impedance monitoring electrodes to monitor impedance. In some embodiments, the impedance analyzer is capable of measuring impedance between 0.1 ohm and $10^5$ ohm in frequency range of 1 Hz to 1 MHz. The impedance analyzer is preferably capable of measuring both resistance and reactance (capacitive reactance and inductive reactance) components of the impedance. In a preferred embodiment of the above system, the impedance analyzer is capable of measuring impedance between 1 ohm and $10^3$ ohm in frequency range of 1.00 Hz to 300 kHz.

In preferred embodiments the impedance analyzer is capable of impedance measurements at millisecond time resolution. The required or desired time resolution may vary depending on the excitation cycle of the excitable cell. Excitable cells having shorter excitation cycles or pacing electro-stimulation more quickly, would tend to require faster time resolution. In some embodiments 500 millisecond time resolution is sufficient, such that at least two consecutive impedance measurements are between about 300 milliseconds and about 500 milliseconds apart. In preferred embodiments, impedance measurement at millisecond time resolution includes at least two consecutive impedance measurements less than 100 milliseconds apart. In some instances the at least two consecutive impedance measurements are less than 50 milliseconds or less than 40 milliseconds apart. In some instances the at least two consecutive impedance measurements are less than 20 milliseconds apart. In some instances at least two consecutive impedance measurements are less than 10 milliseconds apart. In some instances millisecond time resolution includes two consecutive impedance measurements between 1 millisecond and 5 milliseconds, between 5 milliseconds and 10 milliseconds, between 10 milliseconds and 20 milliseconds, between 20 milliseconds and 40 milliseconds, or between 40 milliseconds and 50 milliseconds apart. In some instances millisecond time resolution includes at least two consecutive impedance measurements between 50 milliseconds and 100 milliseconds apart. In some instances millisecond time resolution includes at least two consecutive impedance measurements between 100 milliseconds and 150 milliseconds or between 150 and 300 milliseconds apart.

Achieving millisecond time resolution can be achieved by using fast processing electronic chips for analogue-to-digital conversion, for parallel digital signal processing and data calculation with field-programmable gate array (FPGA) and for fast communication between the impedance measurement circuitry and software. Another example of includes the use of multiple analogue-to-digital (AD) conversion channels so that analog electronic signals from multiple channels can be converted to digital signals simultaneously. Such parallel AD conversion is important, particular for the system having multiple wells, each of which's measurement time resolution is required to be in the millisecond resolution.

In addition, when using a device having multiple wells, the software can issue a command for measuring multiple wells' impedances. The measurement circuitry would simultaneously or nearly simultaneously perform signal conversion, signal processing and impedance calculation for multiple wells. The multiple impedance data for the multiple wells would be sent over the communication lines to the computer sequentially with one well's data at the same time or simultaneously with more than one well's data being sent at a time. In this "measurement of multiple-wells' impedances at a time" mode, the system may be performing multiple tasks simultaneously, for example, while one well's impedance data is being measured and calculated, another well's impedance data may be communicated and sent over the communication lines to the computer.

With millisecond time resolution for impedance measurement, it becomes possible to resolve individual beating cycles of cardiomyocytes cultured on electrodes and study the excitation, contraction and release of beating cells. Whilst theoretically one needs at least two data points for each beating cycle, in practice more than 2 data points are needed for each beating cycle. For example, if cells have a beating rate of 60 beats per minute, i.e, one beat per second. It would be preferred to have a time resolution of at least 200 milliseconds so that each beating cycle consists of 5 data points. More preferably, the measurement time resolution is 100 milliseconds. Still more preferably, the time resolution is 50 milliseconds or less.

Cell-substrate impedance monitoring at millisecond time resolution can be used to efficiently and simultaneously perform multiple assays by using circuitry of the device station to digitally switch from recording from measuring impedance over an array in one well to measuring impedance over an array in another well. Similarly, groups of wells may be monitored simultaneously and switching between occur between designated groups. In one embodiment of the above system, the system under software control is capable of completing an impedance measurement for an individual well at a single frequency within milliseconds, such as less than 100 milliseconds, less than 40 milliseconds, less than 20 milliseconds, less than 10 milliseconds or between 1 millisecond and 40 milliseconds. In some embodiments the user may choose the frequency of measurement for millisecond time resolution.

As discussed above, one or more electrodes in a pair of electrodes can be shared with another pair of electrodes. Sharing of electrodes can accomplished at least in part by switching the communicative coupling for electrical connection between the power source for electro-stimulation and either the impedance analyzer or extracellular recording amplifier. Alternatively, sharing of electrodes can be accomplished at least in part by switching the communicative coupling for electronic connection between the impedance analyzer and the extracellular recording amplifier. In each instance, switching is preferably performed through an electronic programmable switch and is provided together with the power source, impedance analyzer and extracellular recording amplifier in a combined analyzer, which itself can be coupled to a computer for performing measurement instructions or data analysis.

In some embodiments a combined analyzer or electromechanical apparatus or assembly capable of interfacing multiwell devices can include one or more platforms or one or more slots for positioning one or more multiwell devices, such as in the form of a device station with carriage. The one or more platforms or one or more slots can comprise sockets, pins or other devices for electrically connecting the device to the device station such as interaction through connection pads. The system can be configured such that multiwell devices can be positioned in a tissue culture incubator during electro-stimulation, extracellular recording or impedance monitoring while the computer and optionally combined analyzer are located outside the tissue culture incubator. This can be accomplished through the electrical connection of the device through a device station that itself is inside the incubator and electrically coupled to a combined analyzer that is outside of the incubator. Alternatively, the combined analyzer can be within the incubator and communicate with the computer that is outside of the incubator.

The device station or electromechanical apparatus or assembly capable of interfacing multiwell devices includes electronic circuitry that connect to the power source, impedance analyzer, and/or extracellular recording amplifier and can incorporate electronic switches that can switch on and off connections to each of the two or more pairs of electrodes within a well of the multiwell devices used in the system. The switches of the device station or electromechanical apparatus or assembly capable of interfacing multiwell devices are controlled by a software program, each of which preferably provides millisecond time resolution.

The systems of the invention are typically controlled through commands sent from a computer operably connected to the power source, impedance analyzer and extracellular recording amplifier. The computer is typically loaded with software that provides two functions. A first is data acquisition and a second is data analysis. The software uses graphical interfaces for ease of use.

Figure 4A:
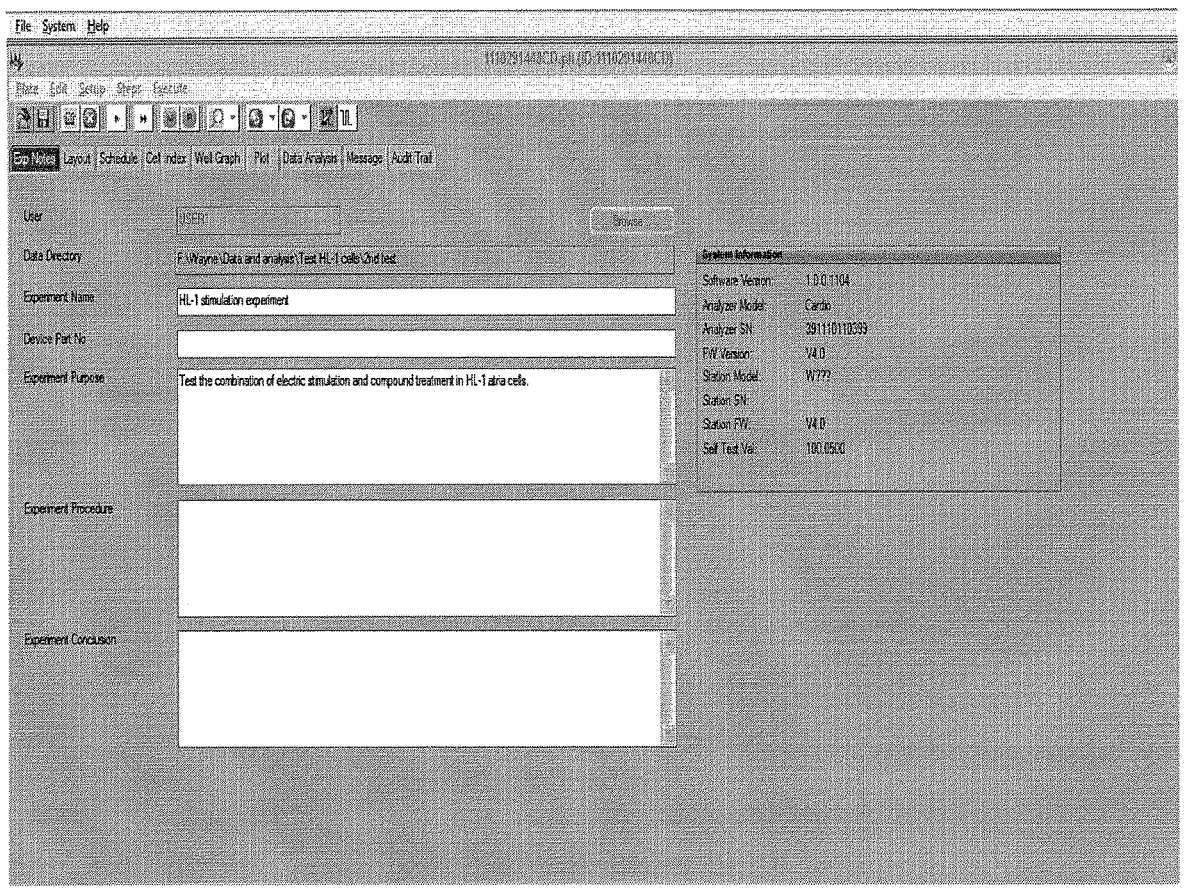
FIGS. 4A-D depict examples of the graphical interface for software used in data acquisition (FIGS. 4A-C) and data analysis (FIG. 4D).
Figure 4B:
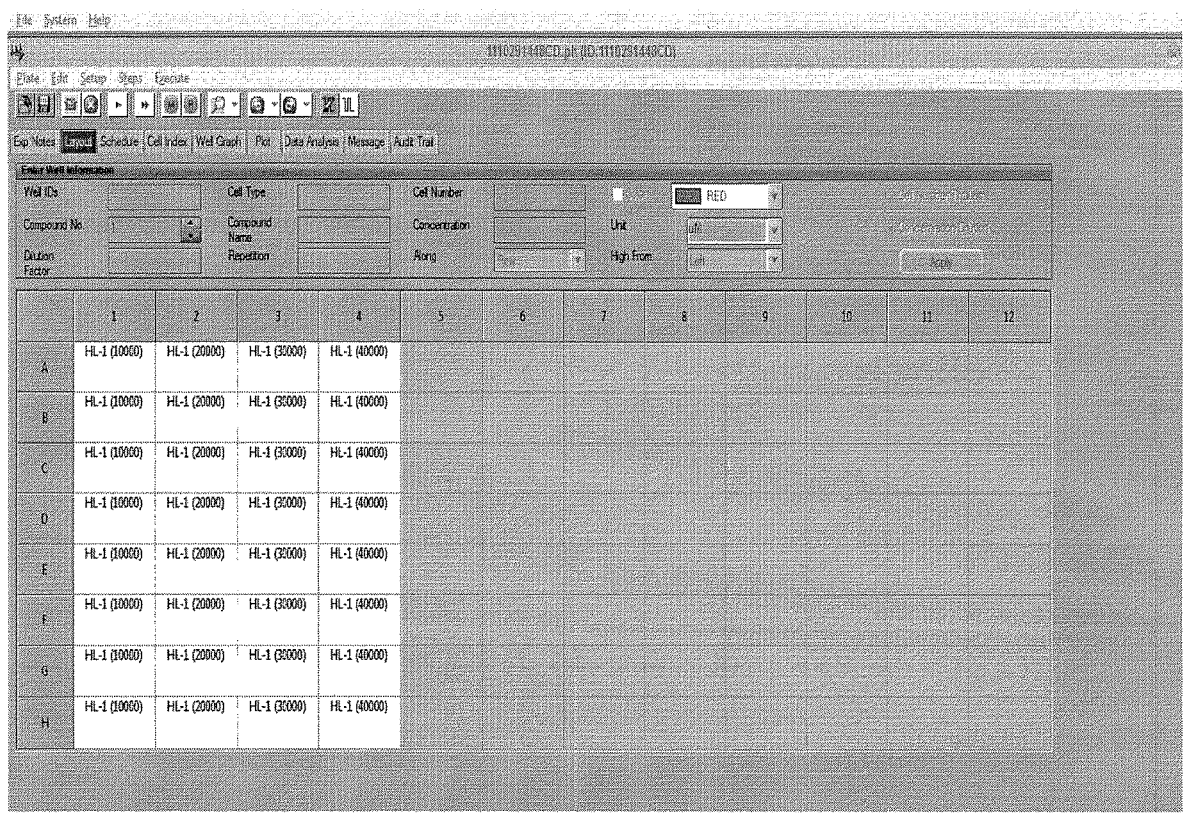
Figure 4C:
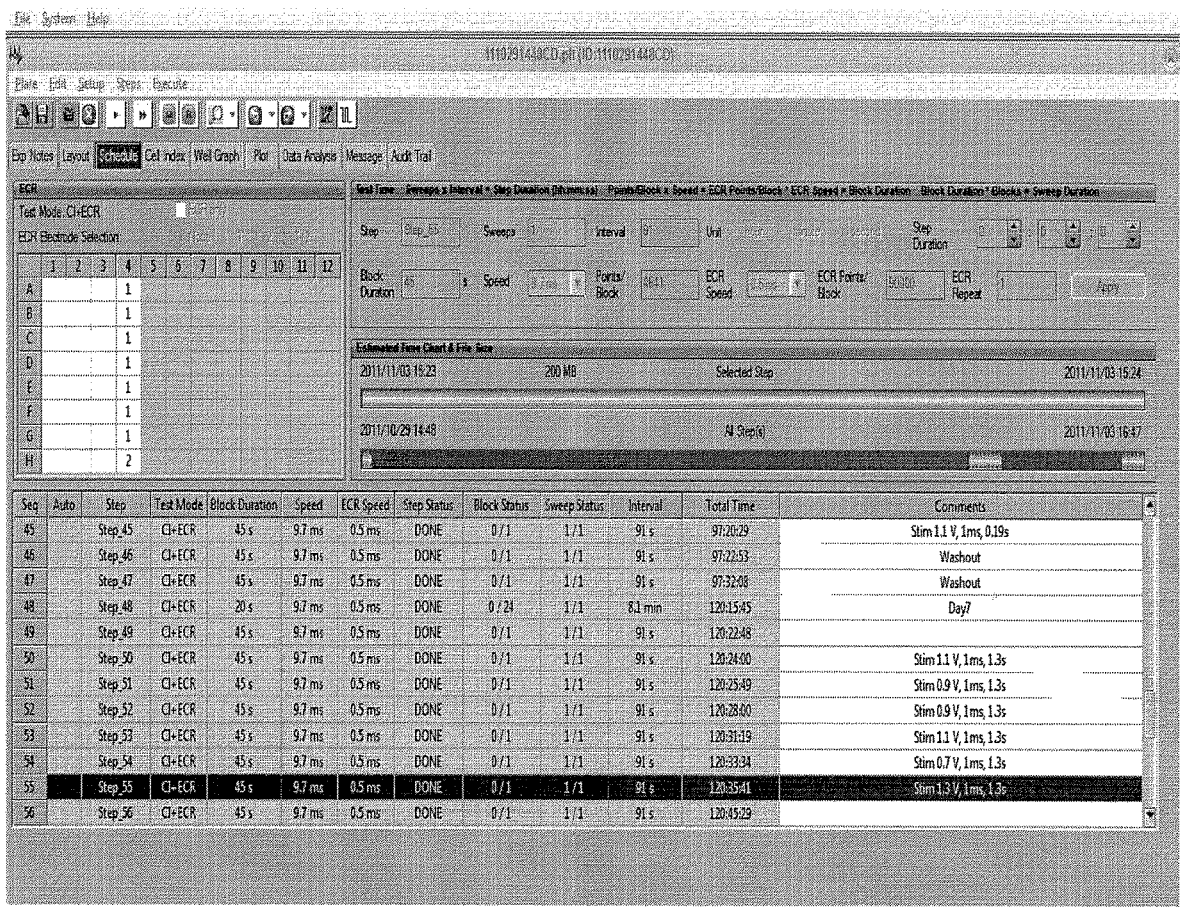

The data acquisition software is used to define the experiment, setup recording steps, monitor the raw data, adjust settings and to collect raw data files. An example of graphical interface for data acquisition is shown in FIGS. 4A-C, where FIG. 4A shows an interface for entering experimental notes such as experiment name, purpose or the like; FIG. 4B shows a well layout where HL-1 atria cells are seeded at different density from 10,000 in column 1 to 40,000 in column 4, and FIG. 4C shows wells specific settings for, electro-stimulation, impedance monitoring and extracellular recording.

Figure 4D:
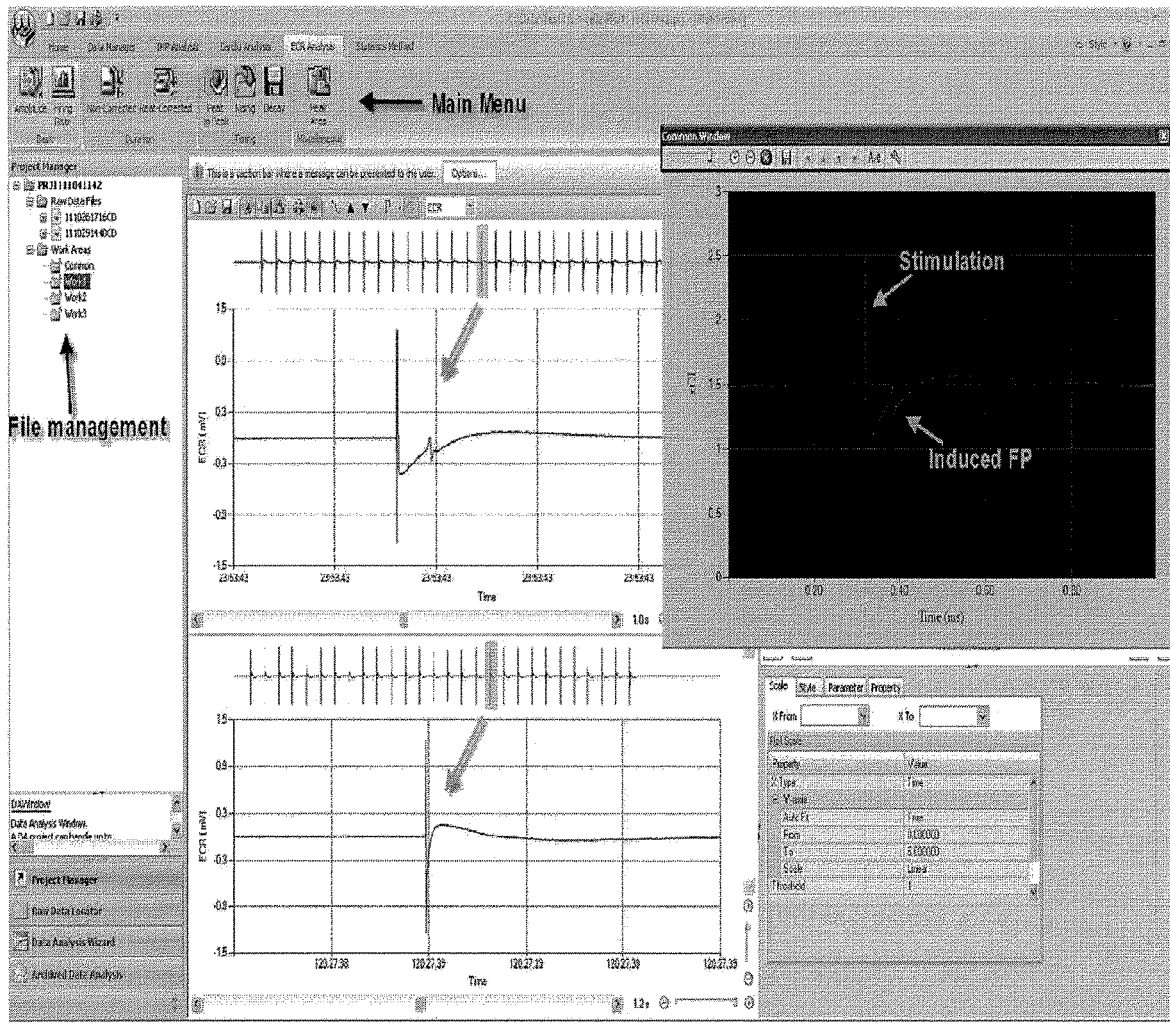

Preferably, the software can also analyze impedance data and extracellular recording data. An exemplary graphical interface for data analysis is provided in FIG. 4D, which shows a file structure "tree" at the left side for file management, single or multiple channels of raw data file displayed in the middle section of the window and the analysis result displayed at the right side of the window. In addition, the data analysis software also has the ability to do single field potential waveform analysis.

Figure 5:
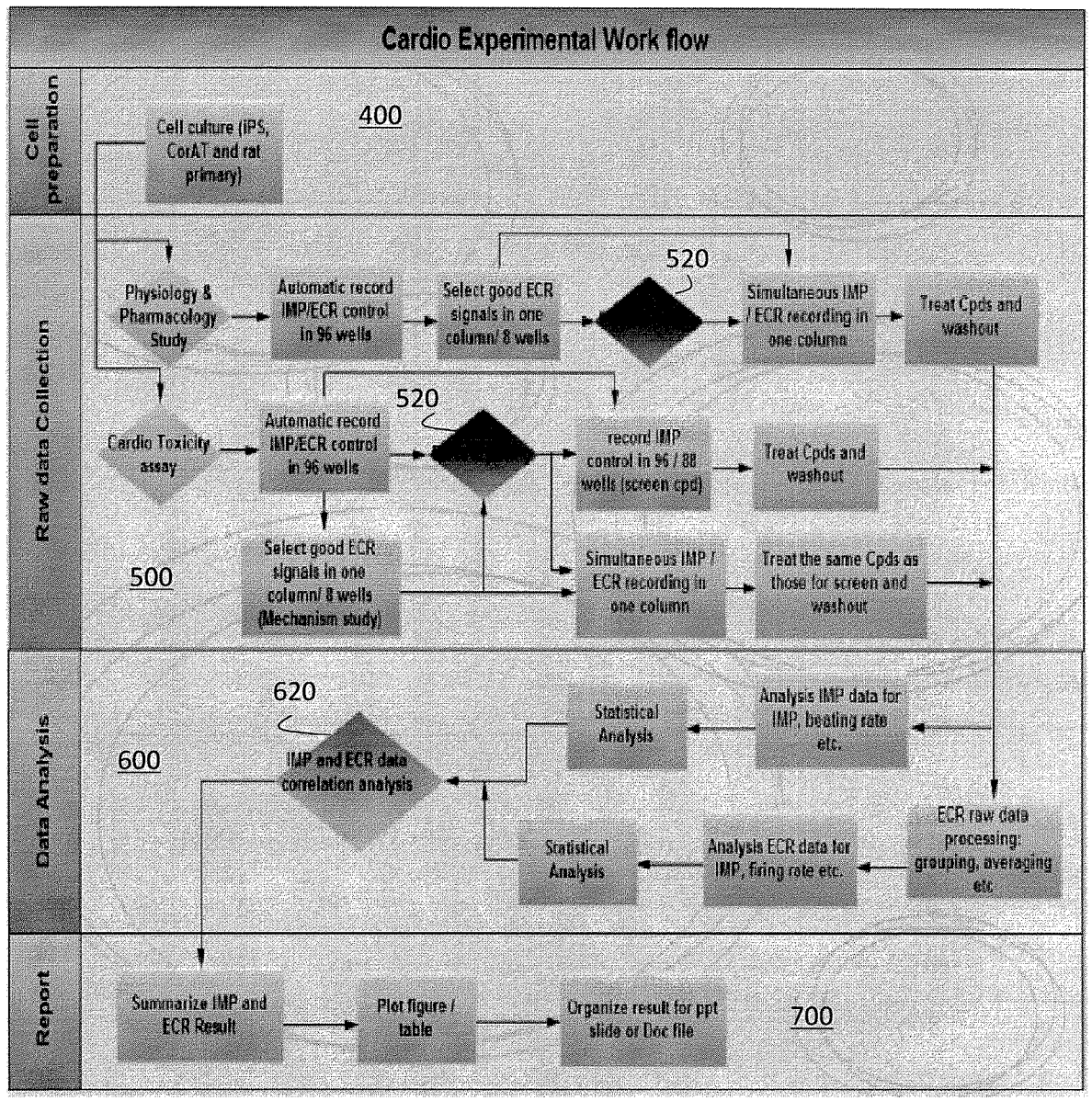
FIG. 5 shows an exemplary cardio experimental work flow chart.

An overview of an exemplary experiment and how it interacts with the software can be seen in FIG. 5, where a first step involves cell preparation 400, such as culturing cells, proceeds through raw data collection 500 using electro-stimulation 510 if extracellular recording or impedance monitoring does not result in desired activity, such as poor beating of cardiomyocytes. After raw data collection 500 data analysis 600 is conducted such as correlation of Impedance and ECR data 620. Finally reports 700 are generated providing the results from the impedance and extracellular recording results in desired formats.

In preferred embodiments, the software can calculate an impedance-based parameter, such as cell index (CI) for one or more time points for one or more wells of the multiwell device through suitable programming. In some preferred embodiments, the software can also calculate a cell change index (CCI) from impedance measurements of one or more wells of the multiwell device. The software can preferably generate plots of impedance-based parameters over time, such as but not limited to impedance-based curves selected from impedance measurements, CI, or CCI. The software may perform other analysis as well, such as calculate cell number from CI, generate dose-response curves based on impedance data, calculate IC values based on impedance values, and calculate kinetic parameters of the excitation cycle cell based on impedance-based parameters and impedance-based curves. In some embodiments the beating cycle of a cardiomyocyte population is determined, which may include initiation and decay of individual beats. Peaks may be derived from the detection of vectors associated with initiation of beating or beating decay. Peaks may be derived with other methods. In further embodiments the change in beating cycle of a cardiomyocyte population is determined in response to a stimulus such as administration of a compound to the cells. The software of the impedance monitoring system can also store and display analyses of the data, such as calculated impedance values impedance-based parameters and kinetic parameters derived therefrom, Data can be displayed on a screen, as printed data, or both. Data may be stored on a hard drive for exportation into compatible programs for further analysis or data storage Methods of Monitoring Cardiomyocyte Beating, Viability, Morphology and Electrophysiological Properties The invention provides methods of monitoring excitable cells, methods for monitoring cardiomyocyte beating, viability, morphology, assessing cardiotoxic affects associated with administering of one or more compounds to a population of cardiomyocyte or cardiomyocyte precursor cells. The methods include obtaining a sample of excitable cells, electro-stimulating the excitable cells; and impedance monitoring and/or extracellular recording of the excitable cells. Preferably, impedance monitoring and extracellular recording is performed simultaneously to achieve simultaneous real time measurements.

It is well established that certain pharmacological treatments and disease conditions can result in cardiac hypertrophy or atrophy culminating in changes in the morphology of cardiomyocyte. The methods and systems herein have developed a system for monitoring cell substrate impedance to precisely measure and quantify these changes in cell morphology and shape.

In addition, the present invention also discloses an approach for monitoring extracellular field potential, which is an electrical potential produce by cells that is outside of the cell. However, as shown in the examples, extracellular recording also provides insight as the activity of ion channels, which are of central interest when assessing cardiotoxicity of potential therapeutics.

In view of the above, a method of monitoring excitable cells is provide, which includes providing a system for electro-stimulation, impedance monitoring and extracellular recording of excitable cells; adding a sample of excitable cells to the device; electro-stimulating the excitable cells; and impedance monitoring and extracellular recording of the excitable cells.

In a related embodiment, a method of monitoring excitable cells is provided, which includes providing a system for electro-stimulation and impedance monitoring of excitable cells; adding a sample of excitable cells to the device; electro-stimulating the excitable cells; and performing impedance measurements of the excitable cells.

In another related embodiment, a method of monitoring excitable cells is provided, which includes providing a system for electro-stimulation and extracellular recording of excitable cells; adding a sample of excitable cells to the device; electro-stimulating the excitable cells; and performing extracellular recording of the excitable cells.

Among the cells that may be monitored include any excitable cells, such as primary cardiomyocytes harvested from animal tissue, cultured cardiomyocytes, cardiomyocyte precursor cells, embryonic stem cells, embryonic stem cell derived cardiomyocytes, cardiomyocyte cell lines, enriched cardiomyocyte cells and the like. Alternatively the invention has also shown that neuronal cells may also be used.

Obtaining or harvesting suitable excitable cells may be performed using a variety of harvesting, collecting, culturing, purifying, enriching or differentiating techniques known in the art to which the invention belongs. While the device can detect changes, such as impedance change and extracellular potential in a single cell, preferably samples contain a plurality of cells so that the cells will join together for communication with one another, such as through gap junctions. Clear changes in electrocellular recording and impedance measurement have been identified using population of about 10,000-14,000 cells; however, this is not intended to be limiting.

Cells may be placed into culture then immediately stimulated or measured; however, it has generally been preferable to culture cells such that they attach to the substrate prior to stimulation. More preferably, cells are grown or differentiated on the substrate for a sufficient time in that they join to form a cell layer over the recording electrodes of the extracellular recording electrode pair and over the pair of impedance monitoring electrodes. In some embodiments, electro-stimulation is performed within 1 hour of placing cells in the device; however, the substrate forming the bottom of the well has been shown suitable for long term culturing and thus cells may be cultured as desired, such as for more than 5 days, more than 10 days, more than 15 days, more than 20 days or even more than one month depending on the interests of the experiment and regular cell culture maintenance.

Further, impedance monitoring may be used to assess how well cells are attached to the substrate, the viability of the cells or to assess the quantity of cells in the sample prior to electro-stimulation, to assess growth curves or the like. Further, impedance or extracellular recording may be used to determine whether electro-stimulation is necessary or desired. In some instances cardiomyocytes derived from embryonic stem cells will begin to beat spontaneously, which can be detected or measured through impedance and extracellular recording. However, even cells that being spontaneous beating can be electro-stimulated to establish a more regular beating or a beating at an increased frequency.

Excitable cells are electro-stimulated through applying a signal via the pair of electro-stimulation electrodes. As indicated above, the pair of electro-stimulation electrodes may be a dedicated pair of electrodes, preferably one or more electrodes within the pair of electro-stimulation electrodes may be shared between the pair of impedance measurement electrodes or the extracellular recording electrode pair. Sharing of the electro-stimulation function is permitted in part because of the fast switching between connectivity to the power source for electro-stimulation and the impedance analyzer or between the power source for electro-stimulation and the extracellular recording amplifier. While the particular specifications of a device can vary, stimulation is generally accomplished by applying voltage in a range of about 1-2 V for about 1 ms, at an interval of every 1-1.5 seconds or so. Particularly encouraging results were obtained when applying 1.1 V for 1 ms every 1.2-1.3 s.

When providing two or more wells, each well may be pulsed together such that electro-stimulation occurs simultaneously in more than one well or pulses may be staggered such that two or more wells are pulsed with different at different interval. Electro-stimulation intervals can be selected through a software and computer interface.

When performing impedance monitoring, preferably, impedance is measured at millisecond time resolution. For example, resolution on the order of 1-10 ms provides high resolution of beating of cardiomyocytes. Impedance measurements may themselves be compared; however, in preferred embodiments a cell index is calculated from impedance measurements as an impedance parameter and plotted over time as an impedance-based curve or cell index curve. Accordingly, a cell index curve may be used as an impedance-based curve for comparison, such as by comparing cell index curves over time. In other embodiments, cell change index is calculated from cell index and plotted as an impedance based curve. Accordingly, cell change index may be used as impedance-based parameter for comparison, such as by comparing cell change index curves over time. The skilled artisan will appreciate that when comparing impedance-based curves, a same type of curve will be compared. For example, comparison would involve comparing cell index curves to one another, cell change index curves to one another and the like.

While impedance measurements themselves can be compared, their comparison is complicated by culture conditions, such as differences between cell populations. Accordingly a number of calculations have been established previously that result in values that permit improved comparison. Among these are cell index (CI) and cell change index (CCI), each of which has been discussed in detail in the following US patents: U.S. Pat. Nos. 7,470,533, 7,459, 303, 7,192,752, 8,026,080, 7,560,269, 8,263,375, 7,468,255, 8,206,903 and 8,420,363. Accordingly, the use of cell index and cell change index in the formation of an impedance-based curve is well established in the art. Further, these documents can be consulted for method of calculating cell index (CI) or cell change index (CCI). However, a brief overview introduction is provided below.

The cell index (CI) obtained for a given well reflects how many cells are attached to the electrode surfaces in this well and how well cells are attached to the electrode surfaces in the well. In this case, a zero or near-zero "cell index" indicates that no cells or very small number of cells are present on or attached to the electrode surfaces. In other words, if no cells are present on the electrodes, or if the cells are not well-attached onto the electrodes cell index=0. A higher value of "cell index" indicates that, for same type of the cells and cells under similar physiological conditions, more cells are attached to the electrode surfaces. Thus Cell Index is a quantitative measure of cell number present in a well. A higher value of "cell index" may also indicate that, for same type of the cells and same number of the cells, cells are attached better (for example, cells spread out more, or cell adhesion to the electrode surface is stronger) on the electrode surfaces.

In other embodiments, a normalize cell index is calculated from the cell index and plotted as an impedance based curve. A "normalized cell index" at a given time point is calculated by dividing the Cell Index at the time point by the Cell Index at a reference time point. Thus, the Normalized Cell Index is 1 at the reference time point. Normalized cell index is cell index normalized against cell index at a particular time point. In most cases in the present applications, normalized cell index is derived as normalized relative to the time point immediately before a compound addition or treatment. Thus, normalized cell index at such time point (immediately before compound addition) is always unit one for all wells. One possible benefit for using such normalized cell index is to remove the effect from difference in cell number in different wells. A well having more cells may produce a larger impedance response following compound treatment. Using normalized cell index, it helps to remove such variations caused by different cell numbers.

In other embodiments, a cell change index (CCI) is calculated from the cell index. A "cell change index" at a given time point is calculated by subtracting the cell index at a standard time point from the cell index at the given time point. Thus, the cell change index is the absolute change in the cell index from an initial time (the standard time point) to the measurement time. CCI is the normalized rate of change in cell index. CCI values can be used to quantify the cell status change. For cells in an exponential growth under regular cell culture condition, the cell index determined by a cell-substrate impedance monitoring system described herein is expected to be a proportionate measure of the cell number in the well since the cell morphology and average extent of cell adhesion to the electrode surfaces among the whole cell population do not exhibit significant changes over time.

Turning back to comparing impedance based parameters or impedance based curves, in preferred embodiments, cell index is preferably calculated and plotted over time to form an impedance base curve. Impedance based curves over time may be aligned or overlayed with one another according to electro-stimulation time points. For example, two or more impedance-based curves may be aligned or overlayed using a point or time of electro-stimulation as a starting basis.

The skilled artisan will appreciate that when comparing impedance-based parameters each member for comparison is a member of a same parameter. That is, impedance measurements can be compared to one another; cell index, which can be calculated from the impedance measurement, can be compared to one another; or cell change index, which can be calculated from cell index, can be compared to one another. Although individual members of a parameter can be compared, preferably the impedance based parameters are plotted over time to provide an impedance-based curve then compared, whether an impedance measurement curve, a cell index curve, or cell change index curve to identify differences changes in impedance, which may be associated with administration of a compound, expression of an inserted nucleic acid or the like. In preferred embodiments, cell index is calculate from impedance measurements and plotted over time to provide an impedance-based curve in the form of a cell index curve.

Extracellular recording measures the extracellular potential (also referred to as field potential (FP)) and is a close simulation to its counterpart, intracellular action potential (AP), therefore identifying peaks and wave form changes in field potential can be used to predict ion channel activity. Accordingly, the extracellular recording measurements are plotted over time, typically in microvolts, to identify variations in the field potential (FP). Sampling rate for extracellular recording can be about 1 KHz, 2 KHz, 5 KHz and 10 KHz. Extracellular potential is preferably plotted over time to form a field potential curve.

Periods or electro-stimulation intervals from two or more impedance curves and/or two or more field potential curves may be overlayed to identify trends or differences in impedance and/or field potential. For clarity, the two or more impedance curves can be from different wells, such as from wells having serial dilutions of a compound or may be from a same well at a later time point. Accordingly, the addition of compounds suspected of affecting either the field potential (likely due to affecting ion channels) or impedance of the excitable cells may be added to a culture of cells and changes in impedance or field potential can be identified or measured through the comparison of the an impedance-based parameter and field potential before and after compound addition, such as by comparing cell index curves or field potential curves over time. Accordingly, in preferred embodiments comparisons are performed by comparing cell index curves over time to one another and comparing field potential curves over time to one another. In instances where it is not readily apparent by viewing each curve over time, curves between different electro-stimulation periods can be overlayed and compared using curve comparison algorithms. Accordingly, overlaying impedance curves may identify changes in impedance and overlaying field potential curves may identify changes in field potential.

The methods are useful in assessing the cardiotoxicity of compounds through monitoring impedance of a beating cell population and identifying any changes after compound administration. For instance, a compound suspected of affecting excitation contraction coupling of the excitable cells can be provided to the well. Impedance monitoring can be performed before and after adding the compound and impedance-based parameters (such as cell index) prior to and after adding the compound can be calculated and compared to identify changes in the impedance parameter in response to the compound and thus predict whether the compound is likely to be cardiotoxic. Preferably, the impedance based parameter is compared between at least two different electro-stimulation intervals; however, three or more, four or more, five or more, six or more and the like intervals can be compared.

In some embodiments, impedance and/or extracellular recording is conducted to assess an effect of a compound, such as its potential cardiotoxicity, on cell. An exemplary method would be to provide a culture of cells, electro-stimulate the cells, perform impedance monitoring and/or extracellular recording before and after adding the compound and analyzing the results. As such, the analysis could include calculating an impedance-based parameter (such as cell index or cell change index) from impedance prior to and after adding the compound and their comparison to identify changes in the impedance parameter. Further, the impedance-based parameter may be plotted over time to form an impedance-based curve before and after administration for comparison. Alternatively or in addition, extracellular potential before and after administration can be compared such as by comparing field potential curves over time to identify differences. Such analysis in response to the compound can be used to predict whether the compound is likely to be cardiotoxic, affects beating, affects cardiomyocyte morphology or affects ion channels. Preferably, the impedance based parameter is compared between at least two different electro-stimulation intervals; however, three or more, four or more, five or more, six or more and the like intervals can be compared. Compounds for testing are not intended to be limiting and may include organic or inorganic molecules, drugs, peptides, proteins, antibodies, siRNA, shRNA, miRNA, cDNA, lipids or any combination thereof.

While the above has been primarily discussed with respect to monitoring the excitable cells before and after adding a compound suspected of having a cardiotoxic affect to a well and comparison of impedance or field potential before and after administration, in related approaches the compound can be added to two or more wells in different concentrations to evaluate cardiotoxicity or activity compared to dose or can be added to two or more wells and administered in same well with an antagonist, such as to further verify suspected findings or mechanism of action. For instance, impedance-based curves can be used to calculate the compound dose-dependent changes in cardiomyocyte morphology, ion channel modulation, impedance, field potential or the like and generate an EC-50 value for the potency of the compound. In addition, extracellular recording permits comparisons with cells at various developmental stages to assess development.

Still further, analysis of impedance curves or extracellular recording curves after compound administration can be clustered and grouped according to similarities thereby being suggestive of a common mechanism of action. Further, once profiles of known compounds are grouped, unknown compounds can then be tested in such a system, and the impedance-based curves and extracellular recording curves compared to the group, then the compound can be assigned to one or more group based on similarities or differences between curves.

In view of the above description and the examples that follow, it should become evident that while systems of the invention can be applied for cardiac electrophysiology recording for drug/compound profiling and cardiac safety screening, it can also be used to record from any excitable preparations. With incorporation of cell electro-stimulation, field potential recording and cell-impedance monitoring technologies, this system is the first single instrument which can simultaneously monitor the cardiac excitation by field potential and beating functioning by impedance in vitro, yet the device still adds electro-stimulation of cells to induce or regulate excitation contraction coupling or beating of a cell population and thus permits use of cells that require stimulation to begin or continue beating.

Assessing Genetically Manipulated Embryonic Stem Cells and Effects on Cardiomyocyte Function In another aspect, the present invention is directed to method to assess the effect of gene knockout in an embryonic stem (ES) cell upon differentiating into to a cardiomyocyte, the method including providing a device for monitoring impedance operably connected to an impedance analyzer, wherein the device includes at least two wells; adding wildtype ES cells as control to at least a first well and ES cells with a gene knockout in at least a second well; optionally electro-stimulating cells in each well; monitoring impedance of the at least two wells and optionally determining cell indices from impedance values to generate an impedance-based curve for each well; comparing the impedance-based curves between the first and second wells, and if significantly different, concluding that the gene knockout may affect at least one selected from the group consisting of cardiomyocyte viability, cardiomyocyte morphology, cardiomyocyte beating.

In a related approach, the invention also provides a method to assess the effect of gene knockout in an embryonic stem (ES) cell upon differentiating into to a cardiomyocyte, the method including: providing a device for monitoring impedance and extracellular recording, that are operably connected to an impedance analyzer and extracellular recording amplifier, wherein the device includes at least two wells; adding wildtype ES cells as control to at least a first well and ES cells with a gene knockout in at least a second well; monitoring impedance and extracellular recording of the at least two wells and optionally determining cell indices from impedance values to generate an impedance-based curve for each well; comparing the impedance-based curves and field potential curves between the first and second wells, and if significantly different, concluding that the gene knockout may affect at least one selected from the group consisting of cardiomyocyte viability, cardiomyocyte morphology, cardiomyocyte beating or affecting an electrophysiological property of the cardiomyoctye.

In another aspect, the present invention is directed to method to assess the effect of a transgene in an embryonic stem (ES) cell upon differentiating into to a cardiomyocyte, the method including providing a device for monitoring impedance operably connected to an impedance analyzer, wherein the device includes at least two wells; adding wildtype ES cells as control to at least a first well and ES cells harboring a transgene knockout in at least a second well; optionally electro-stimulating cells in each well; monitoring impedance of the at least two wells and optionally determining cell indices from impedance values to generate an impedance-based curve for each well; comparing the impedance-based curves between the first and second wells, and if significantly different, concluding that the transgene may affect at least one selected from the group consisting of cardiomyocyte viability, cardiomyocyte morphology, cardiomyocyte beating.

In a related approach, the invention also provides a method to assess the effect of a transgene in an embryonic stem (ES) cell upon differentiating into to a cardiomyocyte, the method including: providing a device for monitoring impedance and extracellular recording, that are operably connected to an impedance analyzer and extracellular recording amplifier, wherein the device includes at least two wells; adding wildtype ES cells as control to at least a first well and ES cells harboring a transgene in at least a second well; monitoring impedance and extracellular recording of the at least two wells and optionally determining cell indices from impedance values to generate an impedance-based curve for each well; comparing the impedance-based curves and field potential curves between the first and second wells, and if significantly different, concluding that the transgene may affect at least one selected from the group consisting of cardiomyocyte viability, cardiomyocyte morphology, cardiomyocyte beating or affecting an electrophysiological property of the cardiomyoctye.

EXAMPLES

Example 1

Specifications of an Exemplary System for Electro-Stimulation, Impedance Measurement and Extracellular Recording A system was constructed for electro-stimulation of excitable cells, as well as for impedance measurement and extracellular recording of excitable cells having two electrodes for extracellular recording, and shared electrodes in the form of a pair of interdigitated electrode structures having a circle on line configuration that function both as electro-stimulation electrodes an impedance monitoring electrodes. The system was designed with the following specifications. The hardware system bandwidth was 1 Hz~2 KHz (−3 dB). The suppression ratio of impedance stimulation signal was >60 dB. The noise level was 10 µV (Vp-p). The system had excellent shielding and electromagnetic compatibility (EMC).

In regards to the electro-stimulation signal available waveforms are rectangular form, a ramp form, and sinusoidal. The polarity can be set for uni-polarity or bi-polarity. An exemplary amplitude is −2.5V~+2.5V@±100 mA per channel. An exemplary output voltage resolution is 2 mV. An exemplary rise time (10 to 90%) of voltage: 0.2 µs @ ΔU=2V. An exemplary time lag between stimulation and voltage output is 5±1 µs @ amplitude >200 mV. An exemplary current output is −250 mA~+250 mA@per channel. An exemplary resolution is 12 bit. An exemplary time resolution is 10 µS. A maximum frequency (rectangular waveform) is 50 KHz. A stimulation format can stimulate all 96 wells in 96 well plate simultaneously or by column (8 wells). Further, in some instances impedance and extracellular recording measurement could be conducted simultaneously with stimulation.

The sampling rate for impedance measurement over 96 wells was <10 ms. The sampling rate for extracellular recording signal was 1 KHz, 2 KHz, 5 KHz, and 10 KHz. Maximal sampling channels for ECR signal was maximally 8 channels (wells) in parallel, recorded from either one of two electrocellular recording electrodes in a single well.

Data acquisition mode permits extracellular recording only, impedance measurement only, and extracellular recording and impedance measurement simultaneously.

A gain setting offers 1 K, 2 K, 4 K, and 8 K. ADC resolution is 14 bit/±5V, total AD conversion rate of 800K SPS. Temperature rise in a well was lower than 0.4 C temperature rise compared to incubator temperature. DC offset is fixed at 0.05 Hz, ±1 mV. Input voltage range is ±2.5 mV. Electrode input impedance of gold having a diameter 60 µm/100 µm is <300 KΩ/1 KHz Example 2

Figure 6A:
FIGS. 6A-B show results from extracellular recording of field potential and impedance monitoring of HL-1 cells (FIG. 6A) and CorAT cells (FIG. 6B).

Monitoring the Spontaneous Field Potential Firing and Changes in Impedance of Cultured Cells HL-1 atria cells were harvested and cultured in wells having a pair of extracellular recording electrodes. FIG. 6A shows results from eight paralleled ECR signals in the HL-1 atria cells at day 7 with 40,000 cells per well, some channels showed spontaneous field potential (FP) firing but no impedance (IMP) signals. As can be seen, the firing is not paced at a regular rate.

Figure 6B:
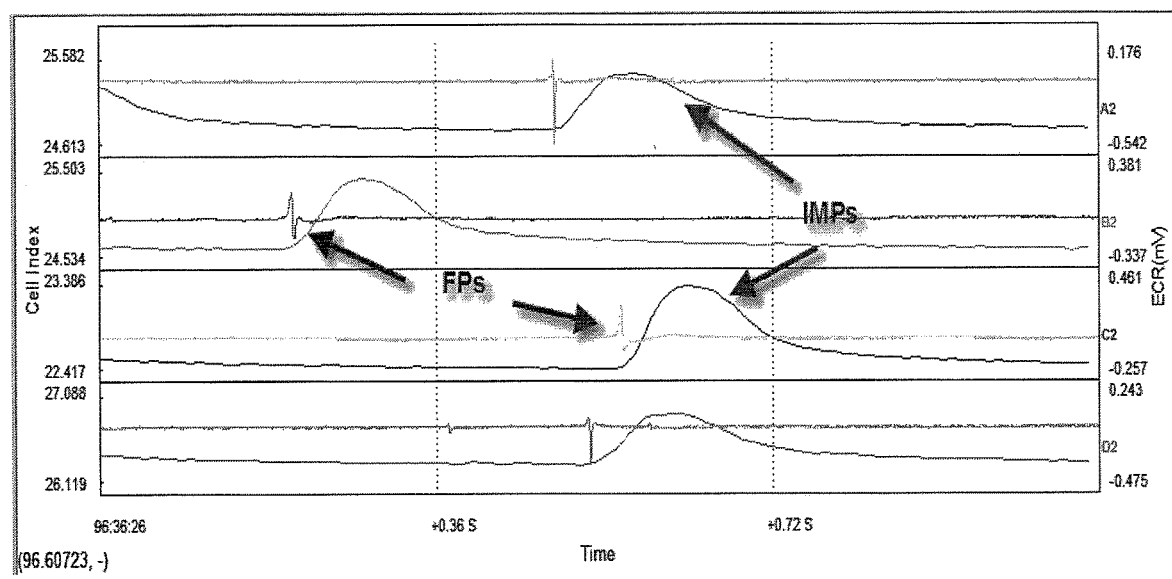

CorAT cells (mouse embryonic stem cell derived cardiomyocytes) were cultured over time. At day 6, with a cell density at 45,000 per well, spontaneous field potentional (FP) firing was detected as well as changes in impedance (IMP) as shown in FIG. 6B.

While the above experiments demonstrate the usefulness of ECR and impedance monitoring of cells, spontaneous firing and impedance changes were detected at different time points across different samples Example 3

Figure 7A:
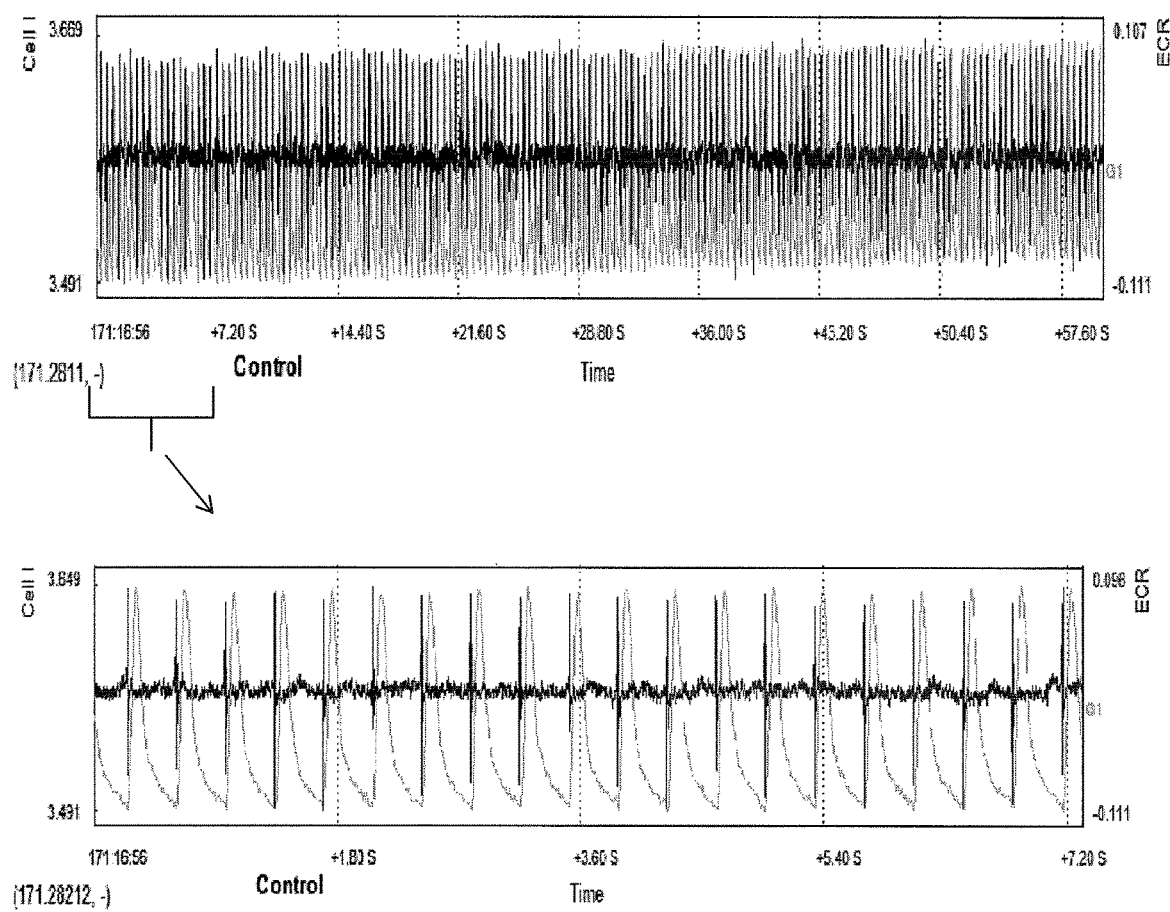
FIGS. 7A-C show results from extracellular recording of field potential and impedance monitoring of CorAT cells with the addition of Solatol at 0 µM (FIG. 7A), 200 µM (FIG. 7B) or 400 µM (FIG. 7C).
Figure 7B:
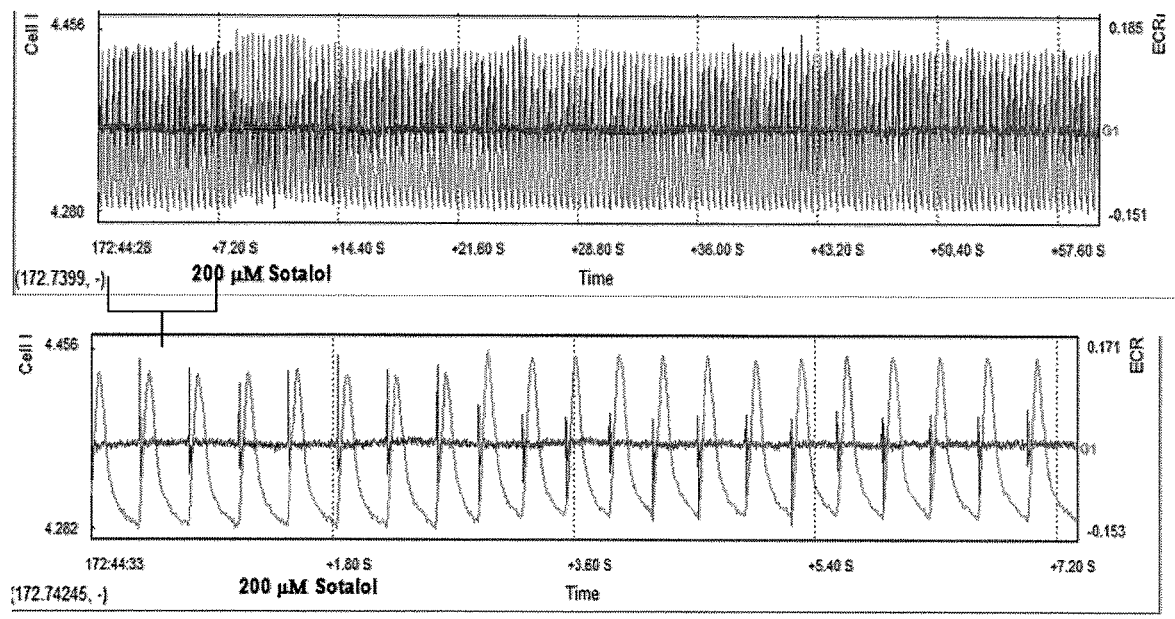
Figure 7C:
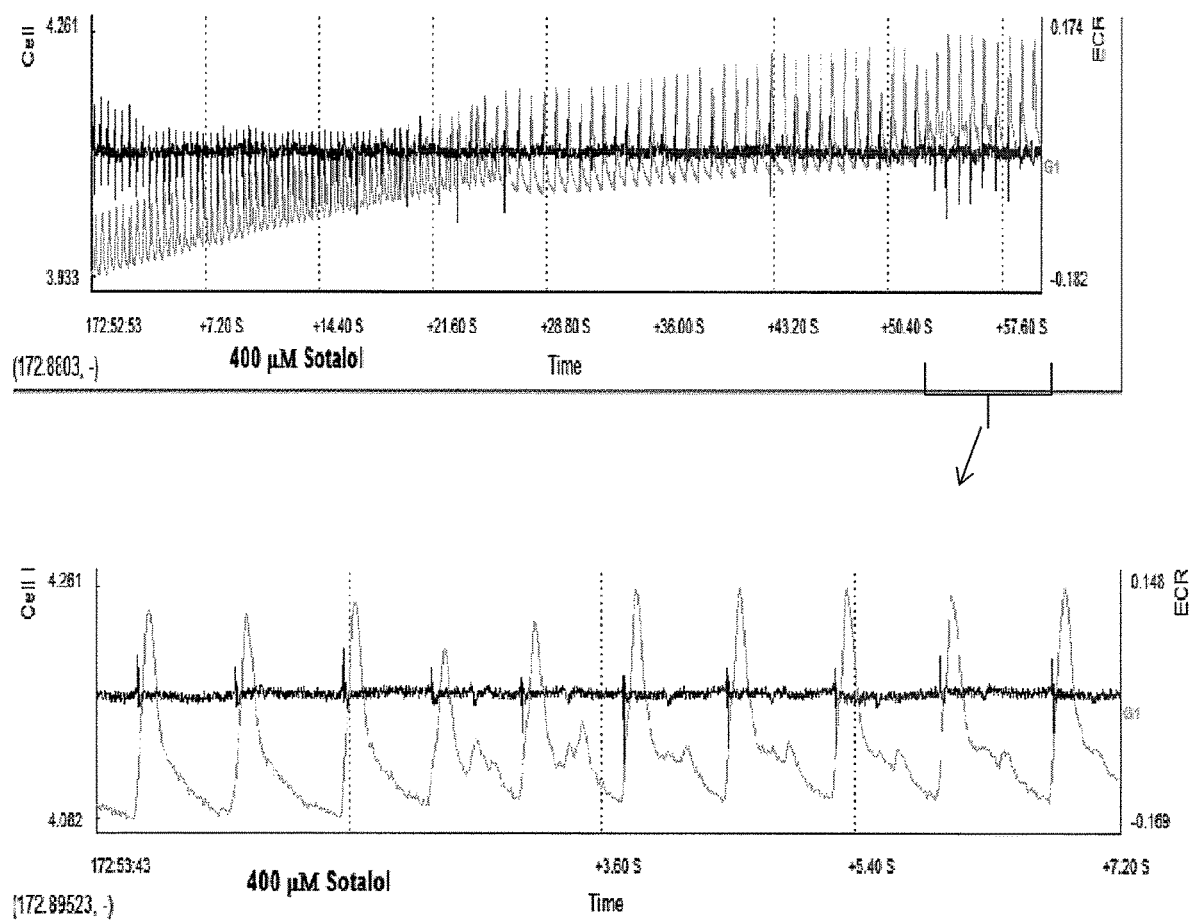

Modulation of Ion Channels while Performing Extracellular Recording and Impedance Monitoring CorAt cells were cultured over time and ECR and IMP signals were recorded simultaneously. Different doses of Sotalol were added at day 9 with CorAt cells at a density of 40,000 cells per well. FIGS. 7B-C show results from 200 µM and 400 µM. FIG. 5A is control without Sotalol, FIG. 5B shows treated wells or test wells with 200 µM, and FIG. 5C shows treated wells or test wells with 400 µM.

Administration of 400 µM sotalol induced a typical EAD and arrythmias which indicating the primarily target of sotalol is the IKr (hERG) as it was well characterized and published in literature. The other ion channels (INa and ICa) were secondarily inhibited; this may due the delay of recovery of membrane potential repolarization, so the available portion of excitable INa and ICa channels were reduced.

Figure 8A:
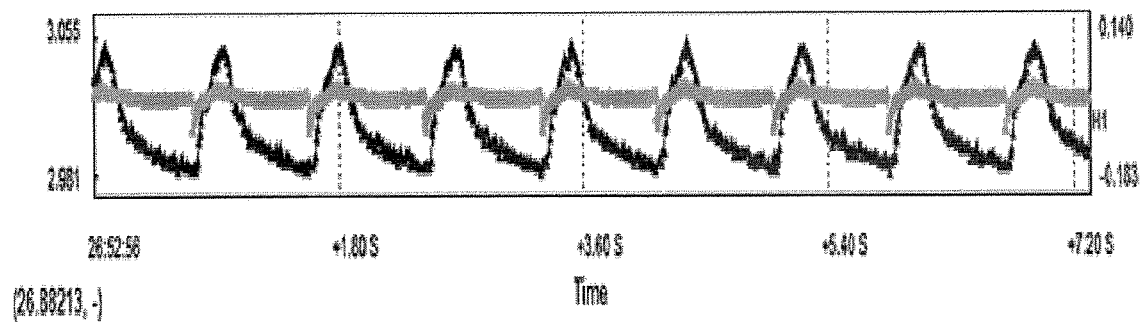
FIGS. 8A-F show results from extracellular recording of field potential and impedance monitoring of rat primary cardiomyocyte cells with the addition of Quinidine at 0 µM (FIG. 8A), 2 µM (FIG. 8B), 4 µM (FIG. 8C), 8 µM (FIG. 8D) or 16 µM (FIG. 8E).
Figure 8B:
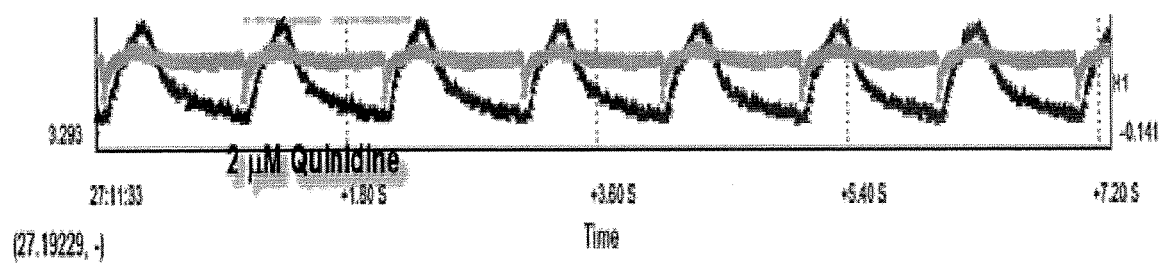
Figure 8C:
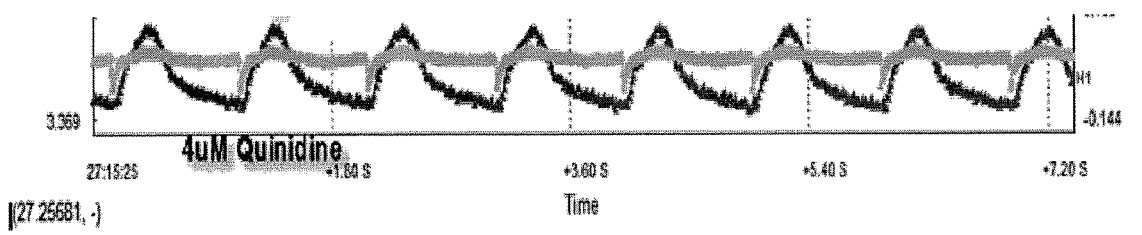
Figure 8D:
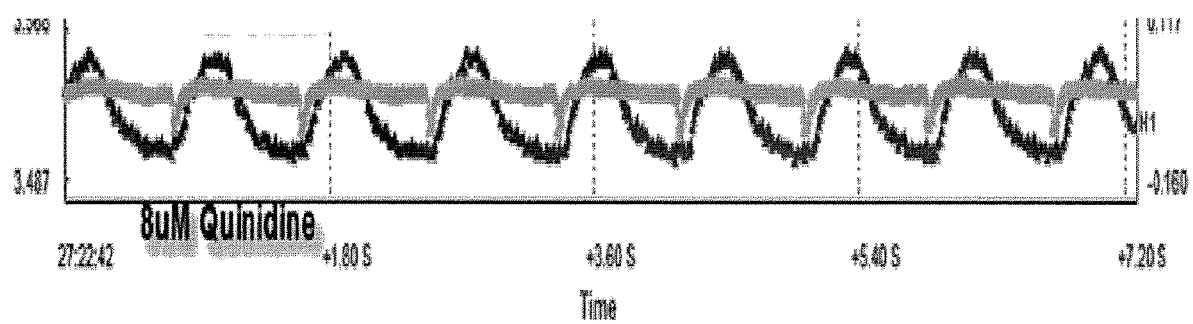
Figure 8E:
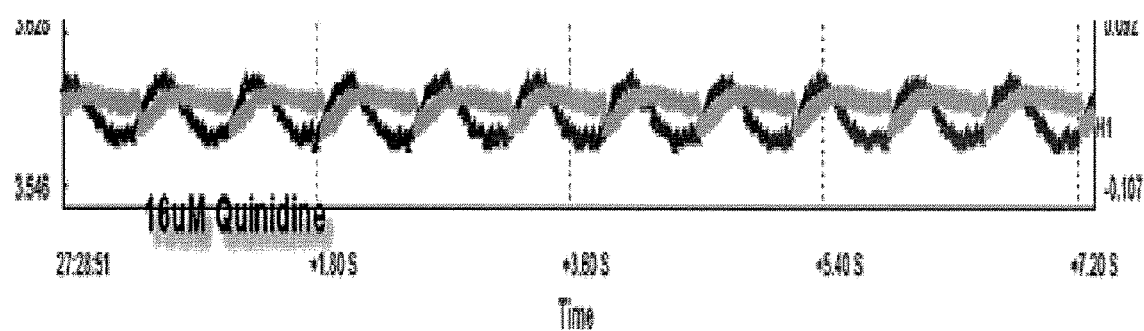
Figure 8F:
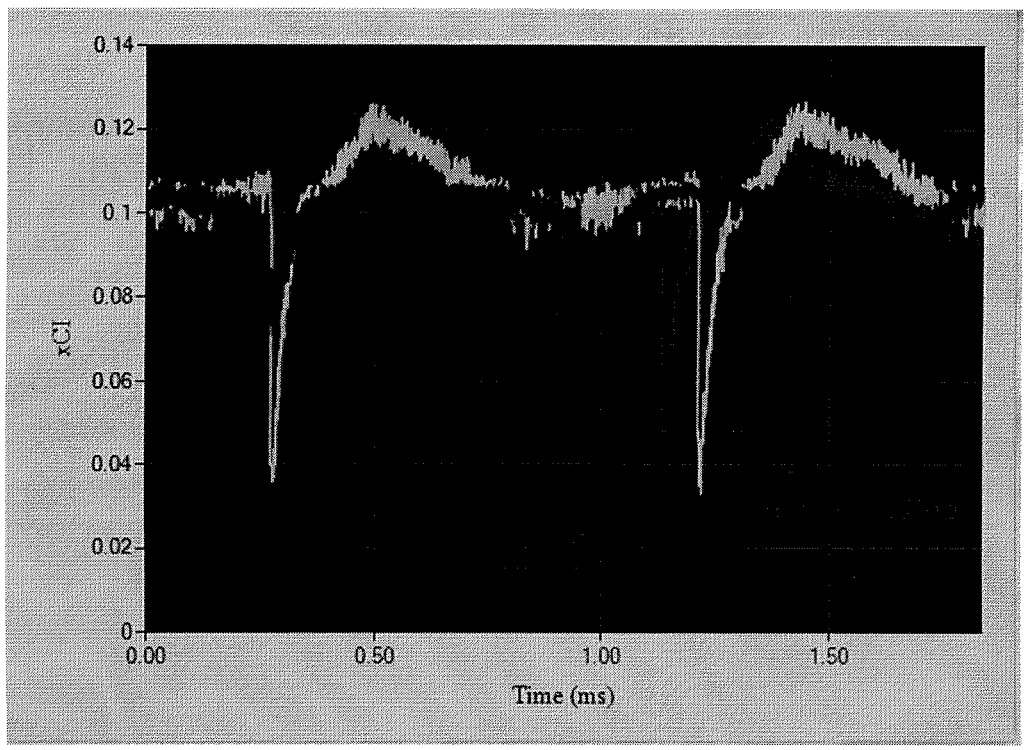
Figure 8G:
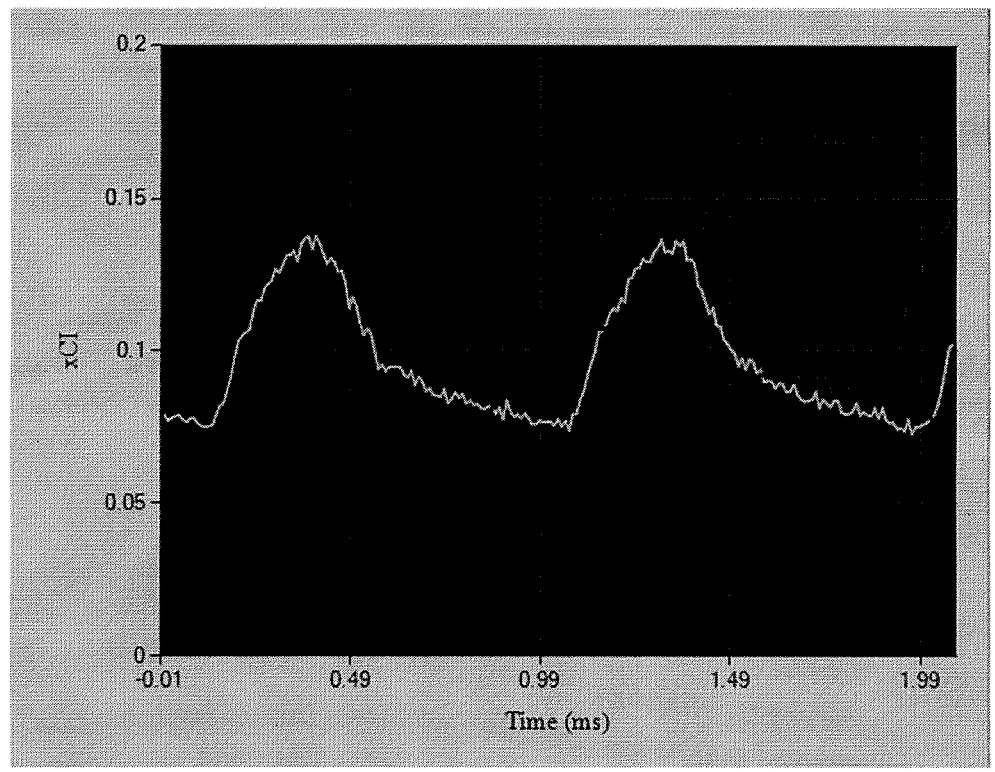
FIG. 8G shows an overlay of an interval of impedance from each of FIGS. 8A-E.

Primary rat cardiomyocytes were cultured over time and ECR and IMP signals were recorded simultaneously. Different doses of Quinidine were added at day 2 with the cardiomyocytes at 20,000 cells per well. FIG. 8A shows an ECR and IMP overlay with Quinidine added at 0 µM. FIG. 8B shows an ECR and IMP overlay with Quinidine added at 2 µM. FIG. 8C shows an ECR and IMP overlay with Quinidine added at 4 µM. FIG. 8D shows an ECR and IMP overlay with Quinidine added at 8 µM. FIG. 8E shows an ECR and IMP overlay with Quinidine added at 16 µM. FIG. 8F shows an ECR overlay of from FIGS. 8A-E. FIG. 8G shows an overlay of impedance-based curves of FIGS. 8A-E.

Example 4

Field Stimulation and Pacing of Mouse Embryonic Stem Cell Derived Cardiomyocytes (Cor.AT) Using the RTCA Cardio-ECR System Cor.AT cells are mouse embryonic stem cell derived cardiomyocytes that are engineered to express the GFP protein and puromycin protein for selection. These cells are a 100% pure population of cardiomyocytes that beat spontaneously in culture and express all the repertoire of ionic currents typical of a normal cardiomyocytes such as calcium, potassium and sodium.

To assess the field stimulation and pacing of Cor.AT cells, the cells were seeded in the wells of Cardio-ECR plates coated with fibronectin at 10 ug/mL and at a density of 35,000 cells/well. This density has been empirically optimized to sustain a cell monolayer that can beat in a synchronous manner. The cells were allowed to form a monolayer and the media was changed to fresh media on daily basis. On the $9^{th}$ day after seeding the cells were subjected to field stimulation. The cardiomyocytes were field stimulated at 1.2 second duration with a biphasic pulse of 1 ms total length and an output voltage of 1.05 V. The total duration of stimulation was for 40 seconds.

Figure 9:
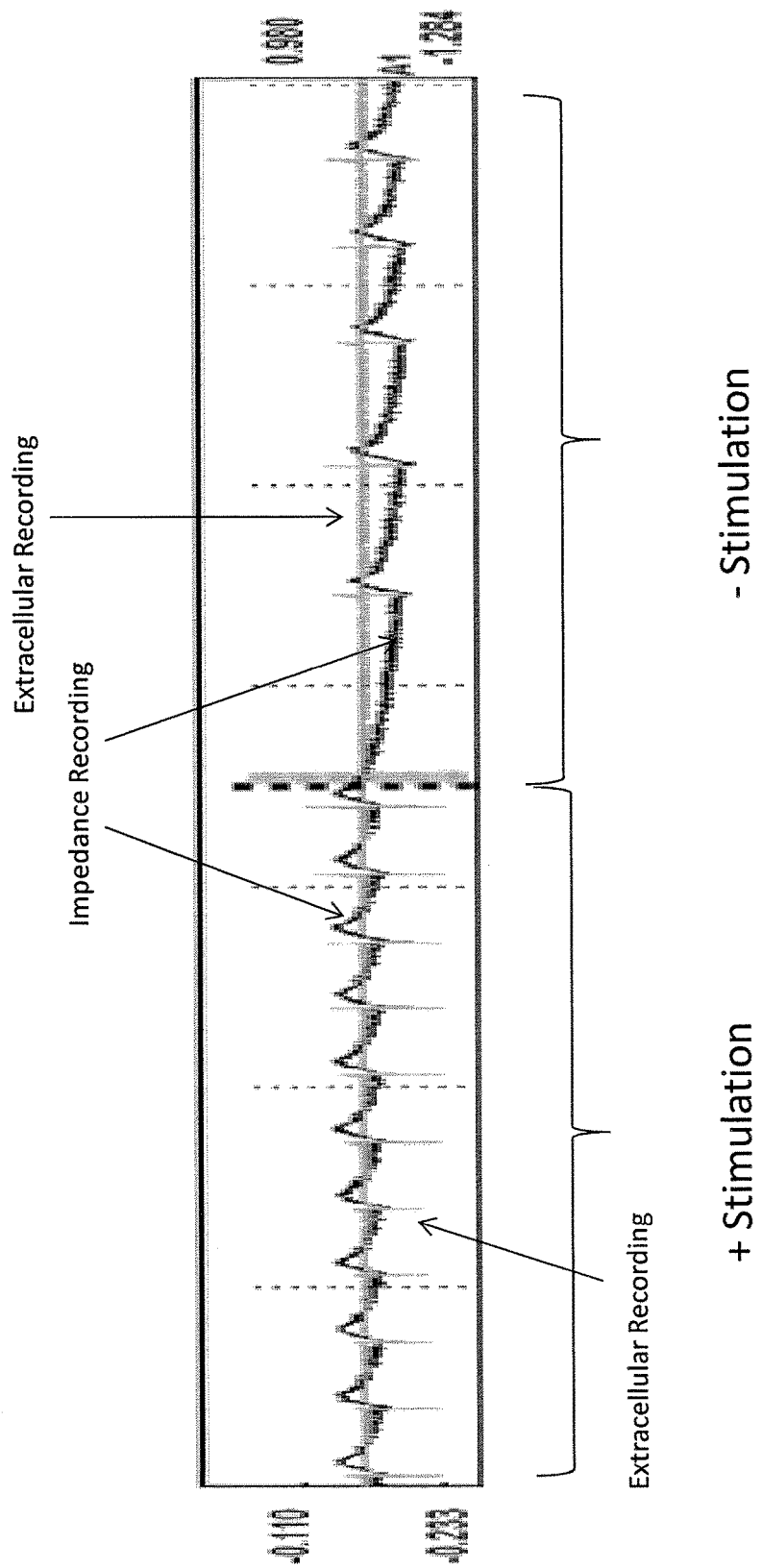
FIG. 9 shows changes in impedance and extracellular recording of field potential of Cor.AT cells during electro-stimulation and without electrostimulation.

Both the field potential and impedance signals were dynamically monitored by the Cardio-ECR System. As shown in FIG. 9, application of the stimulation pulse caused regular pacing of the Cor.AT cells as measured primarily by the impedance signal (Red Trace) which signifies contraction of the cardiomyocytes. The actual ECR signal during the stimulation phase (Blue Trace) is overwhelmed by the field stimulation signal but can be observed when there is no stimulation.

Example 5

Field Stimulation and Pacing of Rat Neonatal Cardiomyocytes Using the RTCA Cardio-ECR System Rat neonatal primary cardiomyocytes are spontaneously beating cardiomyocytes that are used as a model system for studying heart function. This model is well-established for the study of the transport and toxicity of drugs and electro-physiological characterization. Neonatal rat cardiomyocytes are prepared and harvested as follows:

Briefly, hearts from neonatal rats are rapidly excised and washed to remove blood and debris. The ventricles are carefully minced and dissociated into single cells by proteolytic enzymes during repetitive digestions with gentle stirring. Suspending cells in serum containing growth medium terminate the proteolytic digestion. Primary cardiomyocytes are purified and enriched by pre-plating twice for 45 minutes each time. The cells are counted and adjusted to a desirable concentration and then directly seeded in the wells of the Cardio-ECR Plates coated with 0.1% gelatin at a density of 14,000 cells/well. This density has been empirically optimized to sustain a cell monolayer that can beat in a synchronous manner. The cells were allowed to form a monolayer and the media was changed to fresh media on daily basis. On the $5^{th}$ day after seeding the cells were subjected to field stimulation. The cardiomyocytes were field stimulated at 0.8 second duration with a biphasic pulse of 1.0 ms total length and an output voltage of 1.2V.

Figure 10:
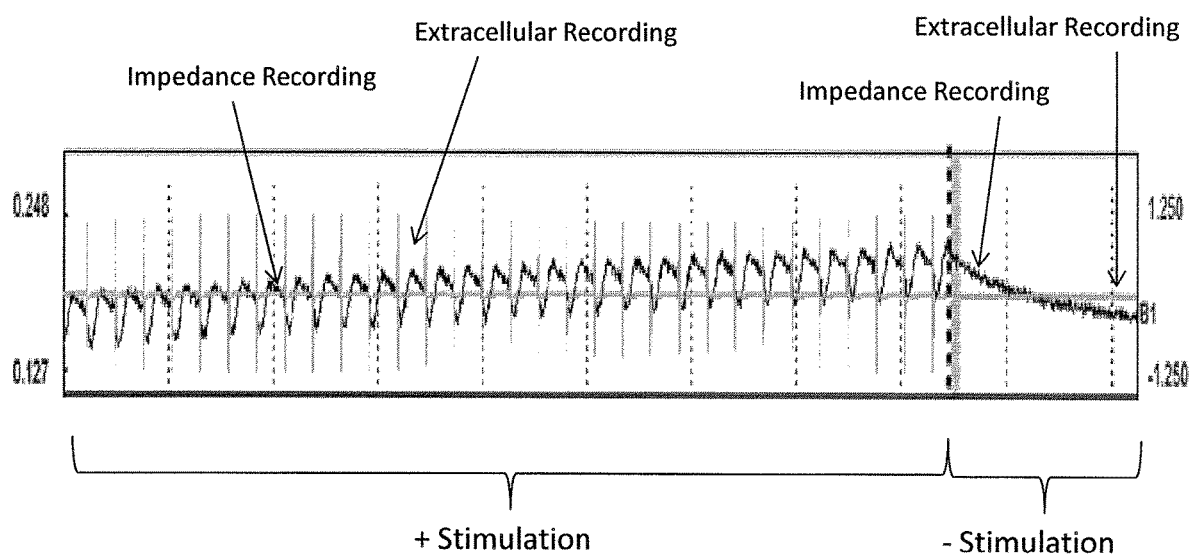
FIG. 10 shows changes in impedance and extracellular recording of field potential of reat primary cardiomyocyte during electrostimulation and without electrostimulation.

Both the field potential and impedance signals were dynamically monitored by the Cardio-ECR System. As shown in FIG. 10, application of the stimulation pulse caused regular pacing of the rat neonatal primary cells as measured primarily by the impedance signal (Red Trace) which signifies contraction of the cardiomyocytes. The actual ECR signal during the stimulation phase (Blue Trace) is overwhelmed by the field stimulation signal but can be observed when there is no stimulation.

Example 6

Figure 11A:
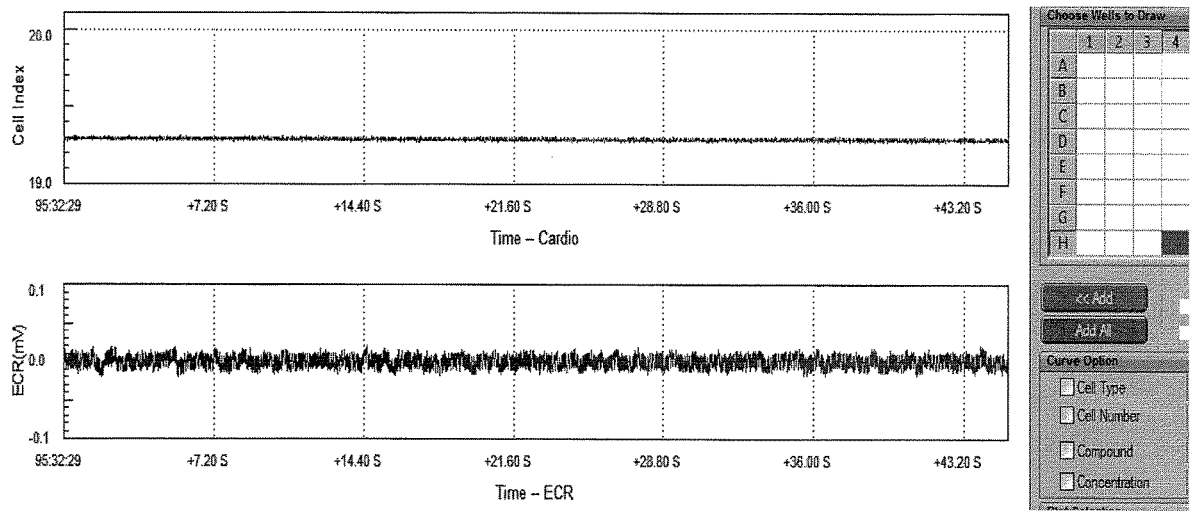
FIGS. 11A-F shows a series of curves from an experiment where HL-1 cells (FIG. 11A), were electro-stimulated to induce measurable changes in field potential (FP) (FIG. 11B), which could then be modulated through the addition of different concentrations of the calcium channel blocker Israpidine (FIGS. 11C-E).
Figure 11B:
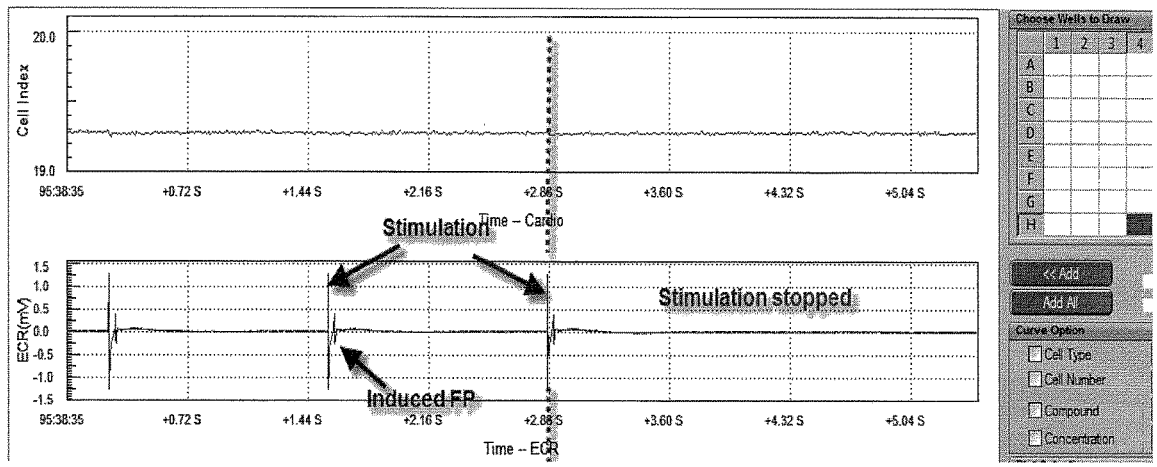

Electro-Stimulation Coupled with Extracellular Recording Shows Change in Field Potentials when Adding Different Concentrations of the Calcium Channel Blocker Isradipine To show the benefit of coupling electro-stimulation with extracellular recording, impedance and extracellular recording measurements were performed on HL-1 cells. Electro-stimulation was then applied at electro-stimulation parameters of 1.1 V intensity, 1 ms pulse width, 1.3 s stimulation interval. As shown in FIG. 11A, prior to electro-stimulation, the HL-1 cells showed no measureable changes in impedance (IMP) or extracellular recording field potential (FP); however, FIG. 11B shows electro-stimulation induced FP in the extracellular recording measurement and thus a "waking up" of the cells.

Figure 11C:
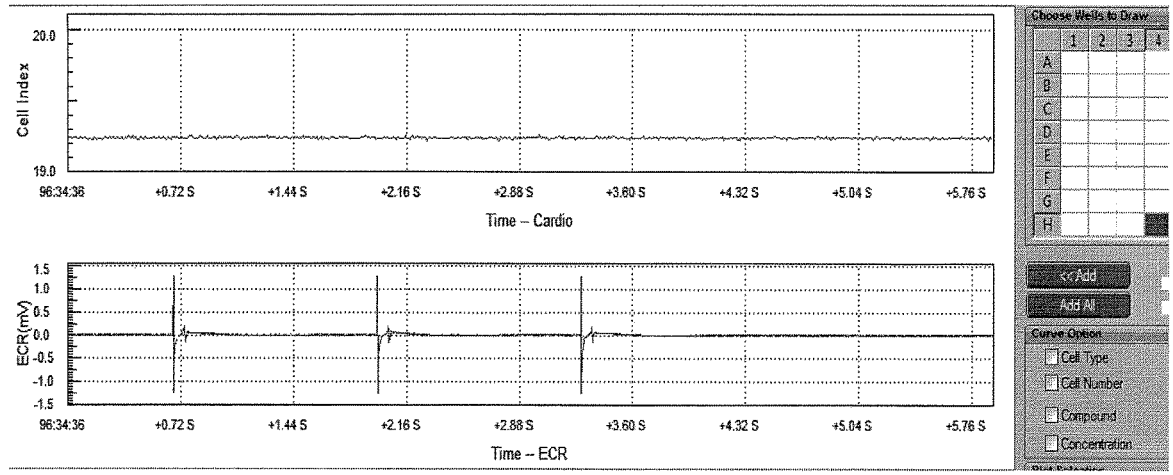
Figure 11D:
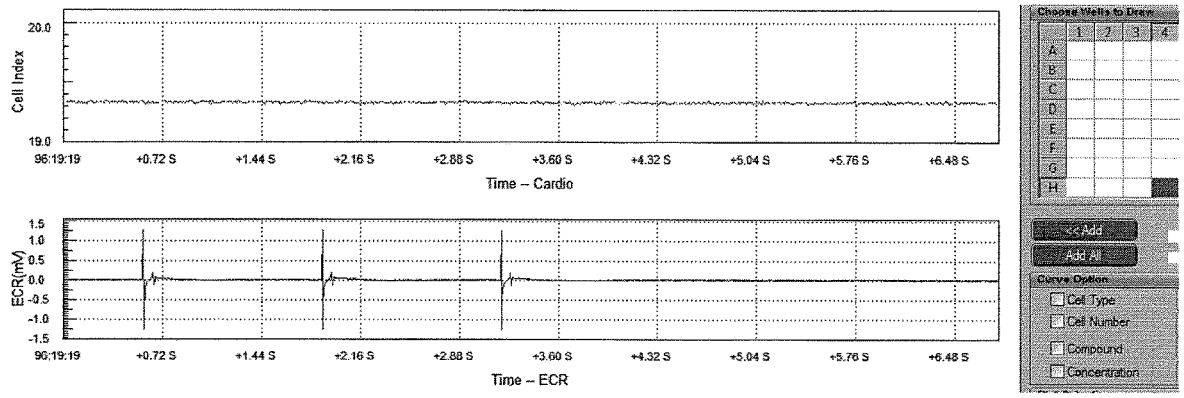
Figure 11E:
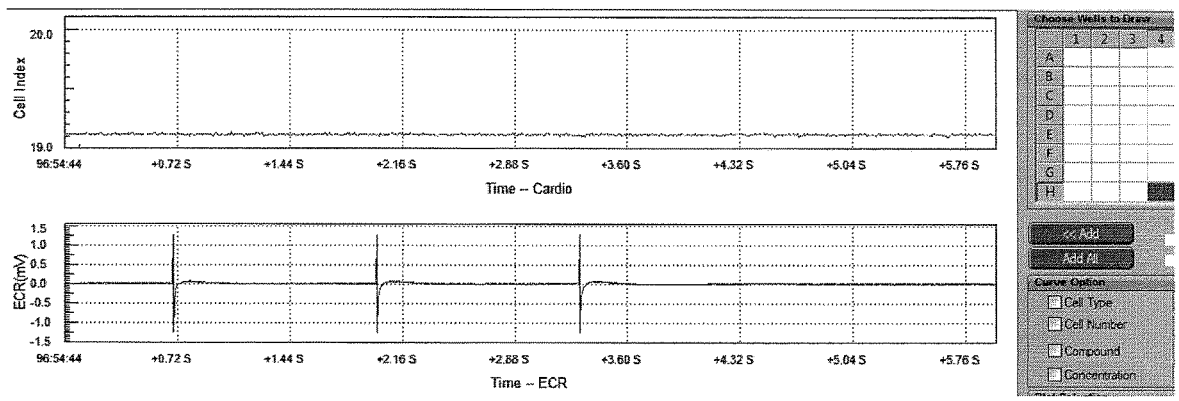
Figure 11F:
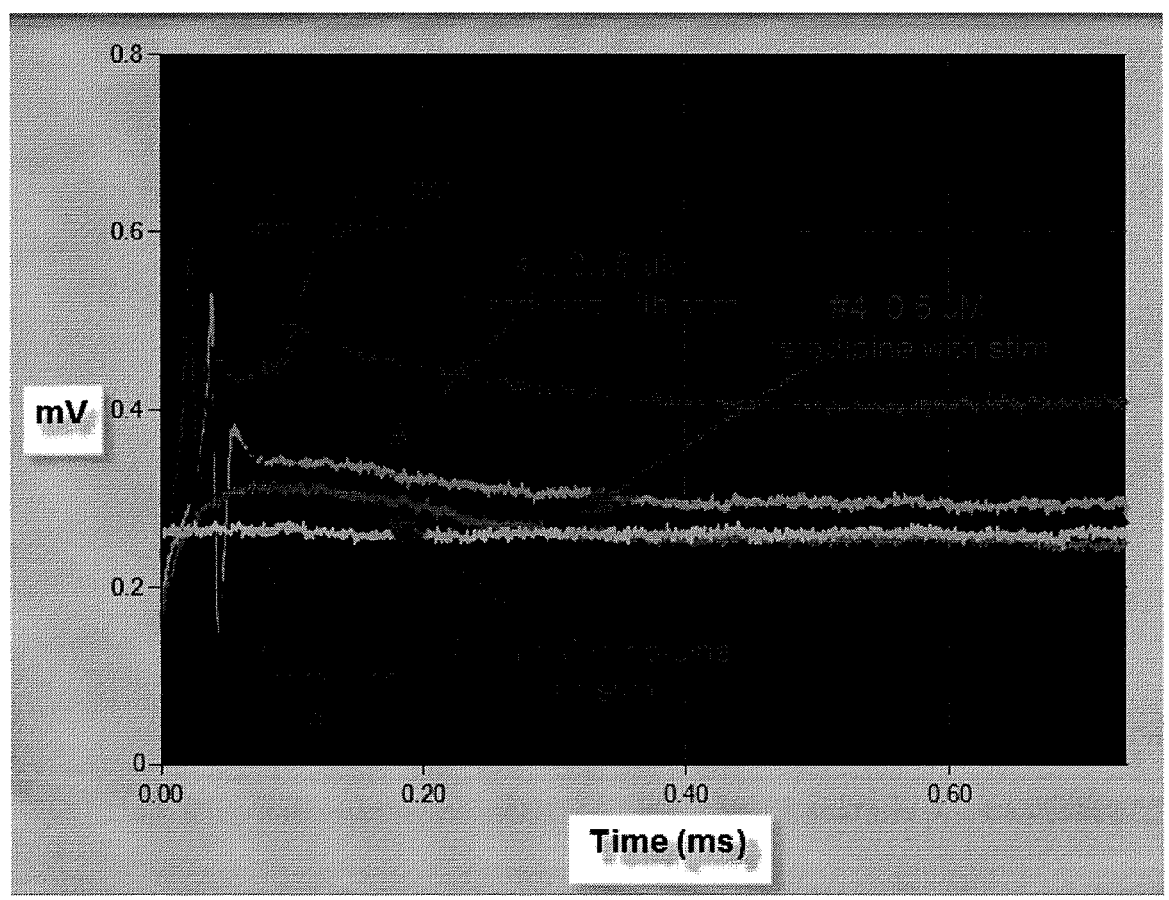

Cells were then treated with Isradipine, a L type $Ca^{2+}$ channel blocker at either 0.25 µM (FIG. 11C), 0.5 µM (FIG. 11D), or 1 µM (FIG. HE). FIG. 11F shows an overlay of the extracellular recording field potentials. By application of the different doses of isradipine, the slow component of the induced FP (Ca channel) was gradually inhibited.

Example 7

Figure 12A:
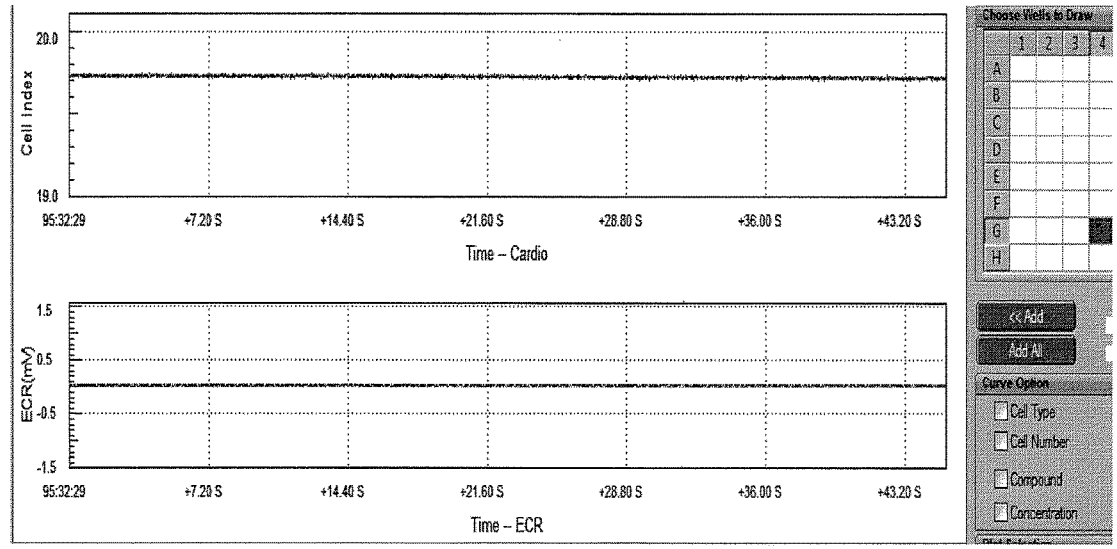
FIGS. 12A-G show a series of curves from an experiment where HL-1 cells (FIG. 12A) where electrostimulated to induce measureable changes in field potential (FP) (FIG. 12B). A calcium channel activator was added to culture and modulation of the field potential (FP) was detected (FIG. 12C). The culture was paced use electro-stimulation (FIG. 12D). Addition of different concentrations of antagonist (FIGS. 12E-F) were added and modulated the field potential (FP).
Figure 12B:
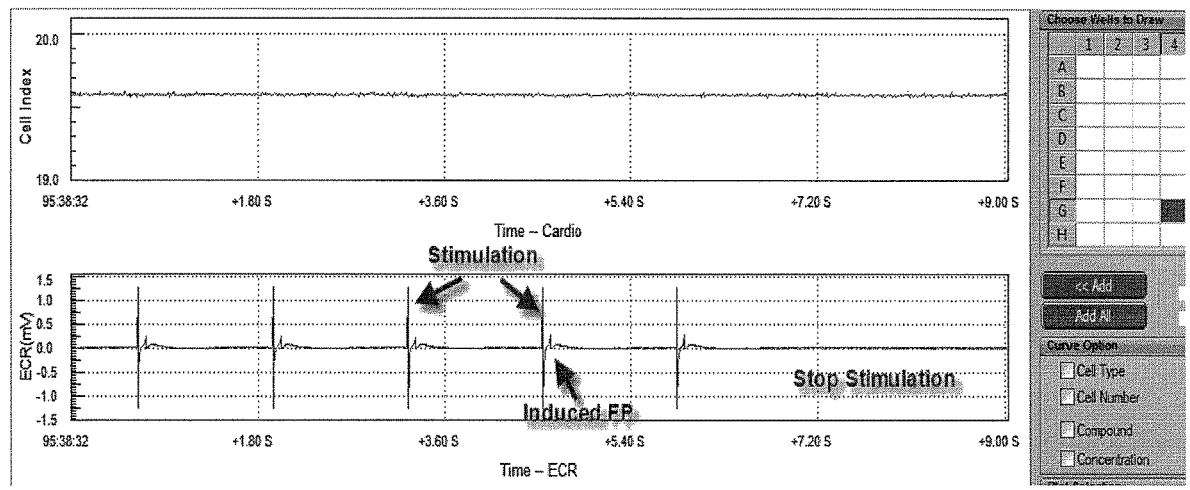

Electro-Stimulation Coupled with Extracellular Recording Shows Change in Field Potentials when Adding Different Concentrations of the Calcium Channel Activator Bay K8644 and Addition of Antagonist As another example demonstrating the benefit of coupling electro-stimulation with extracellular recording, impedance and extracellular recording measurements were performed on HL-1 cells. HL-1 cells were cultured on a device having a pair of electro-stimulation electrodes, a pair of impedance measurement electrodes and a recording and reference electrode pair. Electro-stimulation was then applied at electro-stimulation parameters of 1.1 V intensity, 1 ms pulse width, 1.3 s stimulation interval. As shown in FIG. 12A, prior to electro-stimulation, the HL-1 cells showed no measureable changes in impedance (IMP) or extracellular recording field potential (FP); however, FIG. 12B shows electro-stimulation induced FP in the extracellular recording measurement and thus a "waking up" of the cells followed by lack of FP after stopping electro-stimulation.

Figure 12C:
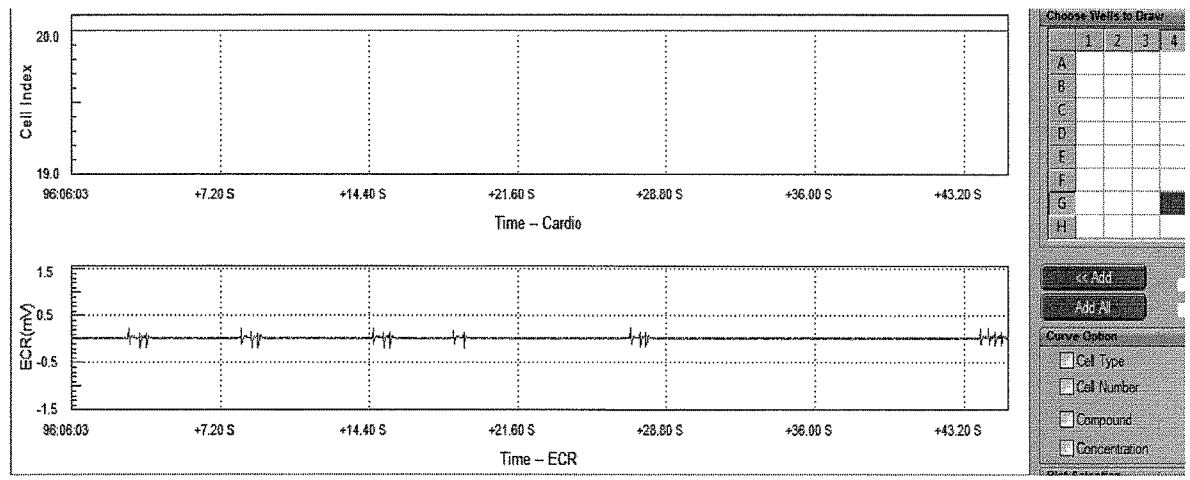
Figure 12D:
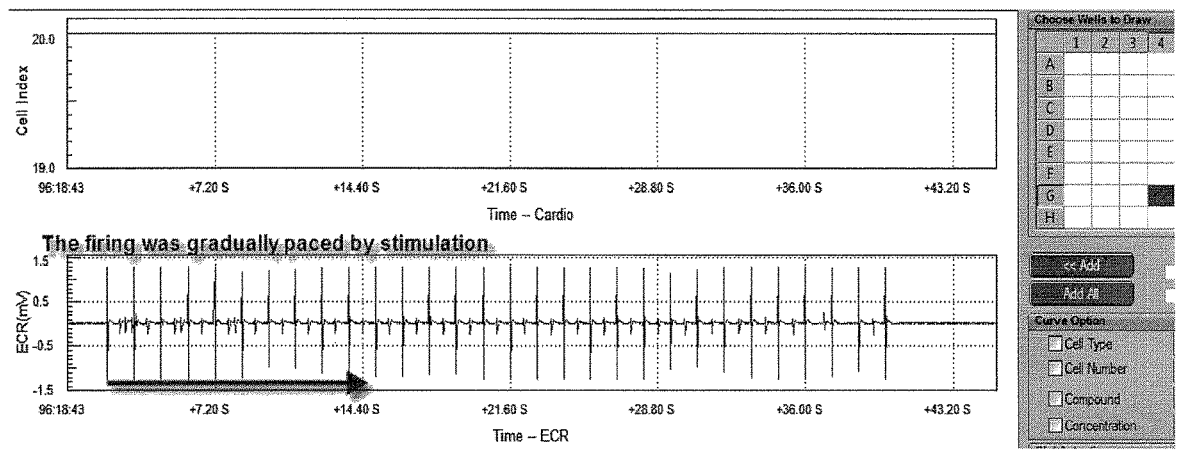

Cells were then treated with Bay K8644, a L type calcium channel activator at 1 µM (FIG. 12C). The spontaneous firing rate was increased due to K8644 application, but its firing is irregular. The cells were then electro-stimulation to pace the firing with the K8644 still in the medium using the electro-stimulation parameters of 1.1 V, 1 ms, 1.3 s as shown in FIG. 12D. The spontaneous firing rhythm was gradually adapted to the stimulation frequency.

Figure 12E:
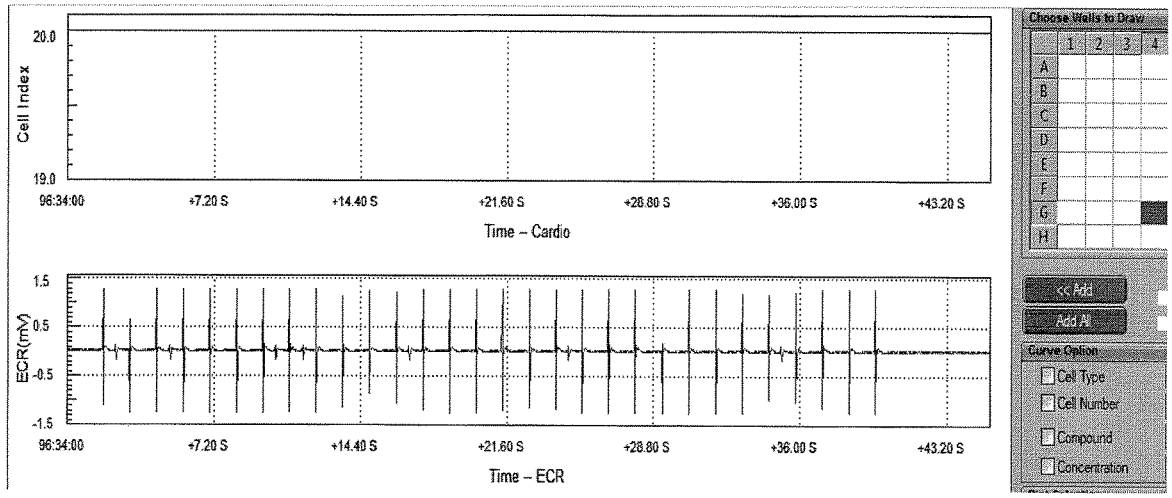
Figure 12F:
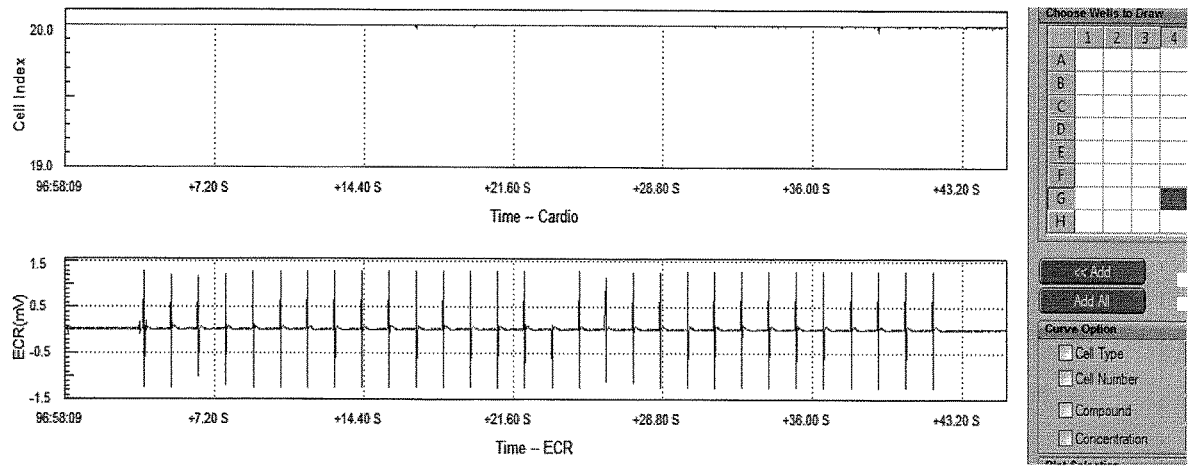
Figure 12G:
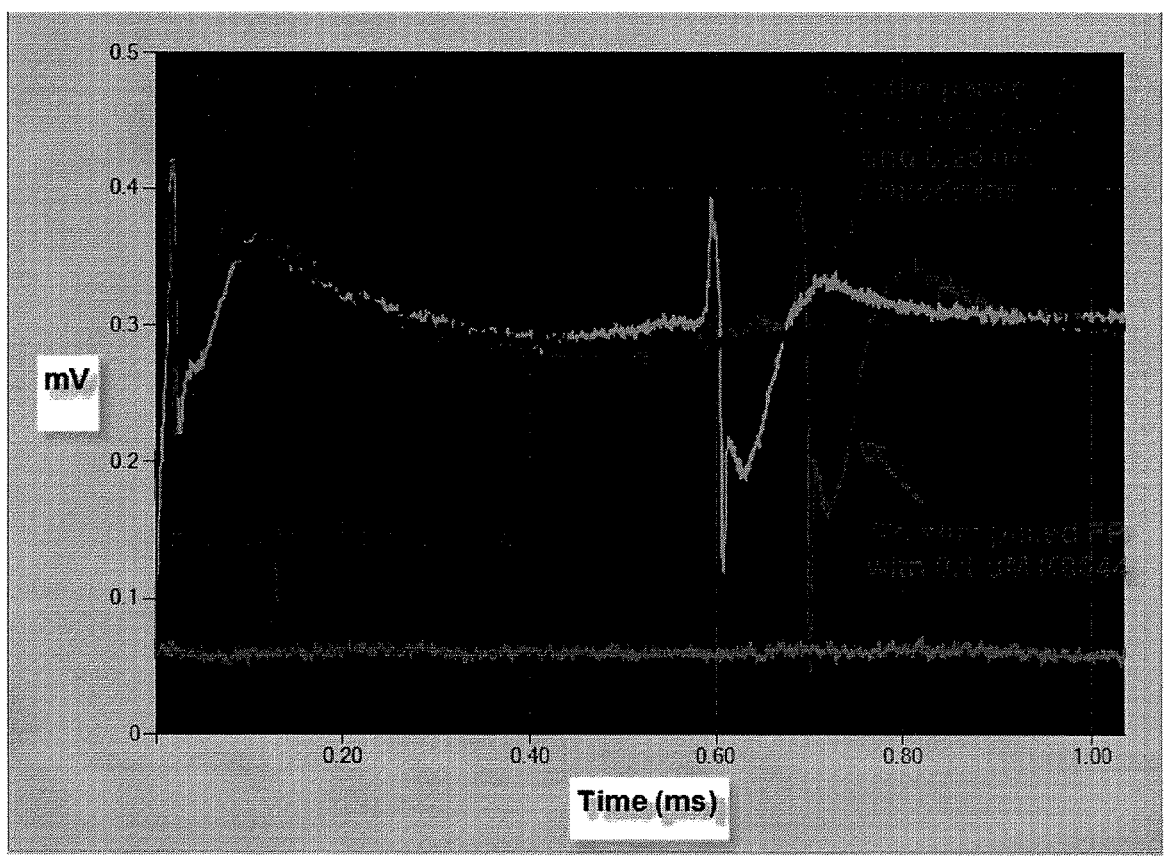

Cells were then treated with Nifedipine to antagonize the effect of Bay K8644 at either 0.25 µM (FIG. 12E) or 0.5 µM (FIG. 12F). The stimulation induced firing rate was remarkably inhibited due to nifedipine application. FIG. 12G shows the overlap of the field potential traces from FIGS. 12A-F. Based on the overlapped trace analysis, we can see that the FP was dose dependently inhibited by L type $Ca^{2+}$ channel blocker, Nifedipine, the inhibition effect was mainly attributed to the blocking the $Ca^{2+}$ peak (slow component followed by the initial fast $Na^+$ peak).

Example 8

Electro-Stimulation of CorAT Cells and the Pacing of Cardiomyocytes

Figure 13A:
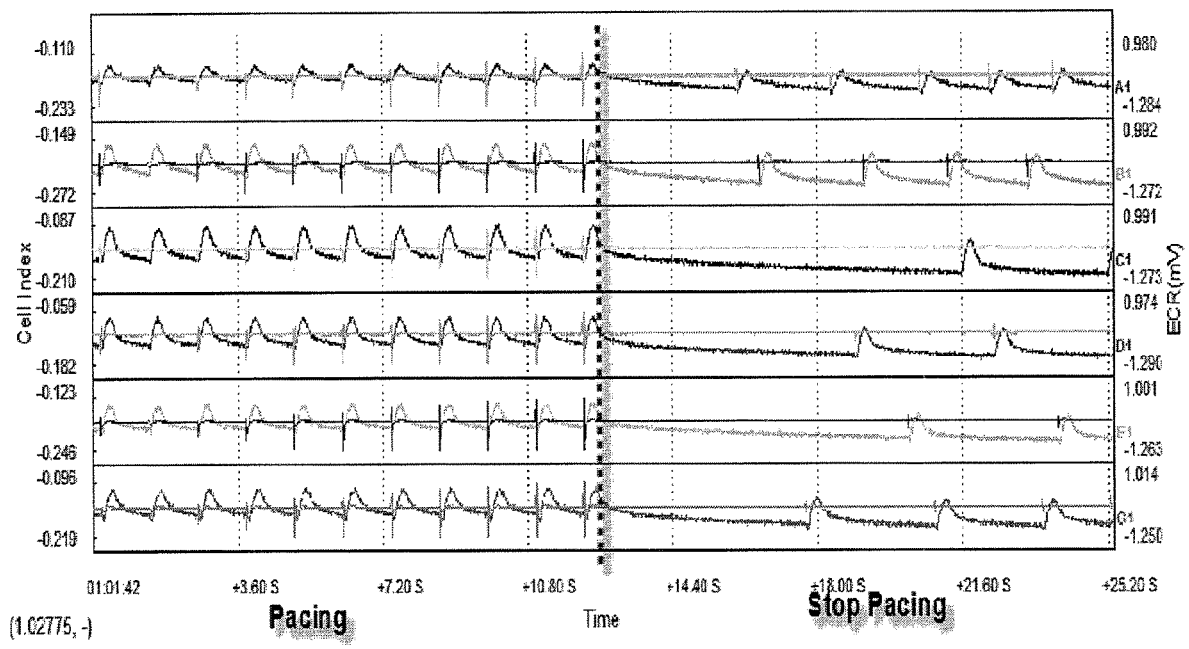
FIGS. 13A-C show a series of curves from an experiment documenting the electro-stimulation of CorAT cells and the pacing of cardiomyocytes where FIG. 13A overlays impedance (via cell index) and field potential in response to electro-stimulation and after electro-stimulation stops.
Figure 13B:
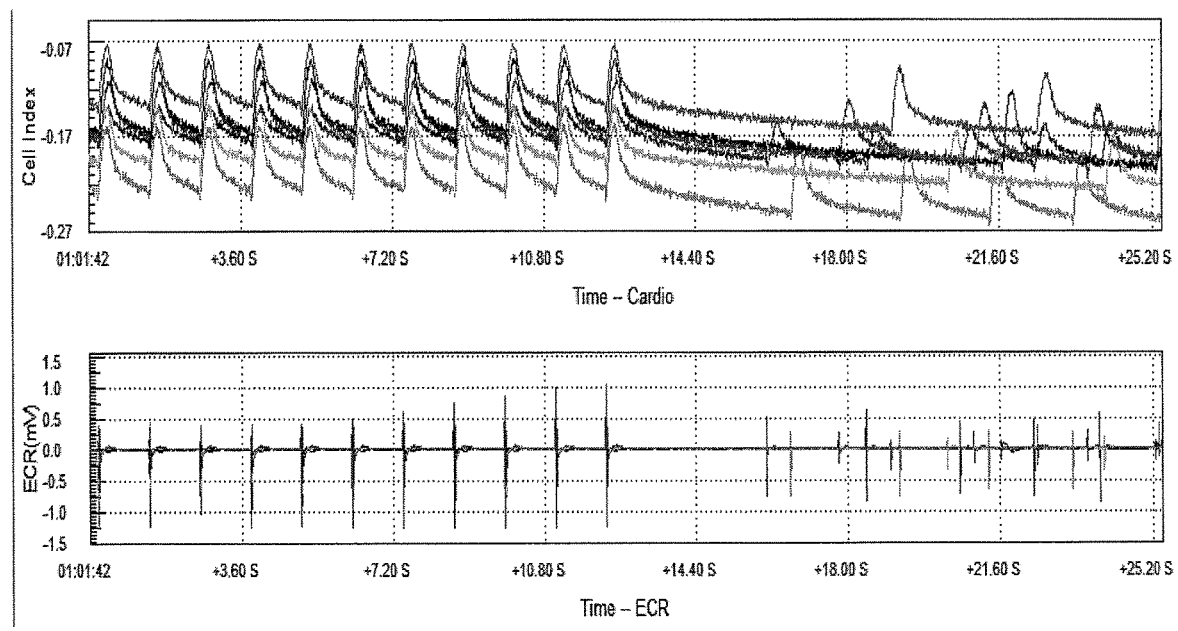

CorAT cells were cultured on a device having a pair of electro-stimulation electrodes, a pair of impedance measurement electrodes and a recording and reference electrode pair. At day 9 CorAT cells with a density of 35,000 per well were paced by applying 1.05 V at every 1.2 seconds for a duration of about 40 seconds. A shown in FIGS. 13A-B, pacing was induced to produce reproducible plots of both impedance (shown in cell index) and extracellular field potential; however, when pacing by electro-stimulation stopped, both impedance and field potential were irregular. In FIG. 13A, impedance and field potential are overlayed whereas in FIG. 13B impedance is the upper display and extracellular recording of field potential the lower.

Figure 13C:
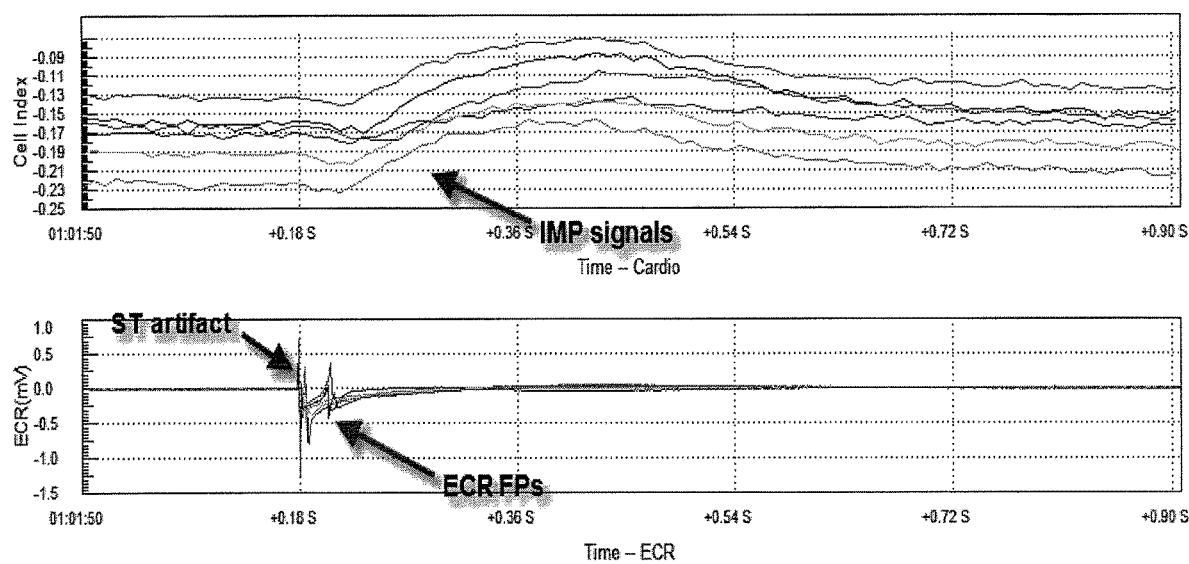

FIG. 13C shows a single interval of electro-stimulation showing a relationship between change in impedance (top) and extracellular recording field potential (lower)

Example 9

Electro-Stimulation of Rat Primary Cardiomyocytes and the Pacing of Cardiomyocytes Rat primary cardiomyocytes were harvested and cultured on a device having a pair of electro-stimulation electrodes, a pair of impedance measurement electrodes and a recording and reference electrode pair. At day 5, the cells had a cell density of 14K per well.

Figure 14A:
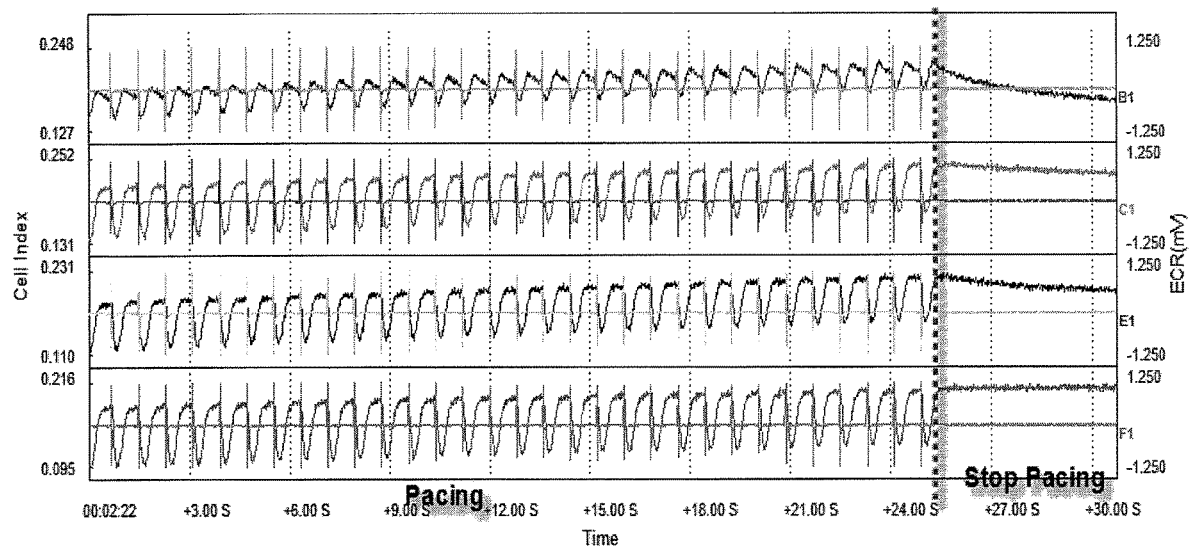
FIGS. 14A-B show the electro-stimulation of rat primary cardiomyocytes and the impedance and field potential profiles in response to the regular pacing of cardiomyocytes.
Figure 14B:
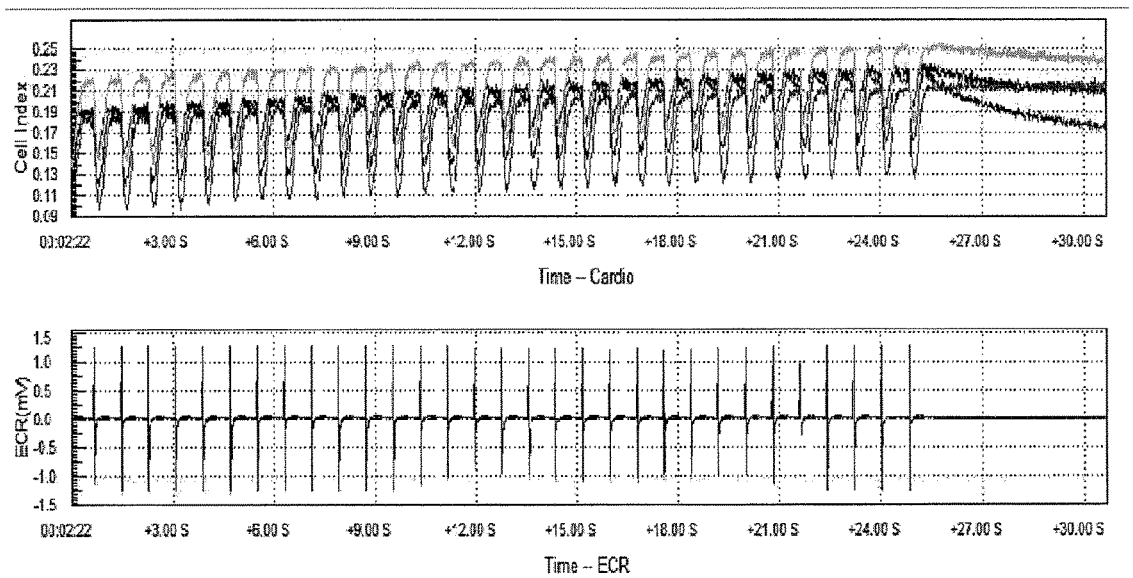

Cells were paced by applying electro-stimulation (1.2V, 1 ms, 0.8 s, stimulation duration: ~40 s). FIGS. 14A-B showed the regular pacing of the cardiomyocytes and the reproducible impedance and field potential responses; however, when pacing stopped the regular impedance and field potential profiles also stopped. FIG. 14A shows impedance as an overlay with field potential while FIG. 14B shows impedance on the top panel and field potential on the lower panel.

Example 10

Recording Neuronal Activity Through the Recording of Field Potential

Our cardio ECR device includes a pair of extracellular recording electrodes, the size of which resemble that of popular multichannel electrode recoding. We found that our electrode configurations could be used for recording of changes in field potential (FP) from cultured neuronal network (see example data below).

Dissociated neurons from brain or spinal tissue are seeded in the well of our cardio ECR device, and allowed to mature over the course of three weeks into self-organized networks complete with axons, dendrites and hundreds to thousands of synaptic connections. The neuronal networks exhibit spontaneous bursting activity after two weeks of incubation, and the spontaneous activity could be monitored by the either one of the two ECR electrodes.

Figure 15A:
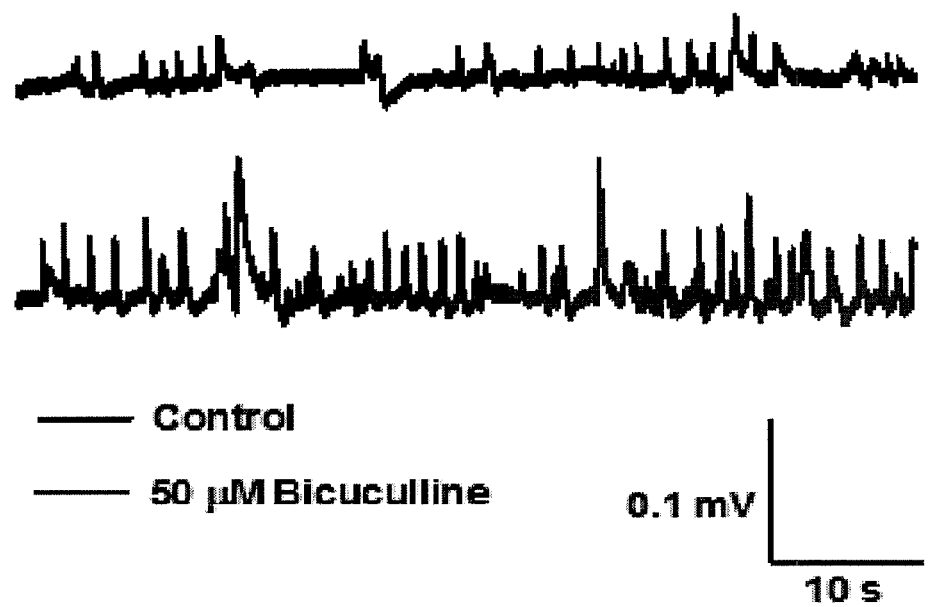
FIGS. 15A-B show results from experiments monitoring the field potential of neurons after treatment with bicuculline (FIG. 15A) or Glutamate (FIG. 15B).

The neuronal firing data was recorded by either one of the two ECR electrodes in single well. After performing measurements from the ECR electrodes, Bicuculline, a GABAAR inhibitor, was added to the culture. As shown in FIG. 15A, a remarkable increased the FP spontaneous firing frequency in cultured rat cortical neurons was measured on day three. This result is consistent with a previous publication that bath application of bicuculline caused large increases in spontaneous spike firing frequency (Ma Y L, Weston S E, Whalley B J, Stephens G J. The phytocannabinoid Delta(9)-tetrahydrocannabivarin modulates inhibitory neurotransmission in the cerebellum. Br J. Pharmacol. 2008 May; 154(1):204-15.

Figure 15B:
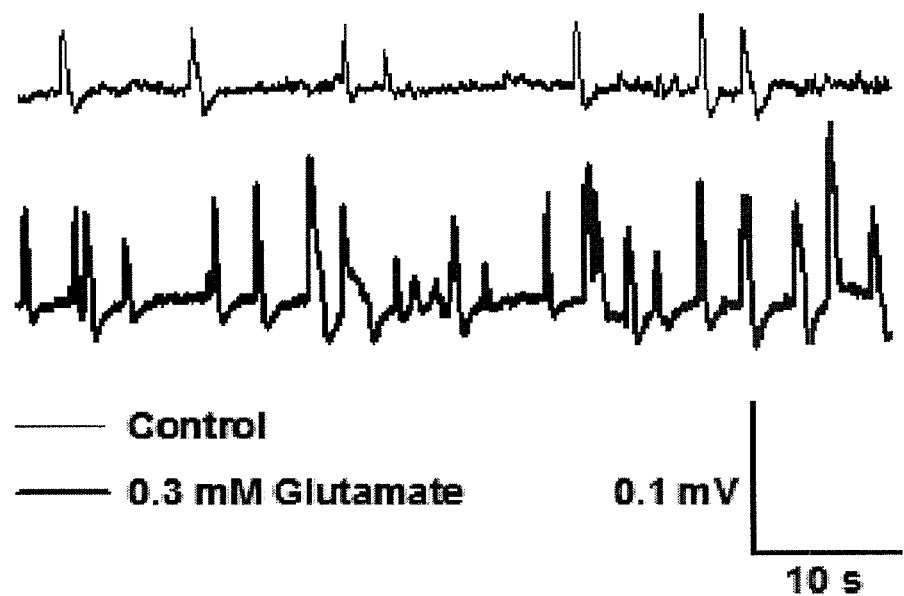

As a complementary experiment, Glutamate was added to the culture rat cortical neurons and the field potential monitored. As shown in FIG. 15B, Glutamate, a non-selective GluR agonist remarkably increased the FP spontaneous firing amplitude and frequency in rat cultured cortical neurons on day ten.

What is claimed is:

1. A method for monitoring excitable cells, the method comprising:
  a) providing a system for monitoring excitable cells, the system comprising a device comprising at least one well, each well having a bottom comprising a nonconductive substrate, wherein the substrate has a surface suitable for attachment of excitable cells; a power source configured to deliver an electrical signal capable of electro-stimulating excitable cells; and an impedance analyzer that resolves consecutive cell-substrate impedance measurements within 10 milliseconds apart, wherein each well comprises:
    i) a pair of electro-stimulation electrodes configured to receive the electrical signal from the power source thereby delivering an electro-stimulating signal to the well for electro-stimulation of excitable cells attached to the substrate; and
    ii) a pair of impedance monitoring electrodes communicatively coupled to the impedance analyzer permitting cell-substrate impedance monitoring of excitable cells attached to the substrate at 10 millisecond time resolution;
  b) adding a sample of cardiomyocyte or cardiomyocyte precursor cells to the device;

c) electro-stimulating the cells to affect cell beating;
d) adding a compound to the well;
e) impedance monitoring the electro-stimulated cells at 10 millisecond time resolution; and
f) assessing the effect of compound administration on cell beating.

2. The method according to claim 1, wherein the compound's effect on cell beating is assessed by determining a change in beating cycle in response to the addition of the compound.

3. A method for monitoring excitable cells, the method comprising:
a) providing a system for monitoring excitable cells comprising a device comprising at least one well, each well having a bottom comprising a nonconductive substrate, wherein the substrate has a surface suitable for attachment of excitable cells; a power source configured to deliver an electrical signal capable of electro-stimulating excitable cells; an impedance analyzer that resolves consecutive cell-substrate impedance measurements at 10 millisecond time resolution; and an extracellular recording amplifier that measures extracellular potential, wherein each well comprises:
  i) a pair of impedance monitoring electrodes communicatively coupled to the impedance analyzer thereby permitting impedance monitoring of excitable cells attached to the substrate; and
  ii) an extracellular recording electrode pair communicatively coupled to the extracellular recording amplifier thereby permitting extracellular recording of excitable cells attached to the substrate;
wherein at least one electrode from the impedance monitoring electrodes or at least one electrode from the extracellular electrode pair is also at least one of a pair of electrostimulation electrodes configured to receive the electrical signal from the power source and delivering an electro-stimulating signal to the well for electro-stimulation of excitable cells attached to the substrate, thereby permitting electro-stimulation of excitable cells and either extracellular recording or impedance monitoring of attached cells using a shared electrode at different time points of a same sample;

b) adding a sample of cardiomyocyte or cardiomyocyte precursor cells to the device;
c) electro-stimulating the cells at a regular time interval to affect excitation-contraction coupling of the cells;
d) adding a compound to the well;
e) impedance monitoring the electro-stimulated cells at 10 millisecond time resolution;
f) extracellular recording of the electro-stimulated cells over time; and
g) assessing the effect of compound administration on cell beating.

4. A method for monitoring excitable cells, the method comprising:
a) providing a system for monitoring excitable cells comprising a device comprising at least one well, each well having a bottom comprising a nonconductive substrate, wherein the substrate has a surface suitable for attachment of excitable cells; a power source configured to deliver an electrical signal capable of electro-stimulating excitable cells; and an impedance analyzer that resolves consecutive cell-substrate impedance measurements within 10 milliseconds apart, wherein each well comprises:
  i) a pair of electro-stimulation electrodes configured to receive the electrical signal from the power source thereby delivering an electro-stimulating signal to the well for electro-stimulation of excitable cells attached to the substrate; and
  ii) a pair of impedance monitoring electrodes communicatively coupled to the impedance analyzer permitting cell-substrate impedance monitoring of excitable cells attached to the substrate at 10 millisecond time resolution;
b) adding a sample of cardiomyocyte or cardiomyocyte precursor cells to the device;
c) electro-stimulating the cells to affect cell beating;
d) impedance monitoring the electro-stimulated cells at 10 millisecond time resolution; and
e) resolving the beating cycle of the cells.

5. The method according to claim 4, wherein the beating cycle is resolved using the monitored impedance.

* * * * *